US008188061B2

(12) United States Patent
Soutschek et al.

(10) Patent No.: US 8,188,061 B2
(45) Date of Patent: May 29, 2012

(54) RNAI MODULATION OF APOB AND USES THEREOF

(75) Inventors: Juergen Soutschek, Kasendorf (DE);
Hans-Peter Vornlocher, Bayreuth (DE);
Philipp Hadwiger, Altenkunstadt (DE);
Sayda Elbashir, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 250 days.

(21) Appl. No.: 12/728,139

(22) Filed: Mar. 19, 2010

(65) Prior Publication Data

US 2010/0216866 A1    Aug. 26, 2010

Related U.S. Application Data

(62) Division of application No. 12/400,744, filed on Mar. 9, 2009, now Pat. No. 7,723,317, which is a division of application No. 11/235,385, filed on Sep. 26, 2005, now Pat. No. 7,528,118.

(60) Provisional application No. 60/613,141, filed on Sep. 24, 2004.

(51) Int. Cl.
*A61K 31/70* (2006.01)
*C07H 21/02* (2006.01)
*C07H 21/04* (2006.01)
*C12Q 1/68* (2006.01)

(52) U.S. Cl. ............... 514/44 A; 536/23.1; 536/24.1; 536/24.5

(58) Field of Classification Search ............... None
See application file for complete search history.

(56) References Cited

U.S. PATENT DOCUMENTS

| 7,427,605 B2 | 9/2008 | Davis et al. |
| 7,718,629 B2 | 5/2010 | Bumcrot et al. |
| 2003/0143732 A1 | 7/2003 | Fosnaugh et al. |
| 2003/0170891 A1 | 9/2003 | McSwiggen |
| 2004/0259247 A1 | 12/2004 | Tuschl et al. |
| 2006/0263435 A1 | 11/2006 | Davis et al. |
| 2007/0004664 A1 | 1/2007 | McSwiggen et al. |
| 2007/0031844 A1 | 2/2007 | Khvorova et al. |
| 2007/0281899 A1 | 12/2007 | Bumcrot et al. |
| 2009/0149403 A1 | 6/2009 | MacLachlan et al. |
| 2011/0015250 A1 | 1/2011 | Bumcrot et al. |

FOREIGN PATENT DOCUMENTS

| WO | WO 2004/080406 | 9/2004 |
| WO | WO 2004/090108 | 10/2004 |

OTHER PUBLICATIONS

Invitation Pursuant to Article 94(3) and Rule 71(1) EPC, mailed Nov. 23, 2011, European Patent Application No. EP 05802154.4, 3 pages.
Fitzgerald, K., et al., "Abstract 583: RNAi Therapeutics for the Lowering of Cholesterol," Circulation, 2007, p. II_105, vol. 116, American Heart Association, Inc.
Agrawal, S., et al., "Antisense oligonucleotides: towards clinical trials." Trends in Biotechnology. Oct. 1996, vol. 14, pp. 376-387.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in *Caenorhabditis elegans*," Nature, Feb. 19, 1998, pp. 806-811, vol. 391.
Tuschl, T., "Functional genomics: RNA sets the standard," Nature, Jan. 16, 2003, vol. 421, No. 6920, pp. 220-221.
Tuschl T., "RNA Interference and Small Interfering RNAs" Chembiochem, 2001, pp. 239-245, vol. 2.
Tuschl, T., et al., "Small Interfering RNAs: A Revolutionary Tool for the Analysis of Gene Function and Gene Therapy," Molecular Interventions, 2002, pp. 158-167, vol. 2, No. 3.
Tuschl, T., "Mammalian RNA Interference," RNAi, A Guide to Gene Silencing, Chapter 13, G.J. Hannon (ed,), 2003, pp. 265-295.
Tuschl, T., et al., "Targeted mRNA Degradation by Double-Stranded RNA In Vitro," Genes & Development, 1999, pp. 3191-3197, vol. 13.
Tuschl, T., "Expanding small RNA interference," Nature Biotechnology, May 2002, pp. 446-448, vol. 20.
Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Soutschek, J., et al., "Therapeutic silencing of an endogenous gene by systemic administration of modified siRNAs," Nature, Oct. 27, 2004, vol. 3121, pp. 1-7.
Examination Report for New Zealand Patent Application No. 583290, Feb. 23, 2010, 4 pages.
Response to Examination Report issued Feb. 23, 2010, filed on Jun. 16, 2010, for New Zealand Patent Application No. 583290, 5 pages.
Examination Report for New Zealand Patent Application No. 583290, Jul. 6, 2010, 2 pages. Response to Examination Report issued Jul. 6, 2010, filed on Aug. 5, 2010, for New Zealand Patent Application No. 583290, 1 page.
Examination Report for New Zealand Patent Application No. 586217, Jun. 22, 2010, 4 pages.
Examination Report for Australia Patent Application No. 2005289588, Aug. 26, 2010, 3 pages.
Examiner's Report for European Patent Application No. 05802154, Jul. 2, 2010, 4 pages.

(Continued)

*Primary Examiner* — Sean McGarry
(74) *Attorney, Agent, or Firm* — Fenwick & West LLP

(57) ABSTRACT

The invention relates to compositions and methods for modulating the expression of apolipoprotein B, and more particularly to the downregulation of apolipoprotein B by chemically modified oligonucleotides.

25 Claims, 14 Drawing Sheets

OTHER PUBLICATIONS

Response to the Official Communication pursuant to Article 94(3) EPC issued on Jul. 2, 2010, filed on Nov. 5, 2010, for European Patent Application No. 05802154, 9 pages.
Examiner's Report for European Patent Application No. 05802154, Dec. 17, 2009, 4 pages.
Response to the Official Communication pursuant to Article 94(3) EPC issued on Dec. 17, 2009, filed on Jun. 9, 2010, for European Patent Application No. 05802154, 11 pages.
Examiner's Report for European Patent Application No. 05802154, May 27, 2009, 4 pages.
Response to the Official Communication pursuant to Article 94(3) EPC issued on May 27, 2009, filed on Oct. 6, 2009, for European Patent Application No. 05802154, 3 pages.
First Office Action for China Patent Application No. 200580040296.9, May 31, 2010, 6 pages.
Response to First Office Action issued on May 31, 2010, for China Patent Application No. 200580040296.9, filed on Oct. 5, 2010, 12 pages.
Second Office Action for China Patent Application No. 200580040296.9, Nov. 16, 2010, 7 pages.
Examination Report for European Patent Application No. EP 058021544, Jan. 31, 2011, 4 Pages.
Examination Report for New Zealand Patent Application No. NZ 586217, mailed Aug. 18, 2011, 2 pages.
Response to Examination Report of Jun. 22, 2010, for New Zealand Patent Application No. 586217, response filed on Aug. 2, 2011, 4 pages.
Reynolds, et al. (2004) "Rational siRNA design for RNA interference," Nature Biotechnology, vol. 22, No. 3, pp. 326-330.
Robbins, M., et al., "Stable expression of shRNAs in human $CD34^+$ progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Weil, et al (2002) "Targeting the Kinesin Eg5 to Monitor siRNA Transfection in Mammalian Cells," *Biotechniques* 33(6):1244-1248.
Zimmerman, et al. (2006) "RNAi-mediated gene silencing in non-human primates," *Nature*, vol. 441, May 4: 111-114.

SEQUENCE LISTING

```
<160> NUMBER OF SEQ ID NOS: 297

<210> SEQ ID NO 1
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 1
aagccuuggu ucagugugga c                                              21

<210> SEQ ID NO 2
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 2
guccacacug aaccaaggcu ugu                                            23

<210> SEQ ID NO 3
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 3
ugaacaccaa cuucuuccac g                                              21

<210> SEQ ID NO 4
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 4
cguggaagaa guugguguuc auc                                            23

<210> SEQ ID NO 5
<211> LENGTH: 21
<212> TYPE: RNA
<213> ORGANISM: Artificial Sequence
<220> FEATURE:
<223> OTHER INFORMATION: Synthetically generated oligonucleotide
```

-continued

```
<400> SEQUENCE: 5
gauugauuga ccguccauu c                                              21

<210> SEQ ID NO 6
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 6
gaauggacag gucaaucaau cuu                                           23

<210> SEQ ID NO 7
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 7
aauggacuca ucugcuacag c                                             21

<210> SEQ ID NO 8
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 8
gcuguagcag augaguccau uug                                           23

<210> SEQ ID NO 9
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 9
auugaccugu ccauucaaaa c                                             21

<210> SEQ ID NO 10
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 10
guuuugaaug gacaggucaa uca                                           23

<210> SEQ ID NO 11
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 11
uuugugacaa auaugggcau c                                             21

<210> SEQ ID NO 12
<211> LENGTH: 23
<212> TYPE: RNA
```

```
<213> ORGANISM: Artificial Sequence
<220> FEATURE:
<223> OTHER INFORMATION: Synthetically generated oligonucleotide

<400> SEQUENCE: 12
gaugcccaua uuugucacaa acu                                           23

<210> SEQ ID NO 13
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 13
cuugguucag uguggacagc c                                             21

<210> SEQ ID NO 14
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 14
ggcuguccac acugaaccaa ggc                                           23

<210> SEQ ID NO 15
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 15
uggacucauc ugcuacagcu u                                             21

<210> SEQ ID NO 16
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 16
aagcuguagc agaugagucc auu                                           23

<210> SEQ ID NO 17
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 17
auugauugac cuguccauuc a                                             21

<210> SEQ ID NO 18
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 18
ugaauggaca ggucaaucaa ucu                                           23
```

```
<210> SEQ ID NO 19
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 19
uugauugacc uguccauuca a                                              21

<210> SEQ ID NO 20
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 20
uugaauggac aggucaauca auc                                            23

<210> SEQ ID NO 21
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 21
caaauggacu caucugcuac a                                              21

<210> SEQ ID NO 22
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 22
uguagcagau gaguccauuu gga                                            23

<210> SEQ ID NO 23
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 23
gauugaccug uccauucaaa a                                              21

<210> SEQ ID NO 24
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 24
uuuugaaugg acaggucaau caa                                            23

<210> SEQ ID NO 25
<211> LENGTH: 21
<212> TYPE: RNA
<213> ORGANISM: Artificial Sequence
<220> FEATURE:
<223> OTHER INFORMATION: Synthetically generated oligonucleotide
```

```
<400> SEQUENCE: 25
ugauugaccu guccauucaa a                                           21

<210> SEQ ID NO 26
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 26
uuugaaugga caggucaauc aau                                         23

<210> SEQ ID NO 27
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 27
gguguauggc uucaacccug a                                           21

<210> SEQ ID NO 28
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 28
ucaggguuga agccauacac cuc                                         23

<210> SEQ ID NO 29
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 29
ucugugggau uccaucugcc a                                           21

<210> SEQ ID NO 30
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 30
uggcagaugg aaucccacag acu                                         23

<210> SEQ ID NO 31
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 31
agacuuccug aauaacuaug c                                           21

<210> SEQ ID NO 32
<211> LENGTH: 23
<212> TYPE: RNA
```

```
<213> ORGANISM: Artificial Sequence
<220> FEATURE:
<223> OTHER INFORMATION: Synthetically generated oligonucleotide

<400> SEQUENCE: 32
gcauaguuau ucaggaaguc uau                                               23

<210> SEQ ID NO 33
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 33
acaauuugau caguauauua a                                                 21

<210> SEQ ID NO 34
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 34
uuaauauacu gaucaaauug uau                                               23

<210> SEQ ID NO 35
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 35
ggacucaucu gcuacagcuu a                                                 21

<210> SEQ ID NO 36
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 36
uaagcuguag cagaugaguc cau                                               23

<210> SEQ ID NO 37
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 37
uuacuccaac gccagcucca c                                                 21

<210> SEQ ID NO 38
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 38
guggagcugg cguuggagua agc                                               23
```

-continued

```
<210> SEQ ID NO 39
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 39
gugacaaaua ugggcaucau c                                              21

<210> SEQ ID NO 40
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 40
gaugaugccc auauuuguca caa                                            23

<210> SEQ ID NO 41
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 41
guguauggcu ucaacccuga g                                              21

<210> SEQ ID NO 42
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 42
cucaggguug aagccauaca ccu                                            23

<210> SEQ ID NO 43
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 43
uaccguguau ggaaacugcu c                                              21

<210> SEQ ID NO 44
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 44
gagcaguuuc cauacacggu auc                                            23

<210> SEQ ID NO 45
<211> LENGTH: 21
<212> TYPE: RNA
<213> ORGANISM: Artificial Sequence
<220> FEATURE:
<223> OTHER INFORMATION: Synthetically generated oligonucleotide
```

```
<400> SEQUENCE: 45
gauaccgugu auggaaacug c                                              21

<210> SEQ ID NO 46
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 46
gcaguuucca uacacgguau cca                                            23

<210> SEQ ID NO 47
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 47
aaaucaagug ucaucacacu g                                              21

<210> SEQ ID NO 48
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 48
cagugugaug acacuugauu uaa                                            23

<210> SEQ ID NO 49
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 49
agguguaugg cuucaacccu g                                              21

<210> SEQ ID NO 50
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 50
caggguugaa gccauacacc ucu                                            23

<210> SEQ ID NO 51
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 51
guuugugaca aauaugggca u                                              21

<210> SEQ ID NO 52
<211> LENGTH: 23
<212> TYPE: RNA
```

```
<213> ORGANISM: Artificial Sequence
<220> FEATURE:
<223> OTHER INFORMATION: Synthetically generated oligonucleotide

<400> SEQUENCE: 52
augcccauau uugucacaaa cuc                                              23

<210> SEQ ID NO 53
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 53 auaccguguo uggaaacugc u                                                21

<210> SEQ ID NO 54
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 54
agcaguuucc auacacggua ucc                                              23

<210> SEQ ID NO 55
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 55
uaaaucaagu gucaucacac u                                                21

<210> SEQ ID NO 56
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 56
agugugauga cacuugauuu aaa                                              23

<210> SEQ ID NO 57
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 57
gagguguaug gcuucaaccc u                                                21

<210> SEQ ID NO 58
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 58
aggguugaag ccauacaccu cuu                                              23
```

<210> SEQ ID NO 59
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 59
uggcuucaac ccugagggca a                                              21

<210> SEQ ID NO 60
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 60
uugcccucag gguugaagcc aua                                            23

<210> SEQ ID NO 61
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 61
gaacaccaac uucuuccacg a                                              21

<210> SEQ ID NO 62
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 62
ucguggaaga aguugguguu cau                                            23

<210> SEQ ID NO 63
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 63
guauggcuuc aacccugagg g                                              21

<210> SEQ ID NO 64
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 64
cccucagggu ugaagccaua cac                                            23

<210> SEQ ID NO 65
<211> LENGTH: 21
<212> TYPE: RNA
<213> ORGANISM: Artificial Sequence
<220> FEATURE:
<223> OTHER INFORMATION: Synthetically generated oligonucleotide

```
<400> SEQUENCE: 65
auggcuucaa cccugagggc a                                          21

<210> SEQ ID NO 66
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 66
ugcccucagg guugaagcca uac                                        23

<210> SEQ ID NO 67
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 67
aacaccaacu ucuuccacga g                                          21

<210> SEQ ID NO 68
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 68
cucguggaag aaguuggugu uca                                        23

<210> SEQ ID NO 69
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 69
acaccaacuu cuuccacgag u                                          21

<210> SEQ ID NO 70
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 70
acucguggaa gaaguuggug uuc                                        23

<210> SEQ ID NO 71
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 71
caccaacuuc uuccacgagu c                                          21

<210> SEQ ID NO 72
<211> LENGTH: 23
<212> TYPE: RNA
```

-continued

<213> ORGANISM: Artificial Sequence
<220> FEATURE:
<223> OTHER INFORMATION: Synthetically generated oligonucleotide

<400> SEQUENCE: 72
gacucgugga agaaguuggu guu                                              23

<210> SEQ ID NO 73
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 73
gaugaacacc aacuucuucc a                                                21

<210> SEQ ID NO 74
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 74
uggaagaagu ugguguucau cug                                              23

<210> SEQ ID NO 75
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 75
augaacacca acuucuucca c                                                21

<210> SEQ ID NO 76
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 76
guggaagaag uugguguuca ucu                                              23

<210> SEQ ID NO 77
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 77
agaugaacac caacuucuuc c                                                21

<210> SEQ ID NO 78
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 78
ggaagaaguu gguguucauc ugg                                              23

```
<210> SEQ ID NO 79
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 79
auuccaucug ccaucucgag a                                              21

<210> SEQ ID NO 80
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 80
ucucgagaug gcagauggaa ucc                                            23

<210> SEQ ID NO 81
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 81
uuccaucugc caucucgaga g                                              21

<210> SEQ ID NO 82
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 82
cucucgagau ggcagaugga auc                                            23

<210> SEQ ID NO 83
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 83
acaagccuug guucagugug g                                              21

<210> SEQ ID NO 84
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 84
ccacacugaa ccaaggcuug uaa                                            23

<210> SEQ ID NO 85
<211> LENGTH: 21
<212> TYPE: RNA
<213> ORGANISM: Artificial Sequence
<220> FEATURE:
<223> OTHER INFORMATION: Synthetically generated oligonucleotide
```

```
<400> SEQUENCE: 85
uucaagucug ugggauucca u                                              21

<210> SEQ ID NO 86
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 86
auggaauccc acagacuuga agu                                            23

<210> SEQ ID NO 87
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 87
aaucaagugu caucacacug a                                              21

<210> SEQ ID NO 88
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 88
ucagugugau gacacuugau uua                                            23

<210> SEQ ID NO 89
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 89
uauggcuuca acccugaggg c                                              21

<210> SEQ ID NO 90
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 90
gcccucaggg uugaagccau aca                                            23

<210> SEQ ID NO 91
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 91
uugaccuguc cauucaaaac u                                              21

<210> SEQ ID NO 92
<211> LENGTH: 23
<212> TYPE: RNA
```

```
<213> ORGANISM: Artificial Sequence
<220> FEATURE:
<223> OTHER INFORMATION: Synthetically generated oligonucleotide

<400> SEQUENCE: 92
aguuuugaau ggacagguca auc                                            23

<210> SEQ ID NO 93
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 93
aucaaguguc aucacacuga a                                              21

<210> SEQ ID NO 94
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 94
uucaguguga ugacacuuga uuu                                            23

<210> SEQ ID NO 95
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 95
ucaaguguca ucacacugaa u                                              21

<210> SEQ ID NO 96
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 96
auucagugug augacacuug auu                                            23

<210> SEQ ID NO 97
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 97
gucaucacac ugaauaccaa u                                              21

<210> SEQ ID NO 98
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 98
auugguauuc agugugauga cac                                            23
```

```
<210> SEQ ID NO 99
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 99
cuguccauuc aaaacuacca c                                           21

<210> SEQ ID NO 100
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 100
gugguaguuu ugaauggaca ggu                                         23

<210> SEQ ID NO 101
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 101
ccuguccauu caaaacuacc a                                           21

<210> SEQ ID NO 102
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 102
ugguaguuuu gaauggacag guc                                         23

<210> SEQ ID NO 103
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 103
aucacacuga auaccaaugc u                                           21

<210> SEQ ID NO 104
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 104
agcauuggua uucaguguga uga                                         23

<210> SEQ ID NO 105
<211> LENGTH: 21
<212> TYPE: RNA
<213> ORGANISM: Artificial Sequence
<220> FEATURE:
<223> OTHER INFORMATION: Synthetically generated oligonucleotide
```

```
<400> SEQUENCE: 105
accuguccau ucaaaacuac c                                        21

<210> SEQ ID NO 106
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 106
gguaguuuug aauggacagg uca                                      23

<210> SEQ ID NO 107
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 107
gaccugucca uucaaaacua c                                        21

<210> SEQ ID NO 108
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 108
guaguuuuga auggacaggu caa                                      23

<210> SEQ ID NO 109
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 109
caucacacug aauaccaaug c                                        21

<210> SEQ ID NO 110
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 110
gcauugguau ucagugugau gac                                      23

<210> SEQ ID NO 111
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 111
uacaagccuu gguucagugu g                                        21

<210> SEQ ID NO 112
<211> LENGTH: 23
<212> TYPE: RNA
```

```
<213> ORGANISM: Artificial Sequence
<220> FEATURE:
<223> OTHER INFORMATION: Synthetically generated oligonucleotide

<400> SEQUENCE: 112
cacacugaac caaggcuugu aaa                                              23

<210> SEQ ID NO 113
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 113
uguauggcuu caacccugag g                                                21

<210> SEQ ID NO 114
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 114
ccucaggguu gaagccauac acc                                              23

<210> SEQ ID NO 115
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 115
ugaccugucc auucaaaacu a                                                21

<210> SEQ ID NO 116
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 116
uaguuuugaa uggacagguc aau                                              23

<210> SEQ ID NO 117
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 117
ucaucacacu gaauaccaau g                                                21

<210> SEQ ID NO 118
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 118
cauugguauu cagugugaug aca                                              23
```

<210> SEQ ID NO 119
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 119
uugugacaaa uaugggcauc a                                                 21

<210> SEQ ID NO 120
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 120
ugaugcccau auuugcaca aac                                                23

<210> SEQ ID NO 121
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 121
caagugucau cacacugaau a                                                 21

<210> SEQ ID NO 122
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 122
uauucagugu gaugacacuu gau                                               23

<210> SEQ ID NO 123
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 123
uaacacuaag aaccagaaga u                                                 21

<210> SEQ ID NO 124
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 124
aucuucuggu ucuuaguguu agc                                               23

<210> SEQ ID NO 125
<211> LENGTH: 21
<212> TYPE: RNA
<213> ORGANISM: Artificial Sequence
<220> FEATURE:
<223> OTHER INFORMATION: Synthetically generated oligonucleotide

```
<400> SEQUENCE: 125
caauuugauc aguauauuaa a                                              21

<210> SEQ ID NO 126
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 126
uuuaauauac ugaucaaauu gua                                            23

<210> SEQ ID NO 127
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 127
cugaacauca agaggggcau c                                              21

<210> SEQ ID NO 128
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 128
gaugccccuc uugauguuca gga                                            23

<210> SEQ ID NO 129
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 129
ugaacaucaa gaggggcauc a                                              21

<210> SEQ ID NO 130
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 130
ugaugcsccu cuugauguuc agg                                            23

<210> SEQ ID NO 131
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 131
guccagcccc aucacuuuac a                                              21

<210> SEQ ID NO 132
<211> LENGTH: 23
<212> TYPE: RNA
```

```
<213> ORGANISM: Artificial Sequence
<220> FEATURE:
<223> OTHER INFORMATION: Synthetically generated oligonucleotide

<400> SEQUENCE: 132
uguaaaguga uggggcugga cac                                         23

<210> SEQ ID NO 133
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 133
cagccccauc acuuuacaag c                                           21

<210> SEQ ID NO 134
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 134
gcuuguaaag ugaugggcu gga                                          23

<210> SEQ ID NO 135
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 135
agccccauca cuuuacaagc c                                           21

<210> SEQ ID NO 136
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 136
ggcuuguaaa gugauggggc ugg                                         23

<210> SEQ ID NO 137
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 137
gaguuuguga caaauauggg c                                           21

<210> SEQ ID NO 138
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 138
gcccauauuu gucacaaacu cca                                         23
```

```
<210> SEQ ID NO 139
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 139
agggaaucuu auauuugauc c                                              21

<210> SEQ ID NO 140
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 140
ggaucaaaua uaagauuccc uuc                                            23

<210> SEQ ID NO 141
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 141
uuacugagcu gagaggccuc a                                              21

<210> SEQ ID NO 142
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 142
ugaggccucu cagcucagua acc                                            23

<210> SEQ ID NO 143
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 143
auugggaaga agaggcagcu u                                              21

<210> SEQ ID NO 144
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 144
aagcugccuc uucuucccaa uua                                            23

<210> SEQ ID NO 145
<211> LENGTH: 21
<212> TYPE: RNA
<213> ORGANISM: Artificial Sequence
<220> FEATURE:
<223> OTHER INFORMATION: Synthetically generated oligonucleotide
```

-continued

```
<400> SEQUENCE: 145
ucacauccuc caguggcuga a                                              21

<210> SEQ ID NO 146
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 146
uucagccacu ggaggaugug agu                                            23

<210> SEQ ID NO 147
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 147
gccccaucac uuuacaagcc u                                              21

<210> SEQ ID NO 148
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 148
aggcuuguaa agugaugggg cug                                            23

<210> SEQ ID NO 149
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 149
ccagccccau cacuuuacaa g                                              21

<210> SEQ ID NO 150
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 150
cuuguaaagu gaugggcug gac                                             23

<210> SEQ ID NO 151
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 151
aagggaaucu uauauuugau c                                              21

<210> SEQ ID NO 152
<211> LENGTH: 23
<212> TYPE: RNA
```

```
<213> ORGANISM: Artificial Sequence
<220> FEATURE:
<223> OTHER INFORMATION: Synthetically generated oligonucleotide

<400> SEQUENCE: 152
gaucaaauau aagauucccu ucu                                              23

<210> SEQ ID NO 153
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 153
cuuuacaagc cuugguucag u                                                21

<210> SEQ ID NO 154
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 154
acugaaccaa ggcuuguaaa gug                                              23

<210> SEQ ID NO 155
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 155
ggaaucuuau auugaucca a                                                 21

<210> SEQ ID NO 156
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 156
uuggaucaaa uauaagauuc ccu                                              23

<210> SEQ ID NO 157
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 157
gaagggaauc uuauauuuga u                                                21

<210> SEQ ID NO 158
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 158
aucaaauaua agauucccuu cua                                              23
```

```
<210> SEQ ID NO 159
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 159
aaauagaagg gaaucuuaua u                                                 21

<210> SEQ ID NO 160
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 160
auauaagauu cccuucuauu uug                                               23

<210> SEQ ID NO 161
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 161
uagaagggaa ucuuauauuu g                                                 21

<210> SEQ ID NO 162
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 162
caaauauaag auucccuucu auu                                               23

<210> SEQ ID NO 163
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 163
gacuuccuga auaacuaugc a                                                 21

<210> SEQ ID NO 164
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 164
ugcauaguua uucaggaagu cua                                               23

<210> SEQ ID NO 165
<211> LENGTH: 21
<212> TYPE: RNA
<213> ORGANISM: Artificial Sequence
<220> FEATURE:
<223> OTHER INFORMATION: Synthetically generated oligonucleotide
```

```
<400> SEQUENCE: 165
gcaaggaucu ggagaaacaa c                                               21

<210> SEQ ID NO 166
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 166
guuguuucuc cagauccuug cac                                             23

<210> SEQ ID NO 167
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 167
caaggaucug gagaaacaac a                                               21

<210> SEQ ID NO 168
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 168
uguuguuucu ccagauccuu gca                                             23

<210> SEQ ID NO 169
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 169
acggcuagcu gugaaagguc c                                               21

<210> SEQ ID NO 170
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 170
ggaccuuuca cagcuagccg uga                                             23

<210> SEQ ID NO 171
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine conjugated cholesterol

<400> SEQUENCE: 171
ccacaugaag cagcacgacu n                                               21
```

<210> SEQ ID NO 172
<211> LENGTH: 20
<212> TYPE: RNA
<213> ORGANISM: Artificial Sequence
<220> FEATURE:
<223> OTHER INFORMATION: Synthetically generated oligonucleotide

<400> SEQUENCE: 172
aagucgugcu gcuucaugug                                                   20

<210> SEQ ID NO 173
<211> LENGTH: 41
<212> TYPE: DNA
<213> ORGANISM: Artificial Sequence
<220> FEATURE:
<223> OTHER INFORMATION: Probe sequence for murine ApoB

<400> SEQUENCE: 173
ctcattctcc agcagcaggg tttttctctt ggaaagaaag t                            41

<210> SEQ ID NO 174
<211> LENGTH: 41
<212> TYPE: DNA
<213> ORGANISM: Artificial Sequence
<220> FEATURE:
<223> OTHER INFORMATION: Probe sequence for murine ApoB

<400> SEQUENCE: 174
gaagcggccg tttgttgata tttttctctt ggaaagaaag t                            41

<210> SEQ ID NO 175
<211> LENGTH: 41
<212> TYPE: DNA
<213> ORGANISM: Artificial Sequence
<220> FEATURE:
<223> OTHER INFORMATION: Probe sequence for murine ApoB

<400> SEQUENCE: 175
gtttttgctg tctgcaccca tttttctctt ggaaagaaag t                            41

<210> SEQ ID NO 176
<211> LENGTH: 48
<212> TYPE: DNA
<213> ORGANISM: Artificial Sequence
<220> FEATURE:
<223> OTHER INFORMATION: Probe sequence for murine ApoB

<400> SEQUENCE: 176
taaatattgt ccattttga gaagaagttt ttctcttgga aagaaagt                      48

<210> SEQ ID NO 177
<211> LENGTH: 42
<212> TYPE: DNA
<213> ORGANISM: Artificial Sequence
<220> FEATURE:
<223> OTHER INFORMATION: Probe sequence for murine ApoB

<400> SEQUENCE: 177
cattcagctt cagtggctcc attttctct tggaaagaaa gt                            42

<210> SEQ ID NO 178
<211> LENGTH: 45
<212> TYPE: DNA
<213> ORGANISM: Artificial Sequence
<220> FEATURE:
<223> OTHER INFORMATION: Probe sequence for murine ApoB

```
<400> SEQUENCE: 178
aatgtctgca tttagcctat ggcttttttc tcttggaaag aaagt          45

<210> SEQ ID NO 179
<211> LENGTH: 44
<212> TYPE: DNA
<213> ORGANISM: Artificial Sequence
<220> FEATURE:
<223> OTHER INFORMATION: Probe sequence for murine ApoB

<400> SEQUENCE: 179
agcccaagct ctgcattcaa tttttaggca taggacccgt gtct           44

<210> SEQ ID NO 180
<211> LENGTH: 44
<212> TYPE: DNA
<213> ORGANISM: Artificial Sequence
<220> FEATURE:
<223> OTHER INFORMATION: Probe sequence for murine ApoB

<400> SEQUENCE: 180
atttcatgga tgccccagag tttttaggca taggacccgt gtct           44

<210> SEQ ID NO 181
<211> LENGTH: 48
<212> TYPE: DNA
<213> ORGANISM: Artificial Sequence
<220> FEATURE:
<223> OTHER INFORMATION: Probe sequence for murine ApoB

<400> SEQUENCE: 181
actgaatttt gcatggtgtt ctttttttta ggcataggac ccgtgtct       48

<210> SEQ ID NO 182
<211> LENGTH: 43
<212> TYPE: DNA
<213> ORGANISM: Artificial Sequence
<220> FEATURE:
<223> OTHER INFORMATION: Probe sequence for murine ApoB

<400> SEQUENCE: 182
gggcagctct cccatcaagt ttttaggcat aggacccgtg tct            43

<210> SEQ ID NO 183
<211> LENGTH: 45
<212> TYPE: DNA
<213> ORGANISM: Artificial Sequence
<220> FEATURE:
<223> OTHER INFORMATION: Probe sequence for murine ApoB

<400> SEQUENCE: 183
gaatcatggc ctggtaaatg cttttaggc ataggacccg tgtct           45

<210> SEQ ID NO 184
<211> LENGTH: 48
<212> TYPE: DNA
<213> ORGANISM: Artificial Sequence
<220> FEATURE:
<223> OTHER INFORMATION: Probe sequence for murine ApoB

<400> SEQUENCE: 184
cagcatagga gcccatcaaa tcatttttta ggcataggac ccgtgtct       48

<210> SEQ ID NO 185
<211> LENGTH: 51
<212> TYPE: DNA
```

```
<213> ORGANISM: Artificial Sequence
<220> FEATURE:
<223> OTHER INFORMATION: Probe sequence for murine ApoB

<400> SEQUENCE: 185
gactgtgtgt gtggtcaagt ttcatctttt ttaggcatag acccgtgtc t          51

<210> SEQ ID NO 186
<211> LENGTH: 50
<212> TYPE: DNA
<213> ORGANISM: Artificial Sequence
<220> FEATURE:
<223> OTHER INFORMATION: Probe sequence for murine ApoB

<400> SEQUENCE: 186
atagggctgt agctgtaagt taaaattttt taggcatagg acccgtgtct            50

<210> SEQ ID NO 187
<211> LENGTH: 50
<212> TYPE: DNA
<213> ORGANISM: Artificial Sequence
<220> FEATURE:
<223> OTHER INFORMATION: Probe sequence for murine ApoB

<400> SEQUENCE: 187
gtcaaatcta gagcaccata tctcagtttt taggcatagg acccgtgtct            50

<210> SEQ ID NO 188
<211> LENGTH: 44
<212> TYPE: DNA
<213> ORGANISM: Artificial Sequence
<220> FEATURE:
<223> OTHER INFORMATION: Probe sequence for murine ApoB

<400> SEQUENCE: 188
gccgaaacct tccattgttg tttttaggca taggacccgt gtct                  44

<210> SEQ ID NO 189
<211> LENGTH: 53
<212> TYPE: DNA
<213> ORGANISM: Artificial Sequence
<220> FEATURE:
<223> OTHER INFORMATION: Probe sequence for murine ApoB

<400> SEQUENCE: 189
agatatgttt cagctcatta ttttgatagt ttttaggcat aggacccgtg tct        53

<210> SEQ ID NO 190
<211> LENGTH: 54
<212> TYPE: DNA
<213> ORGANISM: Artificial Sequence
<220> FEATURE:
<223> OTHER INFORMATION: Probe sequence for murine ApoB

<400> SEQUENCE: 190
ctactaccag gtcagtataa gatatggtat ttttaggca taggacccgt gtct         54

<210> SEQ ID NO 191
<211> LENGTH: 47
<212> TYPE: DNA
<213> ORGANISM: Artificial Sequence
<220> FEATURE:
<223> OTHER INFORMATION: Probe sequence for murine ApoB

<400> SEQUENCE: 191
gaattcgaca ccctgaacct tagtttttag gcataggacc cgtgtct               47
```

```
<210> SEQ ID NO 192
<211> LENGTH: 21
<212> TYPE: DNA
<213> ORGANISM: Artificial Sequence
<220> FEATURE:
<223> OTHER INFORMATION: Probe sequence for murine ApoB

<400> SEQUENCE: 192
tccccagtga cacctctgtg a                                           21

<210> SEQ ID NO 193
<211> LENGTH: 24
<212> TYPE: DNA
<213> ORGANISM: Artificial Sequence
<220> FEATURE:
<223> OTHER INFORMATION: Probe sequence for murine ApoB

<400> SEQUENCE: 193
tcggctgagt ttgaagttga agat                                        24

<210> SEQ ID NO 194
<211> LENGTH: 19
<212> TYPE: DNA
<213> ORGANISM: Artificial Sequence
<220> FEATURE:
<223> OTHER INFORMATION: Probe sequence for murine ApoB

<400> SEQUENCE: 194
tggacagcct cagcccttc                                              19

<210> SEQ ID NO 195
<211> LENGTH: 25
<212> TYPE: DNA
<213> ORGANISM: Artificial Sequence
<220> FEATURE:
<223> OTHER INFORMATION: Probe sequence for murine ApoB

<400> SEQUENCE: 195
tccagtgaga gacctgcaat gttca                                       25

<210> SEQ ID NO 196
<211> LENGTH: 26
<212> TYPE: DNA
<213> ORGANISM: Artificial Sequence
<220> FEATURE:
<223> OTHER INFORMATION: Probe sequence for murine ApoB

<400> SEQUENCE: 196
tctgcttata gaacttgtct ccactg                                      26

<210> SEQ ID NO 197
<211> LENGTH: 27
<212> TYPE: DNA
<213> ORGANISM: Artificial Sequence
<220> FEATURE:
<223> OTHER INFORMATION: Probe sequence for murine ApoB

<400> SEQUENCE: 197
gtcgttgctt aaagtagtta tgaaaga                                     27

<210> SEQ ID NO 198
<211> LENGTH: 22
<212> TYPE: DNA
<213> ORGANISM: Artificial Sequence
<220> FEATURE:
<223> OTHER INFORMATION: Probe sequence for murine ApoB
```

-continued

<400> SEQUENCE: 198
gttcctttaa agttgccacc ca                                       22

<210> SEQ ID NO 199
<211> LENGTH: 24
<212> TYPE: DNA
<213> ORGANISM: Artificial Sequence
<220> FEATURE:
<223> OTHER INFORMATION: Probe sequence for murine ApoB

<400> SEQUENCE: 199
ccacagtgtc tgctctgtaa cttg                                     24

<210> SEQ ID NO 200
<211> LENGTH: 49
<212> TYPE: DNA
<213> ORGANISM: Artificial Sequence
<220> FEATURE:
<223> OTHER INFORMATION: Probe sequence for human ApoB

<400> SEQUENCE: 200
gattggattt tcagaatact gtatagcttt tttctcttgg aaagaaagt           49

<210> SEQ ID NO 201
<211> LENGTH: 41
<212> TYPE: DNA
<213> ORGANISM: Artificial Sequence
<220> FEATURE:
<223> OTHER INFORMATION: Probe sequence for human ApoB

<400> SEQUENCE: 201
cctgcttcgt tgctgaggt tttttctctt ggaaagaaag t                    41

<210> SEQ ID NO 202
<211> LENGTH: 42
<212> TYPE: DNA
<213> ORGANISM: Artificial Sequence
<220> FEATURE:
<223> OTHER INFORMATION: Probe sequence for human ApoB

<400> SEQUENCE: 202
gcagtgatgg aagctgcgat attttttctct tggaaagaaa gt                 42

<210> SEQ ID NO 203
<211> LENGTH: 47
<212> TYPE: DNA
<213> ORGANISM: Artificial Sequence
<220> FEATURE:
<223> OTHER INFORMATION: Probe sequence for human ApoB

<400> SEQUENCE: 203
gaacttctaa tttggactct cctttgtttt tctcttggaa agaaagt             47

<210> SEQ ID NO 204
<211> LENGTH: 40
<212> TYPE: DNA
<213> ORGANISM: Artificial Sequence
<220> FEATURE:
<223> OTHER INFORMATION: Probe sequence for human ApoB

<400> SEQUENCE: 204
actccttcag agccagcggt ttttctcttg gaaagaaagt                     40

<210> SEQ ID NO 205
<211> LENGTH: 41
<212> TYPE: DNA

```
<213> ORGANISM: Artificial Sequence
<220> FEATURE:
<223> OTHER INFORMATION: Probe sequence for human ApoB

<400> SEQUENCE: 205
actcccatgc tccgttctca tttttctctt ggaaagaaag t                    41

<210> SEQ ID NO 206
<211> LENGTH: 46
<212> TYPE: DNA
<213> ORGANISM: Artificial Sequence
<220> FEATURE:
<223> OTHER INFORMATION: Probe sequence for human ApoB

<400> SEQUENCE: 206
agggtaagct gattgtttat cttgattttt ctcttggaaa gaaagt              46

<210> SEQ ID NO 207
<211> LENGTH: 46
<212> TYPE: DNA
<213> ORGANISM: Artificial Sequence
<220> FEATURE:
<223> OTHER INFORMATION: Probe sequence for human ApoB

<400> SEQUENCE: 207
ggttccattc cctatgtcag cattttagg cataggaccc gtgtct               46

<210> SEQ ID NO 208
<211> LENGTH: 50
<212> TYPE: DNA
<213> ORGANISM: Artificial Sequence
<220> FEATURE:
<223> OTHER INFORMATION: Probe sequence for human ApoB

<400> SEQUENCE: 208
attaatctta gggtttgaga gttgtgtttt taggcatagg acccgtgtct           50

<210> SEQ ID NO 209
<211> LENGTH: 49
<212> TYPE: DNA
<213> ORGANISM: Artificial Sequence
<220> FEATURE:
<223> OTHER INFORMATION: Probe sequence for human ApoB

<400> SEQUENCE: 209
cactgtgttt gattttccct caatattttt aggcatagga cccgtgtct            49

<210> SEQ ID NO 210
<211> LENGTH: 51
<212> TYPE: DNA
<213> ORGANISM: Artificial Sequence
<220> FEATURE:
<223> OTHER INFORMATION: Probe sequence for human ApoB

<400> SEQUENCE: 210
tgtatttttt tctgtgtgta aacttgcttt ttaggcatag gacccgtgtc t         51

<210> SEQ ID NO 211
<211> LENGTH: 49
<212> TYPE: DNA
<213> ORGANISM: Artificial Sequence
<220> FEATURE:
<223> OTHER INFORMATION: Probe sequence for human ApoB

<400> SEQUENCE: 211
caatcactcc attactaagc tccagttttt aggcatagga cccgtgtct            49
```

```
<210> SEQ ID NO 212
<211> LENGTH: 24
<212> TYPE: DNA
<213> ORGANISM: Artificial Sequence
<220> FEATURE:
<223> OTHER INFORMATION: Probe sequence for human ApoB

<400> SEQUENCE: 212
tgccaaaagt aggtacttca attg                                              24

<210> SEQ ID NO 213
<211> LENGTH: 24
<212> TYPE: DNA
<213> ORGANISM: Artificial Sequence
<220> FEATURE:
<223> OTHER INFORMATION: Probe sequence for human ApoB

<400> SEQUENCE: 213
tttgcatcta atgtgaaaag agga                                              24

<210> SEQ ID NO 214
<211> LENGTH: 24
<212> TYPE: DNA
<213> ORGANISM: Artificial Sequence
<220> FEATURE:
<223> OTHER INFORMATION: Probe sequence for human ApoB

<400> SEQUENCE: 214
catttgcttg aaaatcaaaa ttga                                              24

<210> SEQ ID NO 215
<211> LENGTH: 24
<212> TYPE: DNA
<213> ORGANISM: Artificial Sequence
<220> FEATURE:
<223> OTHER INFORMATION: Probe sequence for human ApoB

<400> SEQUENCE: 215
ggtacttgct ggagaacttc actg                                              24

<210> SEQ ID NO 216
<211> LENGTH: 23
<212> TYPE: DNA
<213> ORGANISM: Artificial Sequence
<220> FEATURE:
<223> OTHER INFORMATION: Probe sequence for human ApoB

<400> SEQUENCE: 216
gcatttccaa aaaacagcat ttc                                               23

<210> SEQ ID NO 217
<211> LENGTH: 40
<212> TYPE: DNA
<213> ORGANISM: Artificial Sequence
<220> FEATURE:
<223> OTHER INFORMATION: Probe sequence for murine GAPDH

<400> SEQUENCE: 217
caaatggcag ccctggtgat ttttctcttg gaaagaaagt                              40

<210> SEQ ID NO 218
<211> LENGTH: 43
<212> TYPE: DNA
<213> ORGANISM: Artificial Sequence
<220> FEATURE:
<223> OTHER INFORMATION: Probe sequence for murine GAPDH
```

```
<400> SEQUENCE: 218
ccttgactgt gccgttgaat ttttttctc ttggaaagaa agt                    43

<210> SEQ ID NO 219
<211> LENGTH: 41
<212> TYPE: DNA
<213> ORGANISM: Artificial Sequence
<220> FEATURE:
<223> OTHER INFORMATION: Probe sequence for murine GAPDH

<400> SEQUENCE: 219
gtctcgctcc tggaagatgg tttttctctt ggaaagaaag t                     41

<210> SEQ ID NO 220
<211> LENGTH: 39
<212> TYPE: DNA
<213> ORGANISM: Artificial Sequence
<220> FEATURE:
<223> OTHER INFORMATION: Probe sequence for murine GAPDH

<400> SEQUENCE: 220
cccggccttc tccatggttt tttctcttgg aaagaaagt                        39

<210> SEQ ID NO 221
<211> LENGTH: 46
<212> TYPE: DNA
<213> ORGANISM: Artificial Sequence
<220> FEATURE:
<223> OTHER INFORMATION: Probe sequence for murine GAPDH

<400> SEQUENCE: 221
aacaatctcc actttgccac tgtttttagg cataggaccc gtgtct                46

<210> SEQ ID NO 222
<211> LENGTH: 50
<212> TYPE: DNA
<213> ORGANISM: Artificial Sequence
<220> FEATURE:
<223> OTHER INFORMATION: Probe sequence for murine GAPDH

<400> SEQUENCE: 222
catgtagacc atgtagttga ggtcaatttt taggcatagg acccgtgtct            50

<210> SEQ ID NO 223
<211> LENGTH: 44
<212> TYPE: DNA
<213> ORGANISM: Artificial Sequence
<220> FEATURE:
<223> OTHER INFORMATION: Probe sequence for murine GAPDH

<400> SEQUENCE: 223
gacaagcttc ccattctcgg tttttaggca taggacccgt gtct                  44

<210> SEQ ID NO 224
<211> LENGTH: 43
<212> TYPE: DNA
<213> ORGANISM: Artificial Sequence
<220> FEATURE:
<223> OTHER INFORMATION: Probe sequence for murine GAPDH

<400> SEQUENCE: 224
tgatgggctt cccgttgatt ttttaggcat aggacccgtg tct                   43

<210> SEQ ID NO 225
<211> LENGTH: 44
<212> TYPE: DNA
```

```
<213> ORGANISM: Artificial Sequence
<220> FEATURE:
<223> OTHER INFORMATION: Probe sequence for murine GAPDH

<400> SEQUENCE: 225
gacatactca gcaccggcct tttttaggca taggacccgt gtct                    44

<210> SEQ ID NO 226
<211> LENGTH: 19
<212> TYPE: DNA
<213> ORGANISM: Artificial Sequence
<220> FEATURE:
<223> OTHER INFORMATION: Probe sequence for murine GAPDH

<400> SEQUENCE: 226 tgaagggtc gttgatggc                                                 19

<210> SEQ ID NO 227
<211> LENGTH: 23
<212> TYPE: DNA
<213> ORGANISM: Artificial Sequence
<220> FEATURE:
<223> OTHER INFORMATION: Probe sequence for murine GAPDH

<400> SEQUENCE: 227
ccgtgagtgg agtcatactg gaa                                           23

<210> SEQ ID NO 228
<211> LENGTH: 22
<212> TYPE: DNA
<213> ORGANISM: Artificial Sequence
<220> FEATURE:
<223> OTHER INFORMATION: Probe sequence for murine GAPDH

<400> SEQUENCE: 228
caccccattt gatgttagtg gg                                            22

<210> SEQ ID NO 229
<211> LENGTH: 24
<212> TYPE: DNA
<213> ORGANISM: Artificial Sequence
<220> FEATURE:
<223> OTHER INFORMATION: Probe sequence for murine GAPDH

<400> SEQUENCE: 229
ggtgaagaca ccagtagact ccac                                          24

<210> SEQ ID NO 230
<211> LENGTH: 41
<212> TYPE: DNA
<213> ORGANISM: Artificial Sequence
<220> FEATURE:
<223> OTHER INFORMATION: Probe sequence for human GAPDH

<400> SEQUENCE: 230
gaatttgcca tgggtggaat tttttctctt ggaaagaaag t                       41

<210> SEQ ID NO 231
<211> LENGTH: 41
<212> TYPE: DNA
<213> ORGANISM: Artificial Sequence
<220> FEATURE:
<223> OTHER INFORMATION: Probe sequence for human GAPDH

<400> SEQUENCE: 231
ggagggatct cgctcctgga tttttctctt ggaaagaaag t                       41
```

-continued

```
<210> SEQ ID NO 232
<211> LENGTH: 40
<212> TYPE: DNA
<213> ORGANISM: Artificial Sequence
<220> FEATURE:
<223> OTHER INFORMATION: Probe sequence for human GAPDH

<400> SEQUENCE: 232
ccccagcctt ctccatggtt ttttctcttg gaaagaaagt                              40

<210> SEQ ID NO 233
<211> LENGTH: 40
<212> TYPE: DNA
<213> ORGANISM: Artificial Sequence
<220> FEATURE:
<223> OTHER INFORMATION: Probe sequence for human GAPDH

<400> SEQUENCE: 233
gctcccccct gcaaatgagt ttttctcttg gaaagaaagt                              40

<210> SEQ ID NO 234
<211> LENGTH: 42
<212> TYPE: DNA
<213> ORGANISM: Artificial Sequence
<220> FEATURE:
<223> OTHER INFORMATION: Probe sequence for human GAPDH

<400> SEQUENCE: 234
agccttgacg gtgccatgtt tttaggcata ggacccgtgt ct                           42

<210> SEQ ID NO 235
<211> LENGTH: 45
<212> TYPE: DNA
<213> ORGANISM: Artificial Sequence
<220> FEATURE:
<223> OTHER INFORMATION: Probe sequence for human GAPDH

<400> SEQUENCE: 235
gatgacaagc ttcccgttct cttttttaggc ataggacccg tgtct                       45

<210> SEQ ID NO 236
<211> LENGTH: 46
<212> TYPE: DNA
<213> ORGANISM: Artificial Sequence
<220> FEATURE:
<223> OTHER INFORMATION: Probe sequence for human GAPDH

<400> SEQUENCE: 236
agatggtgat gggatttcca tttttttagg cataggaccc gtgtct                       46

<210> SEQ ID NO 237
<211> LENGTH: 44
<212> TYPE: DNA
<213> ORGANISM: Artificial Sequence
<220> FEATURE:
<223> OTHER INFORMATION: Probe sequence for human GAPDH

<400> SEQUENCE: 237
gcatcgcccc acttgatttt tttttaggca taggacccgt gtct                         44

<210> SEQ ID NO 238
<211> LENGTH: 43
<212> TYPE: DNA
<213> ORGANISM: Artificial Sequence
<220> FEATURE:
<223> OTHER INFORMATION: Probe sequence for human GAPDH
```

-continued

```
<400> SEQUENCE: 238
cacgacgtac tcagcgccat ttttaggcat aggacccgtg tct                    43

<210> SEQ ID NO 239
<211> LENGTH: 46
<212> TYPE: DNA
<213> ORGANISM: Artificial Sequence
<220> FEATURE:
<223> OTHER INFORMATION: Probe sequence for human GAPDH

<400> SEQUENCE: 239
ggcagagatg atgaccctt tgtttttagg cataggaccc gtgtct                  46

<210> SEQ ID NO 240
<211> LENGTH: 21
<212> TYPE: DNA
<213> ORGANISM: Artificial Sequence
<220> FEATURE:
<223> OTHER INFORMATION: Probe sequence for human GAPDH

<400> SEQUENCE: 240
ggtgaagacg ccagtggact c                                            21

<210> SEQ ID NO 241
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 21
<223> OTHER INFORMATION: n = guanine cholesterol conjugated to the
      3'-end via a pyrrolidine linker comprising a
      phosphorothioate

<400> SEQUENCE: 241
agguguaugg cuucaacccu n                                            21

<210> SEQ ID NO 242
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: um = 2'O-methyl uridine modification
<220> FEATURE:
<221> NAME/KEY: modified_base
<222> LOCATION: 22
<223> OTHER INFORMATION: cm = 2'O-methyl  cytidine modification
      phosphorothioate linkage
<220> FEATURE:
<221> NAME/KEY: misc_feature
<222> LOCATION: 23
<223> OTHER INFORMATION: n = uridine phosphorothioate linkage

<400> SEQUENCE: 242
caggguugaa gccauacacc ucn                                          23

<210> SEQ ID NO 243
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
```

```
<222> LOCATION: 4, 6, 8, 12, 20
<223> OTHER INFORMATION: um = 2'O-methyl uridine modification
<220> FEATURE:
<221> NAME/KEY: modified_base
<222> LOCATION: 14
<223> OTHER INFORMATION: cm = 2'O-methyl cytidine modification
<220> FEATURE:
<221> NAME/KEY: misc_feature
<222> LOCATION: 21
<223> OTHER INFORMATION: n = guanine cholesterol conjugated to the
      3'-end via a pyrrolidine linker comprising a
      phosphorothioate

<400> SEQUENCE: 243
agguguaugg cuucaacccu n                                              21

<210> SEQ ID NO 244
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 1, 13, 17
<223> OTHER INFORMATION: cm = 2'O-methyl cytidine modification
<220> FEATURE:
<221> NAME/KEY: modified_base
<222> LOCATION: 6, 7, 15
<223> OTHER INFORMATION: um = 2'O-methyl uridine modification
<220> FEATURE:
<221> NAME/KEY: misc_feature
<222> LOCATION: 22
<223> OTHER INFORMATION: n = cytidine phosphorothioate linkage
<220> FEATURE:
<221> NAME/KEY: misc_feature
<222> LOCATION: 23
<223> OTHER INFORMATION: n = uridine phosphorothioate linkage

<400> SEQUENCE: 244
caggguugaa gccauacacc unn                                            23

<210> SEQ ID NO 245
<211> LENGTH: 28
<212> TYPE: DNA
<213> ORGANISM: Artificial Sequence
<220> FEATURE:
<223> OTHER INFORMATION: Probe sequence

<400> SEQUENCE: 245
gattgattga cctgtccatt ctcttctt                                       28

<210> SEQ ID NO 246
<211> LENGTH: 28
<212> TYPE: DNA
<213> ORGANISM: Artificial Sequence
<220> FEATURE:
<223> OTHER INFORMATION: Probe sequence

<400> SEQUENCE: 246
caccaacttc ttccacgagt ctcttctt                                       28

<210> SEQ ID NO 247
<211> LENGTH: 28
<212> TYPE: DNA
<213> ORGANISM: Artificial Sequence
<220> FEATURE:
<223> OTHER INFORMATION: Probe sequence

<400> SEQUENCE: 247
gagtttgtga caaatatggg ctcttctt                                       28
```

```
<210> SEQ ID NO 248
<211> LENGTH: 28
<212> TYPE: DNA
<213> ORGANISM: Artificial Sequence
<220> FEATURE:
<223> OTHER INFORMATION: Probe sequence

<400> SEQUENCE: 248
ctttacaagc cttggttcag ttcttctt                                            28

<210> SEQ ID NO 249
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 4, 6, 8, 12, 20
<223> OTHER INFORMATION: um = 2'O-methyl uridine modification
<220> FEATURE:
<221> NAME/KEY: modified_base
<222> LOCATION: 14
<223> OTHER INFORMATION: cm =  2'O-methyl cytidine modification
<220> FEATURE:
<221> NAME/KEY: misc_feature
<222> LOCATION: 21
<223> OTHER INFORMATION: n = guanine phosphorothioate linkage

<400> SEQUENCE: 249
agguguaugg cuucaacccu n                                                   21

<210> SEQ ID NO 250
<211> LENGTH: 28
<212> TYPE: DNA
<213> ORGANISM: Artificial Sequence
<220> FEATURE:
<223> OTHER INFORMATION: Probe sequence

<400> SEQUENCE: 250
ggaatcttat atttgatcca atcttctt                                            28

<210> SEQ ID NO 251
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm= 2'O-methyl cytidine modification
<220> FEATURE:
<221> NAME/KEY: modified_base
<222> LOCATION: 22
<223> OTHER INFORMATION: um = 2'O-methyl cytidine modification
      phosphorothioate linkage
<220> FEATURE:
<221> NAME/KEY: misc_feature
<222> LOCATION: 23
<223> OTHER INFORMATION: n = uridine phosphorothioate linkage

<400> SEQUENCE: 251
uuggaucaaa uauaagauuc ccn                                                 23

<210> SEQ ID NO 252
<211> LENGTH: 21
<212> TYPE: RNA
<213> ORGANISM: Artificial Sequence
<220> FEATURE:
```

```
<223> OTHER INFORMATION: Synthetically generated siRNA
<220> FEATURE:
<221> NAME/KEY: misc_feature
<222> LOCATION: 21
<223> OTHER INFORMATION: n =adenine cholesterol conjugated to the 3'-end
      via a pyrrolidine linker comprising a
      phosphorothioate

<400> SEQUENCE: 252
ggaaucuuau auuugaucca n                                              21

<210> SEQ ID NO 253
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 21
<223> OTHER INFORMATION: n = uridine cholesterol conjugated to the
      3'-end via a pyrrolidine linker comprising a
      phosphorothioate

<400> SEQUENCE: 253
gucaucacac ugaauaccaa n                                              21

<210> SEQ ID NO 254
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm =  2'O-methyl  cytidine modification
<220> FEATURE:
<221> NAME/KEY: modified_base
<222> LOCATION: 22
<223> OTHER INFORMATION: am=  2'O-methyl  adenine modification
<220> FEATURE:
<221> NAME/KEY: misc_feature
<222> LOCATION: 23
<223> OTHER INFORMATION: n = cytidine phosphorothioate linkage

<400> SEQUENCE: 254
auugguauuc agugugauga can                                            23

<210> SEQ ID NO 255
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 3, 6, 8, 18
<223> OTHER INFORMATION: cm =  2'O-methyl  cytidine modification
<220> FEATURE:
<221> NAME/KEY: modified_base
<222> LOCATION: 11, 15
<223> OTHER INFORMATION: um = 2'O-methyl uridine modification
<220> FEATURE:
<221> NAME/KEY: misc_feature
<222> LOCATION: 21
<223> OTHER INFORMATION: n = uridine cholesterol conjugated to the
      3'-end via a pyrrolidine linker comprising a
      phosphorothioate

<400> SEQUENCE: 255
gucaucacac ugaauaccaa n                                              21
```

<210> SEQ ID NO 256
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 2, 3, 6, 8, 13, 15, 18
<223> OTHER INFORMATION: um = 2'O-methyl uridine modification
<220> FEATURE:
<221> NAME/KEY: modified_base
<222> LOCATION: 10, 21
<223> OTHER INFORMATION: cm = 2'O-methyl cytidine modification
<220> FEATURE:
<221> NAME/KEY: misc_feature
<222> LOCATION: 22
<223> OTHER INFORMATION: n = adenine phosphorothioate linkage
<220> FEATURE:
<221> NAME/KEY: misc_feature
<222> LOCATION: 23
<223> OTHER INFORMATION: n = cytidine phosphorothioate linkage

<400> SEQUENCE: 256
auugguauuc agugugauga cnn                                            23

<210> SEQ ID NO 257
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 1, 2, 11, 13, 18
<223> OTHER INFORMATION: um = 2'O-methyl uridine modification
<220> FEATURE:
<221> NAME/KEY: modified_base
<222> LOCATION: 7, 21
<223> OTHER INFORMATION: cm = 2'O-methyl cytidine modification
<220> FEATURE:
<221> NAME/KEY: modified_base
<222> LOCATION: 22
<223> OTHER INFORMATION: cm = 2'O-methyl cytidine modification
      phosphorothioate linkage
<220> FEATURE:
<221> NAME/KEY: misc_feature
<222> LOCATION: 23
<223> OTHER INFORMATION: n = uridine phosphorothioate linkage

<400> SEQUENCE: 257
uuggaucaaa uauaagauuc ccn                                            23

<210> SEQ ID NO 258
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 7, 8, 10, 12, 13, 14,
<223> OTHER INFORMATION: um = 2'O-methyl uridine modification
<220> FEATURE:
<221> NAME/KEY: modified_base
<222> LOCATION: 19
<223> OTHER INFORMATION: cm = 2'O-methyl cytidine modification
<220> FEATURE:
<221> NAME/KEY: misc_feature
<222> LOCATION: 21
<223> OTHER INFORMATION: n = adenine cholesterol conjugated to the
      3'-end via a pyrrolidine linker comprising a
      phosphorothioate

<400> SEQUENCE: 258
ggaaucuuau auuugaucca n        21

<210> SEQ ID NO 259
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: gm = 2'O-methyl guanosine modification
<220> FEATURE:
<221> NAME/KEY: modified_base
<222> LOCATION: 22
<223> OTHER INFORMATION: um = 2'O-methyl uridine modification
      phosphorothioate linkage
<220> FEATURE:
<221> NAME/KEY: misc_feature
<222> LOCATION: 23
<223> OTHER INFORMATION: n = guanosine phosphorothioate linkage

<400> SEQUENCE: 259
acugaaccaa ggcuuguaaa gun        23

<210> SEQ ID NO 260
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: misc_feature
<222> LOCATION: 21
<223> OTHER INFORMATION: n = uridine cholesterol conjugated to the
      3'-end via a pyrrolidine linker comprising a
      phosphorothioate

<400> SEQUENCE: 260
cuuuacaagc cuugguucag n        21

<210> SEQ ID NO 261
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 3, 6, 8, 18
<223> OTHER INFORMATION: cm = 2'O-methyl cytidine modification
<220> FEATURE:
<221> NAME/KEY: modified_base
<222> LOCATION: 11, 15
<223> OTHER INFORMATION: um = 2'O-methyl uridine modification
<220> FEATURE:
<221> NAME/KEY: misc_feature
<222> LOCATION: 21
<223> OTHER INFORMATION: n = uridine phosphorothioate linkage

<400> SEQUENCE: 261
gucaucacac ugaauaccaa n        21

<210> SEQ ID NO 262
<211> LENGTH: 21
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 2, 3, 4, 12, 13, 16

-continued

```
<223> OTHER INFORMATION: um = 2'O-methyl uridine modification
<220> FEATURE:
<221> NAME/KEY: modified_base
<222> LOCATION: 6, 18
<223> OTHER INFORMATION: cm = 2'O-methyl cytidine modification
<220> FEATURE:
<221> NAME/KEY: misc_feature
<222> LOCATION: 21
<223> OTHER INFORMATION: n = uridine phosphorothioate linkage

<400> SEQUENCE: 262
cuuuacaagc cuugguucag n                                        21

<210> SEQ ID NO 263
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 3, 14, 15, 17
<223> OTHER INFORMATION: um = 2'O-methyl uridine modification
<220> FEATURE:
<221> NAME/KEY: modified_base
<222> LOCATION: 8
<223> OTHER INFORMATION: cm = 2'O-methyl cytidine modification
<220> FEATURE:
<221> NAME/KEY: modified_base
<222> LOCATION: 21
<223> OTHER INFORMATION: gm = 2'O-methyl guanosine modification
<220> FEATURE:
<221> NAME/KEY: modified_base
<222> LOCATION: 22
<223> OTHER INFORMATION: um2'O-methyl uridine modification
      phosphorothioate linkage
<220> FEATURE:
<221> NAME/KEY: misc_feature
<222> LOCATION: 23
<223> OTHER INFORMATION: n = guanosine phosphorothioate linkage

<400> SEQUENCE: 263
acugaaccaa ggcuuguaaa gun                                      23

<210> SEQ ID NO 264
<211> LENGTH: 23
<212> TYPE: RNA
<213> ORGANISM: Artificial Sequence
<220> FEATURE:
<223> OTHER INFORMATION: Synthetically generated siRNA
<220> FEATURE:
<221> NAME/KEY: modified_base
<222> LOCATION: 21
<223> OTHER INFORMATION: cm = 2'O-methyl cytidine modification
<220> FEATURE:
<221> NAME/KEY: modified_base
<222> LOCATION: 22
<223> OTHER INFORMATION: cm = 2'O-methyl cytidine modification
      phosphorothioate linkage
<220> FEATURE:
<221> NAME/KEY: misc_feature
<222> LOCATION: 23
<223> OTHER INFORMATION: n = adenine phosphorothioate linkage

<400> SEQUENCE: 264
gcccauauuu gucacaaacu ccn                                      23

<210> SEQ ID NO 265
<211> LENGTH: 25
<212> TYPE: DNA
<213> ORGANISM: Artificial Sequence
<220> FEATURE:
<223> OTHER INFORMATION: Probe sequence
```

```
<400> SEQUENCE: 265
gaactgtgtg tgagaggtcc ttctt                                          25

<210> SEQ ID NO 266
<211> LENGTH: 28
<212> TYPE: DNA
<213> ORGANISM: Artificial Sequence
<220> FEATURE:
<223> OTHER INFORMATION: Probe sequence

<400> SEQUENCE: 266
gtgatcagac tcaatacgaa ttcttctt                                       28

<210> SEQ ID NO 267
<211> LENGTH: 27
<212> TYPE: DNA
<213> ORGANISM: Artificial Sequence
<220> FEATURE:
<223> OTHER INFORMATION: Probe sequence

<400> SEQUENCE: 267
gtcatcacac tgaataccaa ttcttct                                        27

<210> SEQ ID NO 268
<211> LENGTH: 27
<212> TYPE: DNA
<213> ORGANISM: Artificial Sequence
<220> FEATURE:
<223> OTHER INFORMATION: Probe sequence

<400> SEQUENCE: 268
aggtgtatgg cttcaaccct gtcttct                                        27

<210> SEQ ID NO 269
<211> LENGTH: 28
<212> TYPE: DNA
<213> ORGANISM: Artificial Sequence
<220> FEATURE:
<223> OTHER INFORMATION: Probe sequence

<400> SEQUENCE: 269
aaacaccatt gtcacactcc atcttctt                                       28

<210> SEQ ID NO 270
<211> LENGTH: 28
<212> TYPE: DNA
<213> ORGANISM: Artificial Sequence
<220> FEATURE:
<223> OTHER INFORMATION: Probe sequence

<400> SEQUENCE: 270
gagctacagt gcttcatctc atcttctt                                       28

<210> SEQ ID NO 271
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine cholesterol conjugated

<400> SEQUENCE: 271
gugaucagac ugaauacgaa n                                              21
```

-continued

```
<210> SEQ ID NO 272
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 21
<223> OTHER INFORMATION: cm =  2'O-methyl  cytidine modification
<220> FEATURE:
<221> NAME/KEY: modified_base
<222> LOCATION: 22
<223> OTHER INFORMATION: am =  =  2'O-methyl  adenine modification
      phosphorothioate linkage
<220> FEATURE:
<221> NAME/KEY: misc_feature
<222> LOCATION: 23
<223> OTHER INFORMATION: n = cytidine phosphorothioate linkage

<400> SEQUENCE: 272
auucguauug agucugauca can                                            23

<210> SEQ ID NO 273
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkage

<400> SEQUENCE: 273
gaacugugug ugagaggucc n                                              21

<210> SEQ ID NO 274
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 22
<223> OTHER INFORMATION: gm = 2'O-methyl guanosine modification
      phosphorothioate linkage
<220> FEATURE:
<221> NAME/KEY: modified_base
<222> LOCATION: 23
<223> OTHER INFORMATION: cm =  2'O-methyl  cytidine modification
      phosphorothioate linkage

<400> SEQUENCE: 274
aggaccucuc acacacaguu cgc                                            23

<210> SEQ ID NO 275
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine phosphorothioate linkage

<400> SEQUENCE: 275
gucaucacac ugaauaccaa n                                              21
```

-continued

```
<210> SEQ ID NO 276
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 21
<223> OTHER INFORMATION: cm =  2'O-methyl  cytidine modification
<220> FEATURE:
<221> NAME/KEY: modified_base
<222> LOCATION: 22
<223> OTHER INFORMATION: am = 2'O-methyl  adenine modification
<220> FEATURE:
<221> NAME/KEY: misc_feature
<222> LOCATION: 23
<223> OTHER INFORMATION: n = cytidine  phosphorothioate linkage

<400> SEQUENCE: 276
auugguauuc agugugauga can                                             23

<210> SEQ ID NO 277
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 21
<223> OTHER INFORMATION: n = uridine cholesterol conjugated to the
      3'-end via a pyrrolidine linker

<400> SEQUENCE: 277
gaacugugug ugagaggucc n                                               21

<210> SEQ ID NO 278
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 21
<223> OTHER INFORMATION: cm =  2'O-methyl  cytidine modification
<220> FEATURE:
<221> NAME/KEY: modified_base
<222> LOCATION: 22
<223> OTHER INFORMATION: gm = 2'O-methyl guanosine modification
<220> FEATURE:
<221> NAME/KEY: misc_feature
<222> LOCATION: 23
<223> OTHER INFORMATION: n = cytidine phosphorothioate linkage

<400> SEQUENCE: 278
aggaccucuc acacacaguu cgn                                             23

<210> SEQ ID NO 279
<211> LENGTH: 31
<212> TYPE: DNA
<213> ORGANISM: Artificial Sequence
<220> FEATURE:
<223> OTHER INFORMATION: Primer

<400> SEQUENCE: 279
ctctagagcg actggagcac gaggacactg a                                    31

<210> SEQ ID NO 280
<211> LENGTH: 34
<212> TYPE: DNA
```

```
<213> ORGANISM: Artificial Sequence
<220> FEATURE:
<223> OTHER INFORMATION: Primer

<400> SEQUENCE: 280
ctctagaggg acactgacat ggactgaagg agta                              34

<210> SEQ ID NO 281
<211> LENGTH: 24
<212> TYPE: DNA
<213> ORGANISM: Artificial Sequence
<220> FEATURE:
<223> OTHER INFORMATION: Primer

<400> SEQUENCE: 281
ctcctgttgc agtagagtgc agct                                         24

<210> SEQ ID NO 282
<211> LENGTH: 38
<212> TYPE: DNA
<213> ORGANISM: Artificial Sequence
<220> FEATURE:
<223> OTHER INFORMATION: Primer

<400> SEQUENCE: 282
acgcgtcgac gtgggagcat ggaggttggc agttgttc                          38

<210> SEQ ID NO 283
<211> LENGTH: 36
<212> TYPE: DNA
<213> ORGANISM: Artificial Sequence
<220> FEATURE:
<223> OTHER INFORMATION: Primer

<400> SEQUENCE: 283
acgcgtcgac gtaatggtgc tgtcatgact gccctt                            36

<210> SEQ ID NO 284
<211> LENGTH: 32
<212> TYPE: DNA
<213> ORGANISM: Artificial Sequence
<220> FEATURE:
<223> OTHER INFORMATION: Primer

<400> SEQUENCE: 284
ctctagagca tggactgaag gagtagaaag aa                                32

<210> SEQ ID NO 285
<211> LENGTH: 21
<212> TYPE: RNA
<213> ORGANISM: Artificial Sequence
<220> FEATURE:
<223> OTHER INFORMATION: Synthetically generated iRNA
<220> FEATURE:
<221> NAME/KEY: misc_feature
<222> LOCATION: 21
<223> OTHER INFORMATION: n = uridine cholesterol conjugated to the
      3'-end via a pyrrolidine linker lacking a
      phosphorothioate

<400> SEQUENCE: 285
gucaucacac ugaauaccaa n                                            21

<210> SEQ ID NO 286
<211> LENGTH: 23
<212> TYPE: RNA
<213> ORGANISM: Artificial Sequence
<220> FEATURE:
```

```
<223> OTHER INFORMATION: Synthetically generated iRNA
<220> FEATURE:
<221> NAME/KEY: modified_base
<222> LOCATION: 21
<223> OTHER INFORMATION: um = 2'O-methyl uridine modification
<220> FEATURE:
<221> NAME/KEY: modified_base
<222> LOCATION: 22
<223> OTHER INFORMATION: cm = 2'O-methyl cytidine modification

<400> SEQUENCE: 286
caggguugaa gccauacacc ucu                                                23

<210> SEQ ID NO 287
<211> LENGTH: 21
<212> TYPE: RNA
<213> ORGANISM: Artificial Sequence
<220> FEATURE:
<223> OTHER INFORMATION: Synthetically generated iRNA
<220> FEATURE:
<221> NAME/KEY: modified_base
<222> LOCATION: 3, 4, 7, 8, 13, 19
<223> OTHER INFORMATION: um = 2'O-methyl uridine modification
<220> FEATURE:
<221> NAME/KEY: modified_base
<222> LOCATION: 17
<223> OTHER INFORMATION: cm = 2'O-methyl cytidine modification
<220> FEATURE:
<221> NAME/KEY: misc_feature
<222> LOCATION: 21
<223> OTHER INFORMATION: n = cytidine cholesterol conjugated to the
      3'-end via a pyrrolidine linker comprising a
      phosphorothioate

<400> SEQUENCE: 287
gauugauuga ccuguccauu n                                                  21

<210> SEQ ID NO 288
<211> LENGTH: 23
<212> TYPE: RNA
<213> ORGANISM: Artificial Sequence
<220> FEATURE:
<223> OTHER INFORMATION: Synthetically generated iRNA
<220> FEATURE:
<221> NAME/KEY: modified_base
<222> LOCATION: 4
<223> OTHER INFORMATION: um = 2'O-methyl uridine modification
<220> FEATURE:
<221> NAME/KEY: modified_base
<222> LOCATION: 8, 17, 21
<223> OTHER INFORMATION: cm = 2'O-methyl cytidine modification
<220> FEATURE:
<221> NAME/KEY: modified_base
<222> LOCATION: 22
<223> OTHER INFORMATION: um = 2'O-methyl uridine modification
      phosphorothioate linkage
<220> FEATURE:
<221> NAME/KEY: misc_feature
<222> LOCATION: 23
<223> OTHER INFORMATION: n = uridine phosphorothioate linkage

<400> SEQUENCE: 288
gaauggacag gucaaucaau cun                                                23

<210> SEQ ID NO 289
<211> LENGTH: 21
<212> TYPE: RNA
<213> ORGANISM: Artificial Sequence
<220> FEATURE:
<223> OTHER INFORMATION: Synthetically generated iRNA
<220> FEATURE:
<221> NAME/KEY: misc_feature
<222> LOCATION: 21
<223> OTHER INFORMATION: n = cytidine cholesterol conjugated to the
```

3'-end via a pyrrolidine linker comprising a
        phosphorothioate

<400> SEQUENCE: 289
gauugauuga ccuguccauu n                                              21

<210> SEQ ID NO 290
<211> LENGTH: 23
<212> TYPE: RNA
<213> ORGANISM: Artificial Sequence
<220> FEATURE:
<223> OTHER INFORMATION: Synthetically generated iRNA
<220> FEATURE:
<221> NAME/KEY: modified_base
<222> LOCATION: 21
<223> OTHER INFORMATION: cm = 2'O-methyl  cytidine modification
<220> FEATURE:
<221> NAME/KEY: modified_base
<222> LOCATION: 22
<223> OTHER INFORMATION: um = 2'O-methyl uridine modification
        phosphorothioate linkage
<220> FEATURE:
<221> NAME/KEY: misc_feature
<222> LOCATION: 23
<223> OTHER INFORMATION: n = uridine phosphorothioate linkage

<400> SEQUENCE: 290
gaauggacag gucaaucaau cun                                            23

<210> SEQ ID NO 291
<211> LENGTH: 21
<212> TYPE: RNA
<213> ORGANISM: Artificial Sequence
<220> FEATURE:
<223> OTHER INFORMATION: Synthetically generated iRNA
<220> FEATURE:
<221> NAME/KEY: modified_base
<222> LOCATION: 1, 4, 14
<223> OTHER INFORMATION: cm =  2'O-methyl  cytidine modification
<220> FEATURE:
<221> NAME/KEY: modified_base
<222> LOCATION: 8, 11
<223> OTHER INFORMATION: um = 2'O-methyl uridine modification
<220> FEATURE:
<221> NAME/KEY: misc_feature
<222> LOCATION: 21
<223> OTHER INFORMATION: n = cytidine cholesterol conjugated to the
        3'-end via a pyrrolidine linker comprising a
        phosphorothioate

<400> SEQUENCE: 291
caccaacuuc uuccacgagu n                                              21

<210> SEQ ID NO 292
<211> LENGTH: 23
<212> TYPE: RNA
<213> ORGANISM: Artificial Sequence
<220> FEATURE:
<223> OTHER INFORMATION: Synthetically generated iRNA
<220> FEATURE:
<221> NAME/KEY: modified_base
<222> LOCATION: 7, 16, 17, 20
<223> OTHER INFORMATION: um = 2'O-methyl uridine modification
<220> FEATURE:
<221> NAME/KEY: modified_base
<222> LOCATION: 21
<223> OTHER INFORMATION: gm = 2'O-methyl guanosine modification
<220> FEATURE:
<221> NAME/KEY: modified_base
<222> LOCATION: 22
<223> OTHER INFORMATION: um = 2'O-methyl uridine modification
        phosphorothioate linkage
<220> FEATURE:
<221> NAME/KEY: misc_feature

```
<222> LOCATION: 23
<223> OTHER INFORMATION: n = uridine phosphorothioate linkage

<400> SEQUENCE: 292
gacucgugga agaaguuggu gun                                              23

<210> SEQ ID NO 293
<211> LENGTH: 21
<212> TYPE: RNA
<213> ORGANISM: Artificial Sequence
<220> FEATURE:
<223> OTHER INFORMATION: Synthetically generated iRNA
<220> FEATURE:
<221> NAME/KEY: misc_feature
<222> LOCATION: 21
<223> OTHER INFORMATION: n = cytidine cholesterol conjugated to the
      3'-end via a pyrrolidine linker comprising a
      phosphorothioate

<400> SEQUENCE: 293
caccaacuuc uuccacgagu n                                                21

<210> SEQ ID NO 294
<211> LENGTH: 23
<212> TYPE: RNA
<213> ORGANISM: Artificial Sequence
<220> FEATURE:
<223> OTHER INFORMATION: Synthetically generated iRNA
<220> FEATURE:
<221> NAME/KEY: modified_base
<222> LOCATION: 21
<223> OTHER INFORMATION: gm = 2'O-methyl guanosine modification
<220> FEATURE:
<221> NAME/KEY: modified_base
<222> LOCATION: 22
<223> OTHER INFORMATION: um = 2'O-methyl uridine modification
      phosphorothioate linkage
<220> FEATURE:
<221> NAME/KEY: misc_feature
<222> LOCATION: 23
<223> OTHER INFORMATION: n = uridine phosphorothioate linkage

<400> SEQUENCE: 294
gacucgugga agaaguuggu gun                                              23

<210> SEQ ID NO 295
<211> LENGTH: 21
<212> TYPE: RNA
<213> ORGANISM: Artificial Sequence
<220> FEATURE:
<223> OTHER INFORMATION: Synthetically generated iRNA
<220> FEATURE:
<221> NAME/KEY: modified_base
<222> LOCATION: 4, 5, 6, 8, 15, 17
<223> OTHER INFORMATION: um = 2'O-methyl uridine modification
<220> FEATURE:
<221> NAME/KEY: modified_base
<222> LOCATION: 11
<223> OTHER INFORMATION: cm =  2'O-methyl  cytidine modification
<220> FEATURE:
<221> NAME/KEY: misc_feature
<222> LOCATION: 21
<223> OTHER INFORMATION: n = cytidine  phosphorothioate linkage

<400> SEQUENCE: 295
gaguuuguga caaauauggg n                                                21

<210> SEQ ID NO 296
<211> LENGTH: 23
<212> TYPE: RNA
<213> ORGANISM: Artificial Sequence
<220> FEATURE:
```

```
<223> OTHER INFORMATION: Synthetically generated iRNA
<220> FEATURE:
<221> NAME/KEY: modified_base
<222> LOCATION: 4, 13, 15, 21
<223> OTHER INFORMATION: cm =  2'O-methyl  cytidine modification
<220> FEATURE:
<221> NAME/KEY: modified_base
<222> LOCATION: 6, 8, 9, 10,
<223> OTHER INFORMATION: um = 2'O-methyl uridine modification
<220> FEATURE:
<221> NAME/KEY: modified_base
<222> LOCATION: 22
<223> OTHER INFORMATION: cm =  2'O-methyl  cytidine modification
      phosphorothioate linkage
<220> FEATURE:
<221> NAME/KEY: misc_feature
<222> LOCATION: 23
<223> OTHER INFORMATION: n = adeninephosphorothioate linkage

<400> SEQUENCE: 296
gcccauauuu gucacaaacu ccn                                                 23

<210> SEQ ID NO 297
<211> LENGTH: 21
<212> TYPE: RNA
<213> ORGANISM: Artificial Sequence
<220> FEATURE:
<223> OTHER INFORMATION: Synthetically generated iRNA
<220> FEATURE:
<221> NAME/KEY: misc_feature
<222> LOCATION: 21
<223> OTHER INFORMATION: n = cytidine phosphorothioate linkage

<400> SEQUENCE: 297
gaguuuguga caaauauggg n                                                   21
```

RNAI MODULATION OF APOB AND USES THEREOF

CROSS-REFERENCE TO RELATED APPLICATIONS

This application is a divisional application of U.S. patent application Ser. No. 12/400,744, filed Mar. 9, 2009, which is divisional application of U.S. patent application Ser. No. 11/235,385, filed Sep. 26, 2005, now issued as U.S. Pat. No. 7,528,118, and which claims priority to U.S. Provisional Application Ser. No. 60/613,141, filed Sep. 24, 2004, which is incorporated herein by reference in its entirety.

SEQUENCE LISTING

In accordance with 37 C.F.R. §1.821(c), this application is filed with an electronically submitted Sequence Listing in ASCII text format (68 kb), entitled "16562_US_Sequence_Listing," created on Mar. 19, 2010. This Sequence Listing is hereby incorporated by reference, in its entirety and for all purposes.

TECHNICAL FIELD

The invention relates to compositions and methods for modulating the expression of apolipoprotein B, and more particularly to the downregulation of apolipoprotein B by oligonucleotides, e.g., chemically modified oligonucleotides.

BACKGROUND

RNA interference or "RNAi" is a term initially coined by Fire and co-workers to describe the observation that double-stranded RNA (dsRNA) can block gene expression when it is introduced into worms (Fire et al., Nature 391:806-811, 1998). Short dsRNA directs gene-specific, post-transcriptional silencing in many organisms, including vertebrates, and has provided a new tool for studying gene function.

Lipoproteins consist of acylglycerols and cholesteryl esters surrounded by an amphiphilic coating of protein, phospholipid and cholesterol. The protein components of lipoproteins are known as apolipoproteins, and at least nine apolipoproteins exist in humans. Apolipoprotein B (ApoB) is found in various classes of lipoproteins: chylomicrons, very low density lipoproteins (VLDL), intermittent density lipoproteins (IDL), and low density lipoproteins (LDL). ApoB functions as a recognition signal for the cellular binding and internalization of LDL particles by the ApoB/E receptor. An accumulation or overabundance of apolipoprotein B-containing lipoproteins can lead to lipid-related disorders such as atherosclerosis.

The development of therapies that reduce ApoB can be useful for treating lipid-related disorders. One oligonucleotide based therapy, in the form of antisense therapy, has been shown to reduce ApoB levels in mouse in vivo, and treatments subsequently reduced serum cholesterol and triglyceride levels (U.S. Publication No. 2003/0215943). These results demonstrated a moderate downregulation of ApoB and its use as a target in treating lipid-related disorders. The present invention advances the art by providing IRNA agents that have been shown to reduce serum ApoB levels in vivo.

SUMMARY

The invention provides compositions and methods for reducing apolipoprotein B (ApoB) levels in a subject, e.g., a mammal, such as a human. The method includes administering to a subject an iRNA agent that silences an ApoB gene. The iRNA agent can be one described here, or can be a dsRNA that is based on one of the active sequences and target an identical region of the ApoB gene, e.g., a mammalian ApoB gene, such as an ApoB gene from a human or mouse. The iRNA agent can comprise less than 30 nucleotides per strand, e.g., 21-23 nucleotides and consist of, comprise or be derived from one of the agents provided herein under agent numbers 1-74. These preferred iRNA agents include four or more nucleotide mismatches to all non-ApoB gene sequences in the subject.

The invention specifically provides an iRNA agent that includes a sense strand having at least 15 contiguous nucleotides of the sense strand sequences, and an antisense strand having at least 15 contiguous nucleotides of the antisense sequences, of the iRNA agents provided herein under agent numbers 1-74, e.g. agent number 1, sense strand sequence 5'-cuuuacaagccuugguucagu-3' (SEQ. ID NO. 153), antisense strand sequence 5'-acugaaccaaggcuuguaaagug-3'. (SEQ. ID No. 154)

It shall be understood that, while some of the iRNA agents provided herein encompass specific preferred patterns of modified nucleotides, e.g. agent numbers 54 to 74, the iRNA agents of agent numbers 1-53 are provided as blueprints. They are meant to encompass such modifications as are evident to the skilled person as equivalent to the iRNA agents of agent numbers 1-53, such as are further described below, e.g. 2'-O-methyl modifications, generic base substitutions, etc, that the skilled person would not expect to alter the properties of these agents, and specifically the ability of the two strands to hybridize under stringent conditions with their complementary counterparts.

TABLE 1

Exemplary iRNA agents to target ApoB

| SEQ. ID No. | Sequence sense strand[a] | SEQ. ID No. | Sequence antisense strand[a] | Duplex descriptor[a] | Agent number |
|---|---|---|---|---|---|
| 153 | cuuuacaagccuugguucagu | 154 | acugaaccaaggcuuguaaagug | AL-DUP 5097 | 1 |
| 155 | ggaaucuuauauuugauccaa | 156 | uuggaucaaauauaagauucccu | AL-DUP 5098 | 2 |
| 161 | uagaagggaaucuuauauuug | 162 | caaauauaagauucccuucuauu | AL-DUP 5101 | 3 |
| 147 | gccccaucacuuuacaagccu | 148 | aggcuuguaaagugauggggcug | AL-DUP 5094 | 4 |
| 159 | aaauagaagggaaucuuauau | 160 | auauaagauucccuucuauuuug | AL-DUP 5100 | 5 |

TABLE 1-continued

Exemplary iRNA agents to target ApoB

| SEQ. ID No. | Sequence sense strand[a] | SEQ. ID No. | Sequence antisense strand[a] | Duplex descriptor[a] | Agent number |
|---|---|---|---|---|---|
| 145 | ucacauccuccaguggcugaa | 146 | uucagccacuggaggaugugagu | AL-DUP 5093 | 6 |
| 49 | agguguauggcuucaacccug | 50 | caggguugaagccauacaccucu | AL-DUP 5024 | 7 |
| 127 | cugaacaucaagaggggcauc | 128 | gaugcccucuugauguucagga | AL-DUP 5084 | 8 |
| 137 | gaguuugugacaaauaugggc | 138 | gcccauauuugucacaaacucca | AL-DUP 5089 | 9 |
| 93 | aucaagugucaucacacugaa | 94 | uucagugugaugacacuugauuu | AL-DUP 5046 | 10 |
| 97 | gucaucacacugaauaccaau | 98 | auugguauucagugugaugacac | AL-DUP 5048 | 11 |
| 95 | ucaagugucaucacacugaau | 96 | auucagugugaugacacuugauu | AL-DUP 5047 | 12 |
| 99 | cuguccauucaaaacuaccac | 100 | gugguaguuugaauggacaggu | AL-DUP 5049 | 13 |
| 129 | ugaacaucaagaggggcauca | 130 | ugaugcccucuugauguucagg | AL-DUP 5085 | 14 |
| 135 | agccccaucacuuuacaagcc | 136 | ggcuuguaaagugauggggcugg | AL-DUP 5088 | 15 |
| 131 | guccagccccaucacuuuaca | 132 | uguaaagugauggggcuggacac | AL-DUP 5086 | 16 |
| 27 | gguguauggcuucaacccuga | 28 | ucagggguugaagccauacaccuc | AL-DUP 5013 | 17 |
| 107 | gaccuguccauucaaaacuac | 108 | guaguuugaauggacaggucaa | AL-DUP 5053 | 18 |
| 143 | auugggaagaagaggcagcuu | 144 | aagcugccucuucuucccaauua | AL-DUP 5092 | 19 |
| 123 | uaacacuaagaaccagaagau | 124 | aucuucgguucuuaguguuagc | AL-DUP 5061 | 20 |
| 57 | gaggguguauggcuucaacccu | 58 | agggguugaagccauacaccucuu | AL-DUP 5028 | 21 |
| 41 | guguauggcuucaacccugag | 42 | cucagggguugaagccauacaccu | AL-DUP 5020 | 22 |
| 157 | gaagggaaucuuauauuugau | 158 | aucaaauauaagauucccuucua | AL-DUP 5099 | 23 |
| 59 | uggcuucaacccugagggcaa | 60 | uugcccucagggguugaagccaua | AL-DUP 5029 | 24 |
| 63 | guauggcuucaacccugaggg | 64 | cccucagggguugaagccauacac | AL-DUP 5031 | 25 |
| 121 | caagugucaucacacugaaua | 122 | uauucagugugaugacacuugau | AL-DUP 5060 | 26 |
| 55 | uaaaucaagugucaucacacu | 56 | agugugaugacacuugauuuaaa | AL-DUP 5027 | 27 |
| 39 | gugacaaauaugggcaucauc | 40 | gaugaugcccauauuugucacaa | AL-DUP 5019 | 28 |
| 71 | caccaacuucuuccacgaguc | 72 | gacucguggaagaaguuggguguu | AL-DUP 5035 | 29 |
| 73 | gaugaacaccaacuucuucca | 74 | uggaagaaguuggguguucaucug | AL-DUP 5036 | 30 |
| 105 | accguccauucaaaacuacc | 106 | gguaguuugaauggacagguca | AL-DUP 5052 | 31 |
| 61 | gaacaccaacuucuuccacga | 62 | ucguggaagaaguuggguguucau | AL-DUP 5030 | 32 |
| 45 | gauaccguguauggaaacugc | 46 | gcaguuuccauacacgguaucca | AL-DUP 5022 | 33 |
| 133 | cagccccaucacuuuacaagc | 134 | gcuuguaaagugauggggcugga | AL-DUP 5087 | 34 |
| 5 | gauugauugaccuguccauuc | 6 | gaauggacaggucaaucaaucuu | AL-DUP 5002 | 35 |
| 77 | agaugaacaccaacuucuuccc | 78 | ggaagaaguuggguguucaucugg | AL-DUP 5038 | 36 |
| 1 | aagccuugguucaguguggac | 2 | guccacacugaaccaaggcuugu | AL-DUP 5000 | 37 |
| 117 | ucaucacacugaauaccaaug | 118 | cauugguauucagugugaugaca | AL-DUP 5058 | 38 |
| 3 | ugaacaccaacuucuuccacg | 4 | cguggaagaaguuggguguucauc | AL-DUP 5001 | 39 |
| 69 | acaccaacuucuuccacgagu | 70 | acucguggaagaaguuggguguuc | AL-DUP 5034 | 40 |
| 25 | ugauugaccuguccauucaaa | 26 | uuugaauggacaggucaaucaau | AL-DUP 5012 | 41 |
| 21 | caaauggacucaucugcuaca | 22 | uguagcagaugaguccauuugga | AL-DUP 5010 | 42 |

TABLE 1-continued

Exemplary iRNA agents to target ApoB

| SEQ. ID No. | Sequence sense strand[a] | SEQ. ID No. | Sequence antisense strand[a] | Duplex descriptor[a] | Agent number |
|---|---|---|---|---|---|
| 29 | ucugugggauuccaucugcca | 30 | uggcagauggaaucccacagacu | AL-DUP 5014 | 43 |
| 109 | caucacacugaauaccaaugc | 110 | gcauugguauucagugugaugac | AL-DUP 5054 | 44 |
| 23 | gauugaccuguccauucaaaa | 24 | uuuugaauggacaggucaaucaa | AL-DUP 5011 | 45 |
| 33 | acaauuugaucaguauauuaa | 34 | uuaauauacugaucaaauuguau | AL-DUP 5016 | 46 |
| 83 | acaagccuugguucagugugg | 84 | ccacacugaaccaaggcuuguaa | AL-DUP 5041 | 47 |
| 79 | auuccaucugccaucucgaga | 80 | ucucgagauggcagauggaaucc | AL-DUP 5039 | 48 |
| 43 | uaccguguauggaaacugcuc | 44 | gagcaguuuccauacacgguauc | AL-DUP 5021 | 49 |
| 35 | ggacucaucugcuacagcuua | 36 | uaagcuguagcagaugagaccau | AL-DUP 5017 | 50 |
| 51 | guuugugacaaauaugggcau | 52 | augcccauauuugucacaaacuc | AL-DUP 5025 | 51 |
| 65 | auggcuucaacccugagggca | 66 | ugcccucaggguugaagccauac | AL-DUP 5032 | 52 |
| 125 | caauuugaucaguauauuaaa | 126 | uuuaauauacugaucaaauugua | AL-DUP 5062 | 53 |

[a]See Table 2 for an explanation of nucleotide representation (e.g., lower case letters, bold and italicized letters).

As shown in Example 3 hereinbelow, the iRNA agents of Table 1, agent numbers 1-53, possess the advantageous and surprising ability to reduce the amount of ApoB mRNA present in cultured human HepG2 cells after incubation with these iRNA agents by more than 50% compared to cells which have not been incubated with the iRNA agent, and/or to reduce the amount of ApoB protein secreted into cell culture supernatant by cultured human HepG2 cells by more than 50% (see Table 8).

The invention further provides an iRNA agent that includes a sense strand having at least 15 contiguous nucleotides of the sense sequences of the iRNA agents, agent numbers 1-19, 24-26, 29, 30 and 32-42, and an antisense strand having at least 15 contiguous nucleotides of the antisense sequences of the iRNA agents, agent numbers 1-19, 24-26, 29, 30 and 32-42. As shown in Example 3 hereinbelow, the iRNA agents, agent numbers 1-19, 24-26, 29, 30 and 32-42, possess the advantageous and surprising ability to reduce the amount of ApoB mRNA present in cultured human HepG2 cells after incubation with these iRNA agents by more than 60% compared to cells which have not been incubated with the iRNA agent, and/or to reduce the amount of ApoB protein secreted into cell culture supernatant by more than 60% (see Table 8).

The invention further provides an iRNA agent that includes a sense strand having at least 15 contiguous nucleotides of the sense sequences of the agents provided in Table 1, agent numbers 1-12, 15, 17, 24, 29, 30 and 32-35, and an antisense strand having at least 15 contiguous nucleotides of the antisense sequences of the agents provided in Table 1, agent numbers 1-12, 15, 17, 24, 29, 30 and 32-35. As shown in Example 3 hereinbelow, these iRNA agents possess the advantageous and surprising ability to reduce the amount of ApoB mRNA present in cultured human HepG2 cells after incubation with these agents by more than 70% compared to cells which have not been incubated with the agent, and/or to reduce the amount of ApoB protein secreted into cell culture supernatant by more than 70% (see Table 8).

The invention further provides an iRNA agent that includes a sense strand having at least 15 contiguous nucleotides of the sense sequences of the iRNA agents, agent numbers 1-5, 7, and 11, and an antisense strand having at least 15 contiguous nucleotides of the antisense sequences of the iRNA agents, agent numbers 1-5, 7, and 11. As shown in Example 3 hereinbelow, these iRNA agents possess the advantageous and surprising ability to reduce the amount of ApoB mRNA present in cultured human HepG2 cells after incubation with these agents by more than 80% compared to cells which have not been incubated with the agent, and/or to reduce the amount of ApoB protein secreted into cell culture supernatant by more than 80% (see Table 8).

In a particularly preferred aspect, the iRNA agent is selected from the group of: the iRNA agent, agent number 54, 55, 56, 57, 58, 59, 60, 61, 62, 63, 64, 65, 66, 67, 68, 69, 70, 71, 72, 73, or 74.

In another preferred embodiment, the iRNA agent reduces the amount of ApoB mRNA present in cultured human HepG2 cells after incubation with the iRNA agent by more than 50% compared to cells which have not been incubated with the agent, and/or reduces the amount of ApoB protein secreted into cell culture supernatant by cultured human HepG2 cells by more than 50%, and/or reduces the amount of apo-B mRNA present in murine liver cells of C57Bl/6 mice by at least 20% in vivo after administration of 50 mg/kg body weight or 100 mg/kg body weight.

Further provided by the instant invention are iRNA agents comprising a sense strand and antisense strand each comprising a sequence of at least 16, 17 or 18 nucleotides which is essentially identical, as defined below, to one of the sequences of the iRNA agents, agent numbers 1-74, except that not more than 1, 2 or 3 nucleotides per strand, respectively, have been substituted by other nucleotides (e.g. adenosine replaced by uracil), while essentially retaining the ability to inhibit ApoB expression in cultured human HepG2 cells, as defined below.

In one embodiment, the iRNA agent is at least 15 nucleotides long and includes a sense RNA strand and an antisense RNA strand, wherein the antisense RNA strand is 30 or fewer nucleotides in length, and the duplex region of the iRNA agent is 15-30, preferably 18-25 nucleotide pairs in length.

The iRNA agent may further include a nucleotide overhang having 1 to 4, preferably 2 to 3, unpaired nucleotides, and the unpaired nucleotides may have at least one phosphorothioate dinucleotide linkage. The nucleotide overhang can be, e.g., at the 3'-end of the antisense strand of the iRNA agent.

In one embodiment, the iRNA agent inhibits the expression of human and mouse ApoB, e.g. in human HepG2 and mouse NmuLi cells.

In one embodiment, and as described herein, it is preferred that the IRNA agent be modified by attachment of a hydrophobic moiety, e.g. a cholesterol-comprising moiety, preferably to the sense strand of the iRNA agent, and more preferably to the 3'-end of the sense strand of the iRNA agent.

In another embodiment, and as described herein, it is preferred that the iRNA agent be modified to improve stability. Preferred modifications are the introduction of phosphorothioate linkages and 2'-substitutions on the ribose unit, e.g., 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) substitutions.

Preferably, these 2'-substitutions are made to the 5' nucleotide of a 5'-UA-3' dinucleotide, a 5'-UG-3' dinucleotide, a 5'-CA-3' dinucleotide, a 5'-UU-3' dinucleotide, or a 5'-CC-3' dinucleotide on the sense strand and, optionally, also on the antisense strand of the iRNA agent, or to all pyrimidine-base comprising nucleotides. More, preferably, the 5'-most pyrimidines in all occurrences of the sequence motifs 5'-UA-3', 5'-CA-3',5'-UU-3', and 5'-UG-3' are 2'-modified nucleotides. Yet more preferably, all pyrimidines in the sense strand are 2'-modified nucleotides, and the 5'-most pyrimidines in all occurrences of the sequence motifs 5'-UA-3' and 5'-CA-3'. Most preferably, all pyrimidines in the sense strand are 2'-modified nucleotides, and the 5'-most pyrimidines in all occurrences of the sequence motifs 5'-UA-3',5'-CA-3',5'-UU-3', and 5'-UG-3' are 2'-modified nucleotides in the antisense strand.

In another embodiment, and as described herein, a cholesterol moiety (e.g., on the 3'-end of the sense strand), a 2'-modification (e.g., a 2'-O-methyl or 2'-deoxy-2'-fluoromodification), and a phosphorothioate (e.g., on the 3'-most one or two nucleotides of the sense and antisense strands) are present in the same iRNA agent.

In a preferred embodiment, administration of an iRNA agent, e.g., an iRNA agent described herein, is for treatment of a disease or disorder present in the subject in which ApoB expression plays a role. In another preferred embodiment, administration of the iRNA agent is for prophylactic treatment of ApoB mediated disorders.

In one aspect, the invention features preparations, including substantially pure or pharmaceutically acceptable preparations of iRNA agents which modulate e.g., inhibit, ApoB. The preparations can include an iRNA agent that targets an ApoB encoding nucleic acid and a pharmaceutically acceptable carrier. In one embodiment, the iRNA agent has a sense strand having at least 15 contiguous nucleotides of the sense sequences of the iRNA agents, agent numbers 1-74, and an antisense strand having at least 15 contiguous nucleotides of the antisense sequences of the iRNA agents, agent numbers 1-74.

In another aspect, the invention features a method of preparing a pharmaceutical composition, comprising formulating an iRNA agent a sense strand having at least 15 contiguous nucleotides of the sense sequences of the iRNA agents, agent numbers 1-74, and an antisense strand having at least 15 contiguous nucleotides of the antisense sequences of the iRNA agents, agent numbers 1-74, with a pharmaceutically acceptable carrier.

The pharmaceutical composition of the invention can be administered in an amount sufficient to reduce expression of ApoB messenger RNA (mRNA). In one embodiment, the iRNA agent is administered in an amount sufficient to reduce expression of ApoB protein (e.g., by at least 2%, 4%, 6%, 10%, 15%, 20% or greater).

The pharmaceutical composition of the invention can be administered to a subject, wherein the subject is at risk for or suffering from a disorder characterized by elevated or otherwise unwanted expression of ApoB, elevated or otherwise unwanted levels of cholesterol, a lipid-mediated vascular disorder, and/or disregulation of lipid metabolism. The iRNA agent can be administered to an individual diagnosed with or having the disorder, or at risk for the disorder to delay onset of the disorder or a symptom of the disorder. These disorders include HDL/LDL cholesterol imbalance; dyslipidemias, e.g., familial combined hyperlipidemia (FCHL), acquired hyperlipidemia; hypercholestorolemia; statin-resistant hypercholesterolemia; coronary artery disease (CAD); coronary heart disease (CHD); thrombosis; and atherosclerosis. In one embodiment, the iRNA that targets ApoB is administered to a subject suffering from statin-resistant hypercholesterolemia.

The pharmaceutical composition of the invention can be administered in an amount sufficient to reduce levels of serum LDL cholesterol and/or HDL cholesterol and/or total cholesterol in a subject. For example, the iRNA is administered in an amount sufficient to decrease total cholesterol by at least 0.5%, 1%, 2.5%, 5%, 10% or more in the subject. In one embodiment, the pharmaceutical composition of the invention is administered in an amount sufficient to reduce the risk of myocardial infarction in the subject. In a preferred embodiment the pharmaceutical composition is administered repeatedly.

In one embodiment, the iRNA agent can be targeted to the liver, and ApoB expression levels are decreased in the liver following administration of the ApoB iRNA agent. For example, the iRNA agent can be complexed with a moiety that targets the liver, e.g., an antibody or ligand, such as cholesterol that binds a receptor on liver cells. As shown in Example 7G) below, the conjugation of a cholesterol-comprising moiety led to efficient uptake of siRNAs by liver tissue and decreased ApoB mRNA levels in liver samples. This shows that modifications such as a conjugation with a cholesterol-comprising moiety allows for the use of iRNA agents in vivo to target genes in the liver.

In one embodiment, the iRNA agent can be targeted to the gut, e.g., to the intestine, such as to the jejunum of the intestine, and ApoB expression levels are decreased in the gut following administration of the ApoB iRNA agent. Unexpectedly, it was found that an iRNA agent conjugated to a cholesterol moiety can be used to target an IRNA agent to the gut. As shown in Example 7G) below, the conjugation of a cholesterol-comprising moiety led to efficient uptake of siRNAs by intestinal tissues and decreased ApoB mRNA levels in intestinal tissue samples. This shows that modifications such as a conjugation with a cholesterol-comprising moiety allows for the use of iRNA agents in vivo to target genes in tissues of the gut.

In one embodiment, the iRNA agent has been modified, or is associated with a delivery agent, e.g., a delivery agent described herein, e.g., a liposome. In one embodiment, the modification mediates association with a serum albumin (SA), e.g., a human serum albumin (HSA), or a fragment thereof.

A method of evaluating an iRNA agent thought to inhibit the expression of an ApoB-gene, the method comprising:
   a. providing an iRNA agent, wherein a first strand is sufficiently complementary to a nucleotide sequence of an ApoB mRNA, and a second strand is sufficiently complementary to the first strand to hybridize to the first strand;
   b. contacting the iRNA agent to a cell comprising an ApoB gene;
   c. comparing ApoB gene expression before contacting the iRNA agent to the cell, or of uncontacted control cells, to the ApoB gene expression after contacting the iRNA agent to the cell; and
   d. determining whether the iRNA agent is useful for inhibiting ApoB gene expression, wherein the iRNA is useful if the amount of ApoB RNA present in the cell, or protein secreted by the cell, is less than the amount prior to contacting the iRNA agent to the cell.

In one embodiment, steps b.-d. are performed both in vitro and in non-human laboratory animals in vivo. In another embodiment. he method further comprises determining the activity of the iRNA agent in activating interferon-α production by peripheral blood mononuclear cells.

The methods and compositions of the invention, e.g., the methods and compositions to treat diseases and disorders of the liver described herein, can be used with any of the iRNA agents described. In addition, the methods and compositions of the invention can be used for the treatment of any disease or disorder described herein, and for the treatment of any subject, e.g., any animal, any mammal, such as any human.

The methods and compositions of the invention, e.g., the methods and iRNA compositions to treat lipid metabolism disorders described herein, can be used with any dosage and/or formulation described herein, as well as with any route of administration described herein.

The details of one or more embodiments of the invention are set forth in the accompanying drawings and the description below. Other features, objects, and advantages of the invention will be apparent from this description, the drawings, and from the claims. This application incorporates all cited references, patents, and patent applications by references in their entirety for all purposes.

BRIEF DESCRIPTION OF DRAWINGS

FIG. 6A is an S1-nuclease protection assay with radiolabeled probes complementary to antisense strands of siRNAs. The assay was used to detect siRNAs in pooled liver and jejunum tissue lysates from animals injected with saline ("-"), AL-DUP 5386 ("A"), AL-DUP 5311 ("B"), AL-DUP 5385 ("C2"), and AL-DUP 5167 ("C1"). The three cholesterol-conjugated siRNAs were detected at comparable levels in liver and jejunum, but the non-cholesterol-conjugated siRNA AL-DUP 5385 remained below detection levels in both tissues. S1-nuclease protection assay for endogeneous miRNAs served as a loading controls for jejunum (miRNA 143, sequence 5'-UGAGAUGAAGCACUGUAGCUCA-3', SEQ. ID NO. 270) and liver (miRNA 122, sequence 5'-UGGAGU-GUGACAAUGGUGUUUG-3', SEQ. ID NO. 269).

FIG. 6B is a graph depicting the results of branched-DNA assays to detect ApoB mRNA levels in mouse liver and jejunum tissue following siRNA treatment. Tissue lysates were used for ApoB and GAPDH mRNA quantification and the ratio of ApoB and GAPDH mRNA was calculated and expressed as a group average relative to a saline control group. Bars represent group mean values. Error bars represent the standard deviation of the mean. Asterisks above bars in bar graphs denote groups significantly different compared to saline control animals at $p<0.01$.

FIG. 6C is a graph depicting the results of ELISA assays to measure plasma ApoB protein levels following siRNA treatment. ApoB-100 from plasma samples of individual animals was detected using the primary antibody LF3 against mouse ApoB-100. Mean group values of ApoB protein level are represented relative to the mean of saline control. Bars represent group mean values. Error bars represent the standard deviation of the mean. Asterisks above bars in bar graphs denote groups significantly different compared to saline control animals $p<0.01$.

FIG. 6D is a graph depicting total plasma ApoB protein levels following siRNA treatment. Total plasma cholesterol levels where measured using the Cholesterol detection kit (Diasys). Bars represent group mean values. Error bars represent the standard deviation of the mean. Asterisks above bars in bar graphs denote groups significantly different compared to saline control animals $p<0.01$.

DETAILED DESCRIPTION

Figure 1:
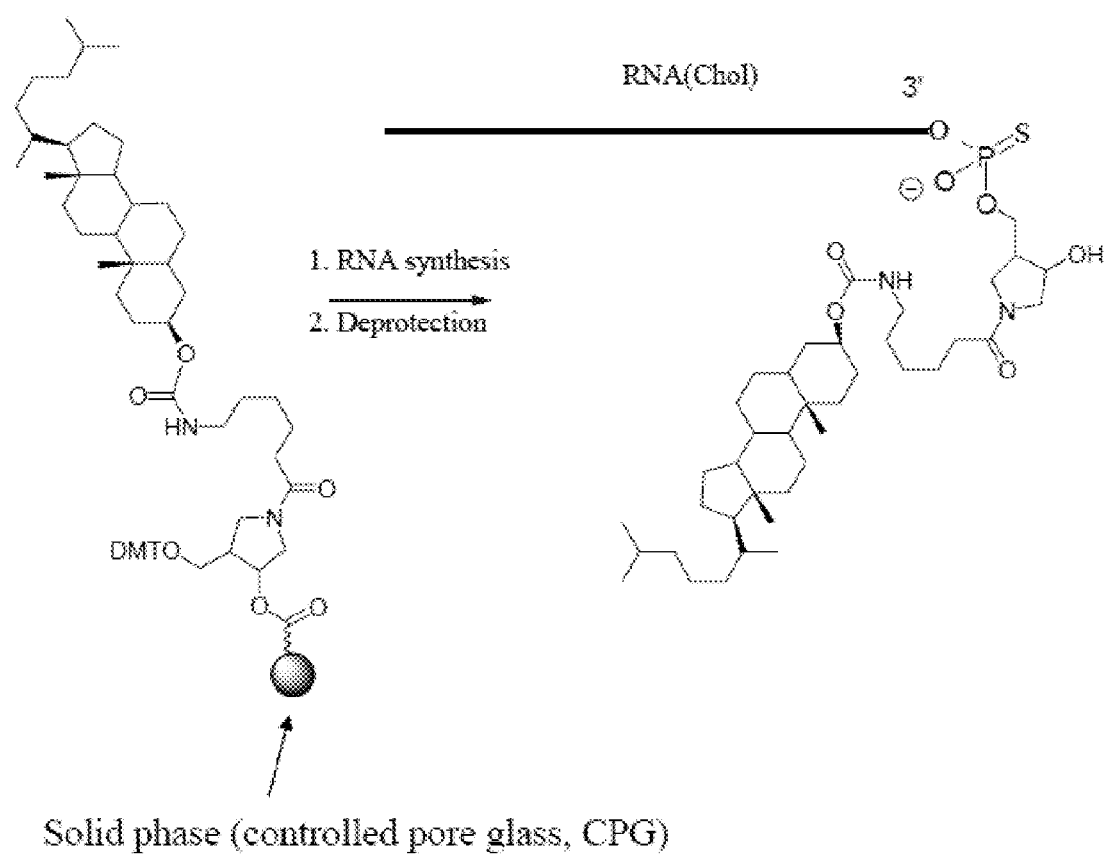
FIG. 1 is a schematic illustrating the synthesis and structure of cholesterol conjugated RNA strands. The sphere represents the solid phase (controlled pore glass, CPG).

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogate, all of which are described herein. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can down-regulate the expression of a target gene, e.g., ApoB. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded (ds) iRNA agent. If the iRNA agent is a single strand it is particularly preferred that it include a 5' modification which includes one or more phosphate groups or one or more analogs of a phosphate group.

A "single strand iRNA agent" as used herein, is an iRNA agent which is made up of a single molecule. It may include a duplexed region, formed by intra-strand pairing, e.g., it may be, or include, a hairpin or panhandle structure. Single strand iRNA agents are preferably antisense with regard to the target molecule.

A "ds iRNA agent" (abbreviation for "double stranded iRNA agent"). as used herein, is an iRNA agent which includes more than one, and preferably two, strands in which interchain hybridization can form a region of duplex structure.

Although, in mammalian cells, long ds iRNA agents can induce the interferon response which is frequently deleterious, short ds iRNA agents do not trigger the interferon response, at least not to an extent that is deleterious to the cell and host. The iRNA agents of the present invention include molecules which are sufficiently short that they do not trigger the interferon response in mammalian cells. Thus, the administration of a composition of an iRNA agent (e.g., formulated as described herein) to a mammalian cell can be used to silence expression of the ApoB gene while circumventing the interferon response. Molecules that are short enough that they do not trigger an interferon response are termed siRNA agents or siRNAs herein. "siRNA agent" or "siRNA" as used herein, refers to an iRNA agent, e.g., a ds iRNA agent or single strand RNA agent, that is sufficiently short that it does not induce a deleterious interferon response in a human cell, e.g., it has a duplexed region of less than 60 but preferably less than 50, 40, or 30 nucleotide pairs.

Moreover, in one embodiment, a mammalian cell is treated with an iRNA agent that disrupts a component of the interferon response, e.g., dsRNA-activated protein kinase PKR.

The isolated iRNA agents described herein, including ds iRNA agents and siRNA agents, can mediate silencing of an ApoB gene, e.g., by RNA degradation. For convenience, such RNA is also referred to herein as the RNA to be silenced. Such a gene is also referred to as a target gene. Preferably, the RNA to be silenced is a gene product of an endogenous ApoB gene.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element. While not wishing to be bound by theory, it is believed that silencing by the agents described herein uses the RNAi machinery or process and a guide RNA, e.g., an siRNA agent of 15 to 30 nucleotide pairs.

As used herein, "the term "complementary" is used to indicate a sufficient degree of complementarity such that stable and specific binding occurs between a compound of the invention and a target RNA molecule, e.g. an ApoB mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA (e.g., a target ApoB mRNA) if the iRNA agent reduces the production of a protein encoded by the target RNA in a cell. The iRNA agent may also be "exactly complementary" (excluding the SRMS containing subunit(s)) to the target RNA, e.g., the target RNA and the iRNA agent anneal, preferably to form a hybrid made exclusively of Watson-Crick basepairs in the region of exact complementarity. A "sufficiently complementary" iRNA agent can include an internal region (e.g., of at least 10 nucleotides) that is exactly complementary to a target ApoB RNA. Moreover, in some embodiments, the iRNA agent specifically discriminates a single-nucleotide difference. In this case, the iRNA agent only mediates RNAi if exact complementary is found in the region (e.g., within 7 nucleotides of) the single-nucleotide difference. Preferred iRNA agents will be based on or consist or comprise the sense and antisense sequences provided in Table 1.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g. adenosine replaced by uracil). "Essentially retaining the ability to inhibit ApoB expression in cultured human HepG2 cells", as used herein referring to an iRNA agent not identical to but derived from one of the iRNA agents of Table 1 by deletion, addition or substitution of nucleotides, means that the derived iRNA agent possesses an inhibitory activity lower by not more than 20% inhibition compared to the iRNA agent of Table 1 it was derived from. E.g. an iRNA agent derived from an iRNA agent of Table 1 which lowers the amount of ApoB mRNA present in cultured human HepG2 cells by 70% may itself lower the amount of ApoB mRNA present in cultured human HepG2 cells by at least 50% in order to be considered as essentially retaining the ability to inhibit ApoB expression in cultured human HepG2 cells. Optionally, an iRNA agent of the invention may lower the amount of ApoB mRNA present in cultured human HepG2 cells, or the amount of ApoB protein secreted into cell culture supernatant, by at least 50%.

In a typical embodiment, the subject is a mammal such as a cow, horse, mouse, rat, dog, pig, goat, or a primate. In a much preferred embodiment, the subject is a human, e.g., a normal individual or an individual that has, is diagnosed with, or is predicted to have a disease or disorder.

Because iRNA agent mediated silencing can persist for several days after administering the iRNA agent composition, in many instances, it is possible to administer the composition with a frequency of less than once per day, or, for some instances, only once for the entire therapeutic regimen.

Disorders Associated with ApoB Misexpression

An iRNA agent that targets ApoB, e.g., an iRNA agent described herein, can be used to treat a subject, e.g., a human having or at risk for developing a disease or disorder associated with aberrant or unwanted ApoB gene expression, e.g., ApoB overexpression.

For example, an iRNA agent that targets ApoB mRNA can be used to treat a lipid-related disorder, such as hypercholesterolemia, e.g., primary hypercholesterolemia with peripheral vascular disease. Other lipid-related disorders include coronary artery disease (CAD), myocardial infarction; HDL/LDL cholesterol imbalance; dyslipidemias (e.g., familial combined hyperlipidemia (FCHL) and acquired hyperlipidemia); hypercholestorolemia; statin-resistant hypercholesterolemia; coronary heart disease (CHD); thrombosis; and atherosclerosis. In one embodiment, the iRNA that targets ApoB mRNA is administered to a subject suffering from statin-resistant disorder, e.g. statin-resistant hypercholesterolemia. The subject can be one who is currently being treated with a statin, one who has been treated with a statin in the past, or one who is unsuited for treatment with a statin.

An iRNA agent targeting ApoB mRNA can be used to treat a human carrying a genetic mutation or polymorphism in the ApoB gene or in the LDL-receptor. For example, the iRNA agent can be used to treat a human diagnosed as having familial ligand-defective apolipoprotein B-100 (FDB), a dominantly inherited disorder of lipoprotein metabolism leading to hypercholesterolemia and increased proneness to CAD. Plasma cholesterol levels are dramatically elevated in these subjects due to impaired clearance of LDL particles by defective ApoB/E receptors.

Design and Selection of iRNA Agents

Example 2 hereinbelow shows a gene walk based on sequence prediction was used to evaluate 81 potential iRNA agents targeting human and mouse ApoB mRNA. Based on the results provided, Table 1 provides active iRNA agents targeting ApoB. One can readily design and generate other iRNA agents that are based on, comprise or consist of one of the active sequences provided herein such that at least a portion of an active sequence is included in the iRNA agents.

The iRNA agents shown in Example 2 hereinbelow are composed of a sense strand of 21 nucleotides in length, and an antisense strand of 23 nucleotides in length. However, while these lengths may potentially be optimal, the iRNA agents are not meant to be limited to these lengths. The skilled person is well aware that shorter or longer iRNA agents may be similarly effective, since, within certain length ranges, the efficacy is rather a function of the nucleotide sequence than strand length. For example, Yang, D., et al., PNAS 2002, 99:9942-9947, demonstrated similar efficacies for iRNA agents of lengths between 21 and 30 base pairs. Others have shown effective silencing of genes by iRNA agents down to a length of approx. 15 base pairs (Byrom, W. M., et al., Inducing RNAi with siRNA Cocktails Generated by RNase III; Tech Notes 10(1), Ambion, Inc., Austin, Tex., USA).

Therefore, it is possible and contemplated by the instant invention to select from the sequences provided in Table 1 a partial sequence of between 15 to 22 nucleotides for the generation of an iRNA agent derived from one of the sequences provided in Table 1. Alternatively, one may add one or several nucleotides to one of the sequences provided in Table 1, preferably, but not necessarily, in such a fashion that the added nucleotides are complementary to the respective sequence of the target gene, e.g. ApoB. All such derived iRNA agents are included in the iRNA agents of the present invention, provided they essentially retain the ability to inhibit ApoB expression in cultured human HepG2 cells.

Generally, the iRNA agents of the instant invention include a region of sufficient complementarity to the ApoB gene, and are of sufficient length in terms of nucleotides, that the iRNA agent, or a fragment thereof, can mediate down regulation of the ApoB gene. The antisense strands of the iRNA agents of Table 1 are fully complementary to the mRNA sequences of mouse (GenBank Accession number: XM_137955) and human (GenBank Accession number: NM_000384) ApoB, and their sense strands are fully complementary to the antisense strands except for the two 3'-terminal nucleotides on the antisense strand. However, it is not necessary that there be perfect complementarity between the mRNA agent and the target, but the correspondence must be sufficient to enable the iRNA agent, or a cleavage product thereof, to direct sequence specific silencing, e.g., by RNAi cleavage of an ApoB mRNA.

Therefore, the iRNA agents of the instant invention include agents comprising a sense strand and antisense strand each comprising a sequence of at least 16, 17 or 18 nucleotides which is essentially identical, as defined below, to one of the sequences of Table 1, except that not more than 1, 2 or 3 nucleotides per strand, respectively, have been substituted by other nucleotides (e.g. adenosine replaced by uracil), while essentially retaining the ability to inhibit ApoB expression in cultured human HepG2 cells, as defined below. These agents will therefore possess at least 15 nucleotides identical to one of the sequences of Table 1, but 1, 2 or 3 base mismatches with respect to either the target ApoB mRNA sequence or between the sense and antisense strand are introduced. Mismatches to the target ApoB mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

The antisense strand of an iRNA agent should be equal to or at least, 14, 15, 16 17, 18, 19, 25, 29, 40, or 50 nucleotides in length. It should be equal to or less than 60, 50, 40, or 30, nucleotides in length. Preferred ranges are 15-30, 17 to 25, 19 to 23, and 19 to 21 nucleotides in length.

The sense strand of an iRNA agent should be equal to or at least 14, 15, 16 17, 18, 19, 25, 29, 40, or 50 nucleotides in length. It should be equal to or less than 60, 50, 40, or nucleotides in length. Preferred ranges are 15-30, 17 to 25, 19 to 23, and 19 to 21 nucleotides in length.

The double stranded portion of an iRNA agent should be equal to or at least, 15, 16 17, 18, 19, 20, 21, 22, 23, 24, 25, 29, 40, or 50 nucleotide pairs in length. It should be equal to or less than 60, 50, 40, or 30 nucleotides pairs in length. Preferred ranges are 15-30, 17 to 25, 19 to 23, and 19 to 21 nucleotides pairs in length.

It is preferred that the sense and antisense strands be chosen such that the iRNA agent includes a single strand or unpaired region at one or both ends of the molecule. Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 4, or preferably 2 or 3 nucleotides, in length at each end. The overhangs can be the result of one strand being longer than the other, or the result of two strands of the same length being staggered. 5'-ends are preferably phosphorylated.

Preferred lengths for the duplexed region is between 15 and 30, most preferably 18, 19, 20, 21, 22, and 23 nucleotides in length, e.g., in the siRNA agent range discussed above.

siRNA agents can resemble in length and structure the natural Dicer processed products from long dsRNAs. Embodiments in which the two strands of the siRNA agent are linked, e.g., covalently linked are also included. Hairpin, or other single strand structures which provide the required double stranded region, and preferably a 3' overhang are also within the invention.

Much of the discussion below refers to single strand molecules. In many embodiments of the invention a ds iRNA agent, e.g., a partially ds iRNA agent, is required or preferred. Thus, it is understood that that double stranded structures (e.g. where two separate molecules are contacted to form the double stranded region or where the double stranded region is formed by intramolecular pairing (e.g., a hairpin structure)) made of the single stranded structures described below are within the invention. Preferred lengths are described elsewhere herein.

Evaluation of Candidate iRNA Agents

A candidate iRNA agent can be evaluated for its ability to downregulate target gene expression. For example, a candidate iRNA agent can be provided, and contacted with a cell, e.g. a HepG2 cell, that expresses the target gene, e.g., the ApoB gene, either endogenously or because it has been transfected with a construct from which ApoB can be expressed. The level of target gene expression prior to and following contact with the candidate iRNA agent can be compared, e.g. on an mRNA or protein level. If it is determined that the amount of RNA or protein expressed from the target gene is lower following contact with the iRNA agent, then it can be concluded that the iRNA agent downregulates target gene expression. The level of target ApoB RNA or ApoB protein in the cell can be determined by any method desired. For example, the level of target RNA can be determined by Northern blot analysis, reverse transcription coupled with polymerase chain reaction (RT-PCR), or RNAse protection assay. The level of protein can be determined, for example, by Western blot analysis.

Stability Testing, Modification, and Retesting of iRNA Agents

A candidate iRNA agent can be evaluated with respect to stability, e.g, its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-β-mathyl group. This further iRNA agent can be retested for stability, and this process may be iterated until an iRNA agent is found exhibiting the desired stability.

In Vivo Testing

An iRNA agent identified as being capable of inhibiting ApoB gene expression can be tested for functionality in vivo in an animal model (e.g., in a mammal, such as in mouse or rat). For example, the iRNA agent can be administered to an animal, and the iRNA agent evaluated with respect to its biodistribution, stability, and its ability to inhibit ApoB gene expression.

The iRNA agent can be administered directly to the target tissue, such as by injection, or the iRNA agent can be administered to the animal model in the same manner that it would be administered to a human The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}$S, $^{32}$P, $^{33}$P, or $^{3}$H; gold particles; or antigen particles for immunohistochemistry).

An iRNA agent useful for monitoring biodistribution can lack gene silencing activity in vivo. For example, the iRNA agent can target a gene not present in the animal (e.g., an iRNA agent injected into mouse can target luciferase), or an iRNA agent can have a non-sense sequence, which does not target any gene, e.g., any endogenous gene). Localization/biodistribution of the iRNA can be monitored, e.g. by a traceable label attached to the iRNA agent, such as a traceable agent described above The iRNA agent can be evaluated with respect to its ability to down regulate ApoB gene expression. Levels of ApoB gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target ApoB mRNA can be detected by any desired method, including but not limited to RT-PCR, Northern blot, branched-DNA assay, or RNAase protection assay. Alternatively, or additionally, ApoB gene expression can be monitored by performing Western blot analysis on tissue extracts treated with the iRNA agent.

iRNA Chemistry

Described herein are isolated iRNA agents, e.g., RNA molecules, (double-stranded; single-stranded) that mediate RNAi to inhibit expression of ApoB.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res*. 22: 2183-2196. Such rare or unusual RNAs, often termed modified RNAs (apparently because the are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occur in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Modifications described herein can be incorporated into any double-stranded RNA and RNA-like molecule described herein, e.g., an iRNA agent. It may be desirable to modify one or both of the antisense and sense strands of an iRNA agent.

As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an mRNA agent can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An iRNA agent can include ligand-conjugated monomer subunits and monomers for oligonucleotide synthesis. Exemplary monomers are described in co-owned U.S. application Ser. No. 10/916,185, filed on Aug. 10, 2004.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

The sense and antisense sequences of an iRNA agent can be palindromic. Exemplary features of palindromic iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Enhanced Nuclease Resistance

An iRNA agent, e.g., an iRNA agent that targets ApoB, can have enhanced resistance to nucleases. One way to increase resistance is to identify cleavage sites and modify such sites to inhibit cleavage. For example, the dinucleotides 5'-UA-3', 5'-UG-3',5'-CA-3',5'-UU-3', or 5'-CC-3' can serve as cleavage sites, as described in co-owned and co-pending applications U.S. 60/574,744 and PCT/US2005/018931.

For increased nuclease resistance and/or binding affinity to the target, an iRNA agent, e.g., the sense and/or antisense strands of the iRNA agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$ AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C-allyl, and 2'-fluoro.

To maximize nuclease resistance, the 2' modifications can be used in combination with one or more phosphate linker modifications (e.g., phosphorothioate). The so-called "chimeric" oligonucleotides are those that contain two or more different modifications.

In certain embodiments, all the pyrimidines of an iRNA agent carry a 2'-modification, and the iRNA agent therefore has enhanced resistance to endonucleases. Enhanced nuclease resistance can also be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. Preferably, the 5'-most pyrimidines in all occurrences of the sequence motifs 5'-UA-3',5'-CA-3',5'-UU-3', and 5'-UG-3' are 2'-modified nucleotides. More preferably, all pyrimidines in the sense strand are 2'-modified nucleotides, and the 5'-most pyrimidines in all occurrences of the sequence motifs 5'-UA-3' and 5'-CA-3'. Most preferably, all pyrimidines in the sense strand are 2'-modified nucleotides, and the 5'-most pyrimidines in all occurrences of the sequence motifs 5'-UA-3',5'-CA-3',5'-UU-3', and 5'-UG-3' are 2'-modified nucleotides in the antisense strand. The latter patterns of modifications have been shown by the instant inventors to maximize the contribution of the nucleotide modifications to the stabilization of the overall molecule towards nuclease degradation, while minimizing the overall number of modifications required to a desired stability, see co-owned and co-pending PCT/US2005/018931, hereby incorporated herein by reference in its entirety.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include monomers which have been modified so as to inhibit degradation, e.g., by nucleases, e.g., endonucleases or exonucleases, found in the body of a subject. These monomers are referred to herein as NRMs, or Nuclease Resistance promoting Monomers or modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

While not wishing to be bound by theory, it is believed that modifications of the sugar, base, and/or phosphate backbone in an iRNA agent can enhance endonuclease and exonuclease resistance, and can enhance interactions with transporter proteins and one or more of the functional components of the RISC complex. Preferred modifications are those that increase exonuclease and endonuclease resistance and thus prolong the half-life of the iRNA agent prior to interaction with the RISC complex, but at the same time do not render the iRNA agent inactive with respect to its intended activity as a target mRNA cleavage directing agent. Again, while not wishing to be bound by any theory, it is believed that placement of the modifications at or near the 3' and/or 5'-end of antisense strands can result in iRNA agents that meet the preferred nuclease resistance criteria delineated above. Again, still while not wishing to be bound by any theory, it is believed that placement of the modifications at e.g., the middle of a sense strand can result in iRNA agents that are relatively less likely to show off-target effects.

Modifications that can be useful for producing iRNA agents that meet the preferred nuclease resistance criteria delineated above can include one or more of the following chemical and/or stereochemical modifications of the sugar, base, and/or phosphate backbone:

(i) chiral ($S_P$) thioates. Thus, preferred NRMs include nucleotide dimers with an enriched or pure for a particular chiral form of a modified phosphate group containing a heteroatom at the nonbridging position, e.g., Sp or Rp, at the position X, where this is the position normally occupied by the oxygen. The atom at X can also be S, Se, $Nr_2$, or $Br_3$. When X is S, enriched or chirally pure Sp linkage is preferred. Enriched means at least 70, 80, 90, 95, or 99% of the preferred form. Such NRMs are discussed in more detail below;

(ii) attachment of one or more cationic groups to the sugar, base, and/or the phosphorus atom of a phosphate or modified phosphate backbone moiety. Thus, preferred NRMs include monomers at the terminal position derivatized at a cationic group. As the 5'-end of an antisense sequence should have a terminal —OH or phosphate group this NRM is preferably not used at the 5'-end of an antisense sequence. The group should be attached at a position on the base which minimizes interference with H bond formation and hybridization, e.g., away form the face which interacts with the complementary base on the other strand, e.g, at the 5' position of a pyrimidine or a 7-position of a purine. These are discussed in more detail below;

(iii) nonphosphate linkages at the termini. Thus, preferred NRMs include Non-phosphate linkages, e.g., a linkage of 4 atoms which confers greater resistance to cleavage than does a phosphate bond. Examples include 3' $CH2\text{-}NCH_3$—O—$CH_2$-5' and 3' $CH_2$—NH—(O=)—$CH_2$-5'.;

(iv) 3'-bridging thiophosphates and 5'-bridging thiophosphates. Thus, preferred NRM's can included these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage;

(vi) conjugate groups. Thus, preferred NRM's can include, e.g., a targeting moiety or a conjugated ligand described herein conjugated with the monomer, e.g., through the sugar, base, or backbone;

(vi) abasic linkages. Thus, preferred NRM's can include an abasic monomer, e.g., an abasic monomer as described herein (e.g., a nucleobaseless monomer); an aromatic or heterocyclic or polyheterocyclic aromatic monomer as described herein; and (vii) 5'-phosphonates and 5'-phosphate prodrugs. Thus, preferred NRM's include monomers, preferably at the terminal position, e.g., the 5' position, in which one or more atoms of the phosphate group is derivatized with a protecting group, which protecting group or groups, are removed as a result of the action of a component in the subject's body, e.g, a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an iRNA agent or into a sequence of an iRNA agent. An NRM modification can be used more than once in a sequence or in an iRNA agent. As some NRMs interfere with hybridization the total number incorporated, should be such that acceptable levels of iRNA agent duplex formation are maintained.

In some embodiments NRM modifications are introduced into the terminal cleavage site or in the cleavage region of a sequence (a sense strand or sequence) which does not target a desired sequence or gene in the subject. This can reduce off-target silencing.

Nuclease resistant modifications include some which can be placed only at the terminus and others which can go at any position. Generally the modifications that can inhibit hybridization so it is preferably to use them only in terminal regions, and preferable to not use them at the cleavage site or in the cleavage region of an sequence which targets a subject sequence or gene. The can be used anywhere in a sense sequence, provided that sufficient hybridization between the two sequences of the iRNA agent is maintained. In some embodiments it is desirable to put the NRM at the cleavage site or in the cleavage region of a sequence which does not target a subject sequence or gene, as it can minimize off-target silencing.

In addition, an iRNA agent described herein can have an overhang which does not form a duplex structure with the other sequence of the iRNA agent—it is an overhang, but it does hybridize, either with itself, or with another nucleic acid, other than the other sequence of the iRNA agent.

In most cases, the nuclease-resistance promoting modifications will be distributed differently depending on whether the sequence will target a sequence in the subject (often referred to as an antisense sequence) or will not target a sequence in the subject (often referred to as a sense sequence). If a sequence is to target a sequence in the subject, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt guide RNA, or about 10 or 11 nucleotides upstream of the first nucleotide which is complementary to the guide sequence. As used herein cleavage site refers to the nucleotide on either side of the cleavage site, on the target or on the iRNA agent strand which hybridizes to it. Cleavage region means an nucleotide with 1, 2, or 3 nucleotides of the cleave site, in either direction.)

Such modifications can be introduced into the terminal regions, e.g., at the terminal position or with 2, 3, 4, or 5 positions of the terminus, of a sequence which targets or a sequence which does not target a sequence in the subject.

Tethered Ligands

The properties of an iRNA agent, including its pharmacological properties, can be influenced and tailored, for example, by the introduction of ligands, e.g. tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer \ when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_n NH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g, molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a liver cell or a cell of the jejunum. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, glycerol (e.g., esters and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O (hexadecyl)glycerol, 1,3-bis-O (octaadecyl)glycerol), geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the IRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Peptides that target markers enriched in proliferating cells can be used. E.g., RGD containing peptides and petomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogenesis. Preferred conjugates of this type include an iRNA agent that targets PECAM-1, VEGF, or other cancer gene, e.g., a cancer gene described herein.

A targeting agent that incorporates a sugar, e.g., galactose and/or analogues thereof, is particularly useful. These agents target, in particular, the parenchymal cells of the liver. For example, a targeting moiety can include more than one or preferably two or three galactose moieties, spaced about 15 angstroms from each other. The targeting moiety can alternatively be lactose (e.g., three lactose moieties), which is glucose coupled to a galactose. The targeting moiety can also be N-Acetyl-Galactosamine, N-Ac-Glucosamine. A mannose or mannose-6-phosphate targeting moiety can be used for macrophage targeting.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

iRNA Conjugates

An iRNA agent can be coupled, e.g., covalently coupled, to a second agent. For example, an iRNA agent used to treat a particular disorder, such as a lipid disorder, can be coupled to a second therapeutic agent, e.g., an agent other than the iRNA agent. The second therapeutic agent can be one which is directed to the treatment of the same disorder.

5'-Phosphate Modifications

In preferred embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Delivery of iRNA Agents to Tissues and Cells

Targeting to the Liver

The iRNA agent that targets ApoB can be targeted to the liver, for example by associating, e.g., conjugating the iRNA agent to a lipophilic moiety, e.g., a lipid, oleyl, retinyl, or cholesteryl residue. Conjugation to cholesterol is preferred. Other lipophilic moieties that can be associated, e.g., conjugated with the iRNA agent include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. Alternatively, the iRNA agent can be targeted to the liver by associating, e.g., conjugating, the iRNA agent to a low-density lipoprotein (LDL), e.g., a lactosylated LDL, or the iRNA agent can be targeted to the liver by associating, e.g., conjugating, the iRNA agent to a polymeric carrier complex with sugar residues.

The iRNA agent can be targeted to the liver by associating, e.g., conjugating, the iRNA agent to a liposome complexed with sugar residues. A targeting agent that incorporates a sugar, e.g., galactose and/or analogues thereof, is particularly useful. These agents target, in particular, the parenchymal cells of the liver. Preferably, the targeting moiety includes more than one galactose moiety, more preferably two or three. Most preferably, the targeting moiety includes three galactose moieties, e.g., spaced about 15 angstroms from each other. The targeting moiety can be lactose. A lactose is a glucose coupled to a galactose. Preferably, the targeting moiety includes three lactoses. The targeting moiety can also be N-Acetyl-Galactosamine, N-Ac-Glucosamine. A mannose, or mannose-6-phosphate targeting moiety can be used for macrophage targeting.

An iRNA agent can also be targeted to the liver by association with a low-density lipoprotein (LDL), such as lactosylated LDL. Polymeric carriers complexed with sugar residues can also function to target iRNA agents to the liver.

The targeting agent can be linked directly, e.g., covalently or non covalently, to the iRNA agent, or to another delivery or formulation modality, e.g., a liposome. E.g., the iRNA agents with or without a targeting moiety can be incorporated into a delivery modality, e.g., a liposome, with or without a targeting moiety.

The iRNA agent that targets ApoB can be targeted to the liver, for example by associating, e.g., conjugating the iRNA agent, to a serum albumin (SA) molecule, e.g., a human serum albumin (HSA) molecule, or a fragment thereof. The iRNA agent or composition thereof can have an affinity for an SA, e.g., HSA, which is sufficiently high such that its levels in the liver are at least 10, 20, 30, 50, or 100% greater in the presence of SA, e.g., HSA, or is such that addition of exogenous SA will increase delivery to the liver. These criteria can be measured, e.g., by testing distribution in a mouse in the presence or absence of exogenous mouse or human SA.

The SA, e.g., HSA, targeting agent can be linked directly, e.g., covalently or non-covalently, to the iRNA agent, or to another delivery or formulation modality, e.g., a liposome. E.g., the iRNA agents with or without a targeting moiety can be incorporated into a delivery modality, e.g., a liposome, with or without a targeting moiety.

Transport of iRNA Agents into Cells

Not wishing to be bound by any theory, the chemical similarity between cholesterol-conjugated iRNA agents and certain constituents of lipoproteins (e.g. cholesterol, cholesteryl esters, phospholipids) may lead to the association of iRNA agents with lipoproteins (e.g. LDL, HDL) in blood and/or the interaction of the iRNA agent with cellular components having an affinity for cholesterol, e.g. components of the cholesterol transport pathway. Lipoproteins as well as their constituents are taken up and processed by cells by various active and passive transport mechanisms, for example, without limitation, endocytosis of LDL-receptor bound LDL, endocytosis of oxidized or otherwise modified LDLs through interaction with Scavenger receptor A, Scavenger receptor B1-mediated uptake of HDL cholesterol in the liver, pinocytosis, or transport of cholesterol across membranes by ABC (ATP-binding cassette) transporter proteins, e.g. ABC-A1, ABC-G1 or ABC-G4. Hence, cholesterol-conjugated iRNA agents could enjoy facilitated uptake by cells possessing such transport mechanisms, e.g. cells of the liver. As such, the present invention provides evidence and general methods for targeting IRNA agents to cells expressing certain cell surface components, e.g. receptors, by conjugating a natural ligand for such component (e.g. cholesterol) to the iRNA agent, or by conjugating a chemical moiety (e.g. cholesterol) to the iRNA agent which associates with or binds to a natural ligand for the component (e.g. LDL, HDL).

Other Embodiments

An RNA, e.g., an iRNA agent, can be produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328, 470), or by stereotactic injection (see, e.g., Chen et al., *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of an iRNA agent and one that produces a transcript that includes the bottom strand of an iRNA agent. When the templates are transcribed, the iRNA agent is produced, and processed into siRNA agent fragments that mediate gene silencing.

Physiological Effects

The mRNA agents described herein can be designed such that determining therapeutic toxicity is made easier by the complementarity of the iRNA agent with both a human and a non-human animal sequence. By these methods, an iRNA agent can consist of a sequence that is fully complementary to a nucleic acid sequence from a human and a nucleic acid sequence from at least one non-human animal, e.g., a non-human mammal, such as a rodent, ruminant or primate. For example, the non-human mammal can be a mouse, rat, dog, pig, goat, sheep, cow, monkey, *Pan paniscus, Pan troglodytes, Macaca mulatto,* or Cynomolgus monkey. The sequence of the iRNA agent could be complementary to sequences within homologous genes, e.g., oncogenes or tumor suppressor genes, of the non-human mammal and the human. By determining the toxicity of the iRNA agent in the non-human mammal, one can extrapolate the toxicity of the iRNA agent in a human. For a more strenuous toxicity test, the iRNA agent can be complementary to a human and more than one, e.g., two or three or more, non-human animals.

The methods described herein can be used to correlate any physiological effect of an iRNA agent on a human, e.g., any unwanted effect, such as a toxic effect, or any positive, or desired effect.

iRNA Production

An iRNA can be produced, e.g., in bulk, by a variety of methods. Exemplary methods include: organic synthesis and RNA cleavage, e.g., in vitro cleavage.

Organic Synthesis. An iRNA can be made by separately synthesizing each respective strand of a double-stranded RNA molecule. The component strands can then be annealed.

A large bioreactor, e.g., the OligoPilot II from Pharmacia Biotec AB (Uppsala Sweden), can be used to produce a large amount of a particular RNA strand for a given iRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the oligonucleotide strands for the iRNA. Typically, the two complementary strands are produced separately and then annealed, e.g., after release from the solid support and deprotection.

Organic synthesis can be used to produce a discrete iRNA species. The complementarity of the species to the ApoB gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

dsRNA Cleavage. iRNAs can also be made by cleaving a larger ds iRNA. The cleavage can be mediated in vitro or in vivo. For example, to produce iRNAs by cleavage in vitro, the following method can be used:

In vitro transcription. dsRNA is produced by transcribing a nucleic acid (DNA) segment in both directions. For example, the HiScribe™ RNAi transcription kit (New England Biolabs) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used. In one embodiment, RNA generated by this method is carefully purified to remove endotoxins that may contaminate preparations of the recombinant enzymes.

In vitro cleavage. dsRNA is cleaved in vitro into iRNAs, for example, using a Dicer or comparable RNAse III-based activity. For example, the dsRNA can be incubated in an in vitro extract from *Drosophila* or using purified components, e.g. a purified RNAse or RISC complex. See, e.g., Ketting et al. *Genes Dev* 2001 Oct. 15; 15(20):2654-9. and Hammond *Science* 2001 Aug. 10; 293(5532):1146-50.

dsRNA cleavage generally produces a plurality of iRNA species, each being a particular 21 to 23 nt fragment of a source dsRNA molecule. For example, iRNAs that include sequences complementary to overlapping regions and adjacent regions of a source dsRNA molecule may be present.

Regardless of the method of synthesis, the iRNA preparation can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Synthesis of modified and nucleotide surrogate iRNA agents is discussed below.

Formulation

The iRNA agents described herein can be formulated for administration to a subject.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA agent that can mediate RNAi with respect to a second gene, or with respect to the same gene. Still other preparations can include at least three, five, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than an RNA or a DNA).

In some embodiments, an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof) is formulated to target a particular cell. For example, a liposome or particle or other structure that includes a iRNA can also include a targeting moiety that recognizes a specific molecule on a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell.

In one embodiment, the targeting moiety is attached to a liposome. For example, U.S. Pat. No. 6,245,427 describes a method for targeting a liposome using a protein or peptide. In another example, a cationic lipid component of the liposome is derivatized with a targeting moiety. For example, WO 96/37194 describes converting N-glutaryldioleoylphosphatidyl ethanolamine to a N-hydroxysuccinimide activated ester. The product was then coupled to an RGD peptide. Additional targeting methods are described elsewhere herein.

Treatment Methods and Routes of Delivery

A composition that includes an iRNA agent, e.g., an iRNA agent that targets ApoB, can be delivered to a subject by a variety of routes. Exemplary routes include intrathecal, parenchymal, intravenous, nasal, oral, and ocular delivery. An iRNA agent can be incorporated into pharmaceutical compositions suitable for administration. For example, compositions can include one or more species of an iRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, or intrathecal or intraventricular administration.

The route of delivery can be dependent on the disorder of the patient.

In general, an iRNA agent can be administered by any suitable method. As used herein, topical delivery can refer to the direct application of an iRNA agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the iRNA agent to the epidermis or dermis of a subject, or to specific strata thereof, or to an underlying tissue.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An iRNA agent can be administered to a subject by pulmonary delivery. Pulmonary delivery compositions can be delivered by inhalation by the patient of a dispersion so that the composition, preferably iRNA, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. An iRNA composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

An iRNA agent can be modified such that it is capable of traversing the blood brain barrier. For example, the iRNA agent can be conjugated to a molecule that enables the agent to traverse the barrier. Such modified iRNA agents can be administered by any desired method, such as by intraventricular or intramuscular injection, or by pulmonary delivery, for example.

An iRNA agent can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the iRNA agent can also be applied via an ocular patch.

An iRNA agent can be administered by an oral or nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily.

Administration can be provided by the subject or by another person, e.g., a another caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The subject can also be monitored for an improvement or stabilization of disease symptoms.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

In one embodiment, unit doses or measured doses of a composition that include iRNA are dispensed by an implanted device. The device can include a sensor that monitors a parameter within a subject. For example, the device can include a pump, such as an osmotic pump and, optionally, associated electronics.

An iRNA agent can be packaged in a viral natural capsid or in a chemically or enzymatically produced artificial capsid or structure derived therefrom.

Dosage. An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmole of RNA agent (e.g., about $4.4 \times 1016$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight. The unit dose, for example, can be administered by injection (e.g., intravenous or intramuscular, intrathecally, or directly into an organ), an inhaled dose, or a topical application.

Delivery of an iRNA agent directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 μg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the iRNA agent pharmaceutical composition includes a plurality of iRNA agent species. The iRNA agent species can have sequences that are non-overlapping and non-adjacent with respect to a naturally occurring target sequence, e.g., a target sequence of the ApoB gene. In another embodiment, the plurality of iRNA agent species is specific for different naturally occurring target genes. For example, an iRNA agent that targets ApoB can be present in the same pharmaceutical composition as an iRNA agent that targets a different gene. In another embodiment, the iRNA agents are specific for different alleles.

Following successful treatment, it may be desirable to have the patient undergo maintenance therapy to prevent the recurrence of the disease state, wherein the compound of the invention is administered in maintenance doses, ranging from 0.01 μg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent, e.g., a double-stranded iRNA agent, or siRNA agent (e.g., a precursor, e.g., a larger iRNA agent which can be processed into an siRNA agent, or a DNA which encodes an iRNA agent, e.g., a double-stranded iRNA agent, or siRNA agent, or precursor thereof) can include a single treatment or, preferably, can include a series of treatments. It will also be appreciated that the effective dosage of an iRNA agent such as an siRNA agent used for treatment may increase or decrease over the course of a particular treatment. Changes in dosage may result and become apparent from the results of diagnostic assays as described herein. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target ApoB RNA. The transgenic animal can be deficient for the corresponding endogenous RNA. In another embodiment, the composition for testing includes an iRNA agent that is complementary, at least in an internal region, to a sequence that is conserved between the target ApoB RNA in the animal model and the target ApoB RNA in a human.

The invention is further illustrated by the following examples, which should not be construed as further limiting.

EXAMPLES

Example 1 siRNAs were Produced by Solid-Phase Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Glen Research, Sterling Va.) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification by anion exchange HPLC of the crude oligoribonucleotides were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The purified RNA solution was stored at −20° C. until use.

Cholesterol was conjugated to siRNA as illustrated in FIG. 1. For the synthesis of these 3'-cholesterol-conjugated siRNAs, an appropriately modified solid support was used for RNA synthesis. The modified solid support was prepared as follows:

Diethyl-2-azabutane-1,4-dicarboxylate AA

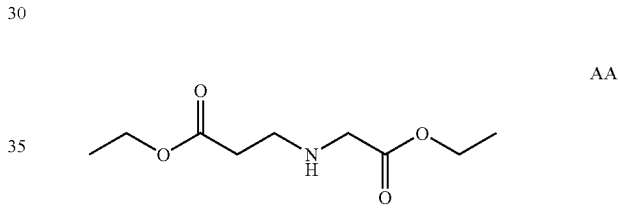

AA

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until the completion of reaction was ascertained by TLC (19 h). After 19 h which it was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

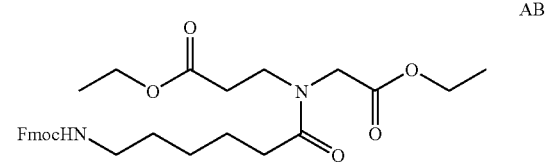

AB

Fmoc-6-amino-hexanoic acid (9.12 g, 25.83 mmol) was dissolved in dichloromethane (50 mL) and cooled with ice-. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. the completion of the reaction was ascertained by TLC. The reaction mixture was concentrated in vacuum and to the ethylacetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-{Ethoxycarbonylmethyl-[6-(9H-fluoren-9-ylmethoxy-carbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated in vacuum and the residue water was added and the product was extracted with ethyl acetate. The crude product was purified by converting into hydrochloride salt.

3-[(6-Amino-hexanoyl)-ethoxycarbonylmethyl-amino]-propionic acid ethyl ester AC

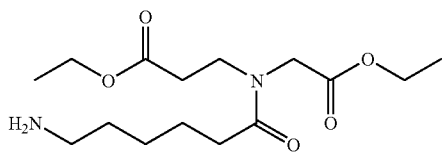

AC 3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

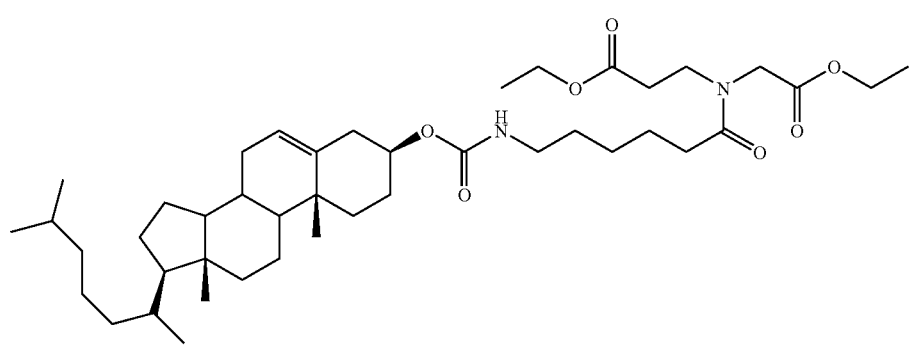

AD

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE

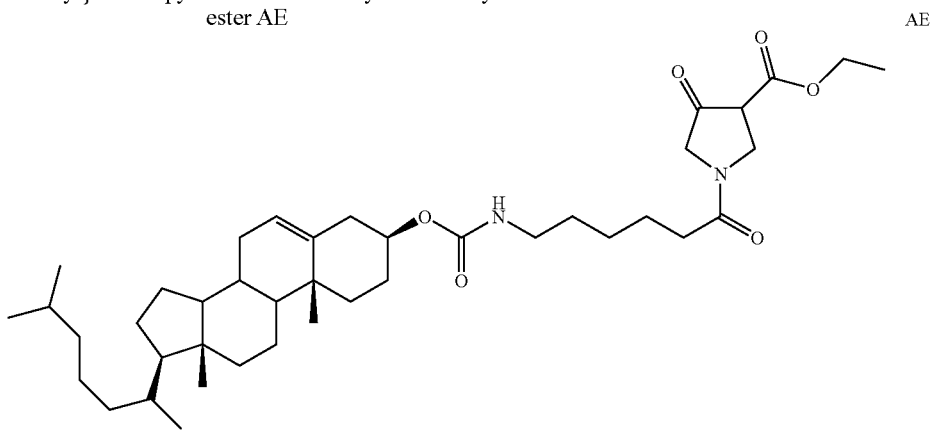

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of NaH$_2$PO$_4$.H$_2$O in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to a residue. The residue was purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

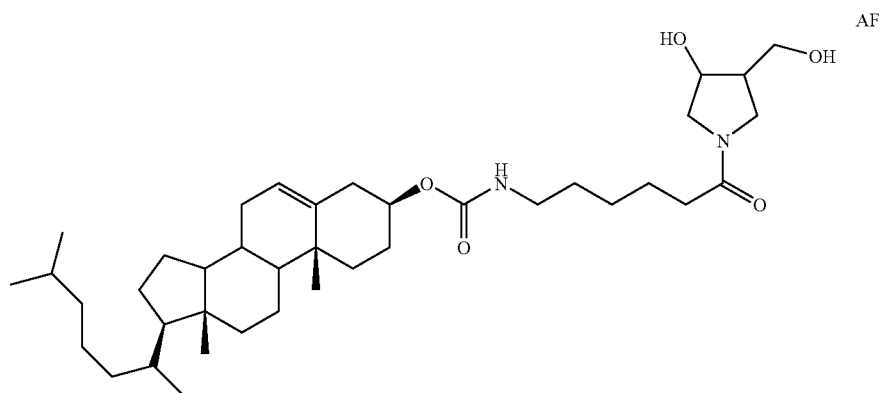

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated in vacuum to yield the product which was purified by column chromatography (10% MeOH/CHCl$_3$) (89%).

(6-{3-[Bis-(4-methoxyl-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

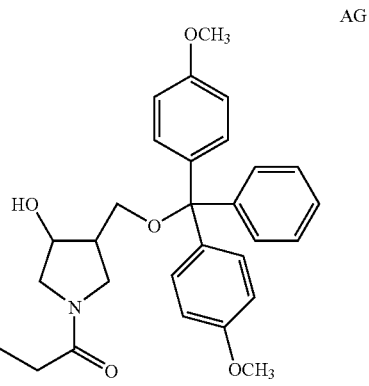
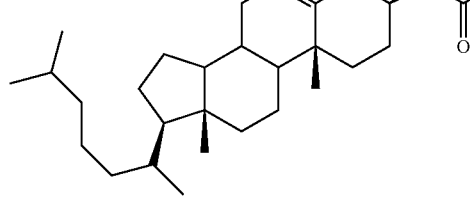

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated in vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15, 16,17-tetradecahydro-1H cyclopenta[a]phenanthren-3-yloxycarbonylamino]-hexanoyl}-pyrrolidin-3-yl) ester AH

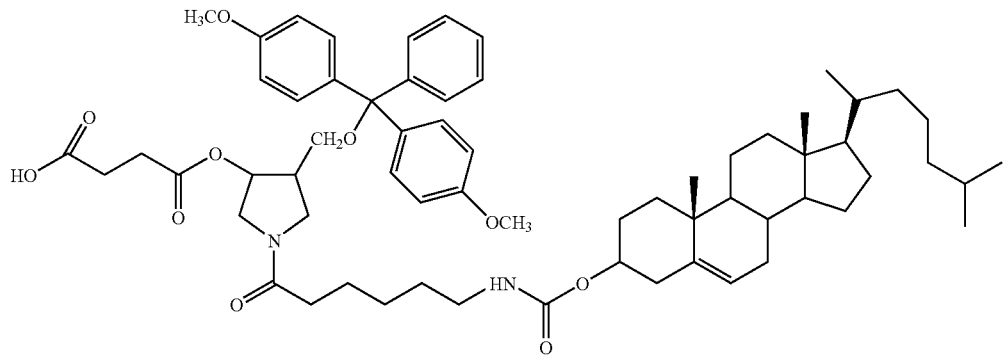

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG AI

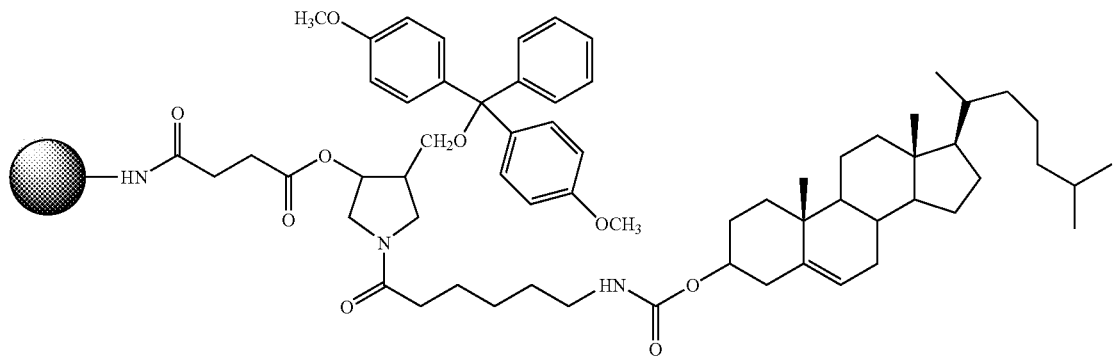

AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using wrist-action shaker (5 mins). Long chain alkyl amine-CPG (LCAA-CPG) (1.5 g, 61 mm/g) was added. The suspension was agitated for 2 h. The CPG was filtered through a sintered funnel and washed with acetonitrile, dichloromethane and ether successively. Unreacted amino groups were masked using acetic anhydride/pyridine. The loading capacity of the CPG was measured by taking UV measurement (37 mM/g).

The synthesis and structure of cholesterol conjugated RNA strands is illustrated in FIG. 1.

Example 2 siRNAs were Designed to Target Regions in Human and Mouse ApoB Genes

Nucleic acid sequences are represented below using standard nomenclature, and specifically the abbreviations of Table 2.

wherein the 5'-most nucleotide is counted as the first nucleotide, and counting is continued in the 3'-direction.

Since therapeutics for use in humans are typically first tested in animals, we designed siRNAs that would potentially have an effect both in an animal model system as well as in a human. The animal model system chosen was the mouse, *mus musculus*. Therefore, the first criterion in choosing sequences for siRNA targeting was cross-reactivity between mouse and human ApoB.

In order to select siRNAs that would potentially inhibit ApoB gene expression in mouse as well as in humans, the sequences coding for the open reading frame of mouse (GenBank Accession number: XM_137955) and human (GenBank Accession number: NM_000384) ApoB were aligned using a pair wise BLAST algorithm. The mathematical algorithm used in BLAST programs is described in Altschul et al. (Nucleic Acids Res. 25:3389-3402, 1997). Regions with identity in 23 or more consecutive nucleotides (nucleotides in mouse open reading frame: 463-494, 622-647, 658-680, 701-725, 1216-1240, 1282-1320, 1299-1328, 1339-1362, 2124-2155, 2807-2830, 2809-2837, 2860-2901, 3035-3057, 3103-3125, 3444-3467, 3608-3635, 4130-4167, 4374-4402, 4503-4525, 5962-5985, 6696-6724, 9232-9257, 9349-9372, 10177-10213, 10477-10505, 10791-10814, 11020-11045, 12227-12251, 13539-13572) were identified.

All possible nucleotide sequences of 23 nucleotides in length were determined. This set represented 170 potential

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A, a | 2'-deoxy-adenosine-5'-phosphate, adenosine-5'-phosphate |
| C, c | 2'-deoxy-cytidine-5'-phosphate, cytidine-5'-phosphate |
| G, g | 2'-deoxy-guanosine-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| Y, y | pyrimidine (C or T, c or u) |
| R, r | purine (A or G, a or g) |
| N, n | any (G, A, C, or T, g, a, c or u) |
| am | 2'-O-methyladenosine-5'-phosphate |
| cm | 2'-O-methylcytidine-5'-phosphate |
| gm | 2'-O-methylguanosine-5'-phosphate |
| tm | 2'-O-methyl-thymidine-5'-phosphate |
| um | 2'-O-methyluridine-5'-phosphate |
| af | 2'-fluoro-2'-deoxy-adenosine-5'-phosphate |
| cf | 2'-fluoro-2'-deoxy-cytidine-5'-phosphate |
| gf | 2'-fluoro-2'-deoxy-guanosine-5'-phosphate |
| tf | 2'-fluoro-2'-deoxy-thymidine-5'-phosphate |
| uf | 2'-fluoro-2'-deoxy-uridine-5'-phosphate |
| A, C, G, T, U, a, c, g, t, u | underlined: nucleoside-5'-phosphorothioate |
| am, cm, gm, tm, um | underlined: 2-O-methyl-nucleoside-5'-phosphorothioate |
| *A, C, G, T, U, a, c, g, t, u* | bold italic: 2'-deoxy-adenosine, 2'-deoxy-cytidine, 2'-deoxy-guanosine, 2'-deoxy-thymidine, 2'-deoxy-uridine, adenosine, cytidine, guanosine, thymidine, uridine (5'-hydroxyl) |
| *am, cm, gm, tm, um* | bold italic: 2'-O-methyl-adenosine, 2'-O-methyl-cytidine, 2'-O-methyl-guanosine, 2'-O-methyl-thymidine, 2'-O-methyl-uridine (5'-hydroxyl) |

[a]capital letters represent 2'-deoxyribonucleotides (DNA), lower case letters represent ribonucleotides (RNA)

Certain oligonucleotides described herein were modified to include a cholesterol moiety linked to their 3'-end (see FIG. 1). These are denoted as 5'-(n)$_n$(Chol)-3'.

Where this text refers to "position n" (n being an integer number) within a given nucleotide sequence, this is meant to refer to the n-th nucleotide in the nucleotide sequence, siRNA targeting regions. These sequences were compared by BLAST searching (word size 7, mismatch penalty-1, expect value 1000) against human and mouse genome and mRNA databases. All potential 23 nucleotide target regions with 3 or less sequence mismatches to any non-ApoB sequence in the mouse mRNA and mouse genome databases were excluded from the initial set. The remaining 84 potential targeting regions served as template to derive the siRNA sense and antisense strands. The sense strand of each siRNA was identical to nucleotides 3 to 23 (5' to 3') from the potential target region. The antisense strand was defined as the reverse complement of the full 23 nucleotide target region. The resulting siRNAs had 2 nucleotide overhangs at the 3'-end of the antisense strand and a base-paired region of 21 nucleotides. 81 of these 84 potential siRNAs were synthesized and their efficacy in inhibiting the expression of ApoB in cultured human HepG2 cells was determined. For those siRNAs effecting a repression of ApoB mRNA expression to less than 50% of ApoB mRNA levels in untreated control cells, the stability in human and/or mouse serum was also determined.

The sequences of the sense and antisense strands of the 84 synthesized siRNA duplexes are shown in Table 3. Sense strands represent nucleotides 3-23 of all 23 nucleotide regions which are: (a) homologous between the open reading frames (ORF) of mouse (GenBank Accession number: XM_137955) and human (GenBank Accession number: NM_000384) ApoB; and (b) were found to have 4 or more mismatches when compared to all other entries in the human and mouse genome and mRNA databases. The antisense strands shown in Table 3 are complementary to nucleotides 1-23 of the 23 sense strand nucleotide regions. The position of the 5'-most nucleotide of the corresponding 23 nucleotide region in the ORF of mouse ApoB is also given.

TABLE 3

Nucleic acid sequences of unmodified siRNA duplexes

| SEQ. ID No. | Sequence sense strand | SEQ. ID No. | Sequence antisense strand | Duplex descriptor[a] | Start pos.[b] |
|---|---|---|---|---|---|
| 1 | <sup>a</sup>agccuugguucaguguggac | 2 | <sup>g</sup>uccacacugaaccaaggcuugu | AL-DUP 5000 | 1302 |
| 3 | ugaacaccaacuucuuccacg | 4 | <sup>c</sup>guggaagaaguugguguucauc | AL-DUP 5001 | 2865 |
| 5 | <sup>g</sup>auugauugaccugaccauuc | 6 | <sup>g</sup>aauggacaggucaaucaaucuu | AL-DUP 5002 | 13539 |
| 7 | <sup>a</sup>auggacucaucugcuacagc | 8 | <sup>g</sup>cuguagcagaugaguccauuug | AL-DUP 5003 | 3610 |
| 9 | <sup>a</sup>uugaccuguccauucaaaac | 10 | <sup>g</sup>uuuugaauggacaggucaauca | AL-DUP 5004 | 13544 |
| 11 | uuugugacaaauaugggcauc | 12 | <sup>g</sup>augcccauauuugucacaaacu | AL-DUP 5005 | 2810 |
| 13 | <sup>c</sup>uugguucaguguggacagcc | 14 | <sup>g</sup>gcuguccacacugaaccaaggc | AL-DUP 5006 | 1306 |
| 15 | uggacucaucugcuacagcuu | 16 | <sup>a</sup>agcuguagcagaugaguccauu | AL-DUP 5007 | 3612 |
| 17 | <sup>a</sup>uugauugaccuguccauuca | 18 | ugaauggacaggucaaucaaucu | AL-DUP 5008 | 13540 |
| 19 | uugauugaccuguccauucaa | 20 | uugaauggacaggucaaucaauc | AL-DUP 5009 | 13541 |
| 21 | <sup>c</sup>aaauggacucaucugcuaca | 22 | uguagcagaugaguccauuugga | AL-DUP 5010 | 3608 |
| 23 | <sup>g</sup>auugaccuguccauucaaaa | 24 | uuuugaauggacaggucaaucaa | AL-DUP 5011 | 13543 |
| 25 | ugauugaccuguccauucaaa | 26 | uuugaauggacaggucaaucaau | AL-DUP 5012 | 13542 |
| 27 | <sup>g</sup>guguauggcuucaacccuga | 28 | ucagggguugaagccauacaccuc | AL-DUP 5013 | 466 |
| 29 | ucugugggauuccaucugcca | 30 | uggcagauggaaucccacagacu | AL-DUP 5014 | 4136 |
| 31 | <sup>a</sup>gacuuccugaauaacuaugc | 32 | <sup>g</sup>cauaguuauucaggaagucuau | AL-DUP 5015 | 9349 |
| 33 | <sup>a</sup>caauuugaucaguauauuaa | 34 | uuaauauacugaucaaauuguau | AL-DUP 5016 | 6697 |
| 35 | <sup>g</sup>gacucaucugcuacagcuua | 36 | uaagcuguagcagaugaguccau | AL-DUP 5017 | 3613 |
| 37 | uuacuccaacgccagcuccac | 38 | <sup>g</sup>uggagcuggcguuggaguaagc | AL-DUP 5018 | 3103 |
| 39 | <sup>g</sup>ugacaaauaugggcaucauc | 40 | <sup>g</sup>augaugcccauauuugucacaa | AL-DUP 5019 | 2813 |
| 41 | <sup>g</sup>uguauggcuucaacccugag | 42 | <sup>c</sup>ucagggguugaagccauacaccu | AL-DUP 5020 | 467 |
| 43 | uaccguguauggaaacugcuc | 44 | <sup>g</sup>agcaguuuccauacacgguauc | AL-DUP 5021 | 703 |
| 45 | <sup>g</sup>auaccguguauggaaacugc | 46 | <sup>g</sup>caguuuccauacacgguaucca | AL-DUP 5022 | 701 |
| 47 | <sup>a</sup>aaucaagugucaucacacug | 48 | <sup>c</sup>agugugaugacacuugauuuaa | AL-DUP 5023 | 10178 |
| 49 | <sup>a</sup>gguguauggcuucaacccug | 50 | <sup>c</sup>agggguugaagccauacaccucu | AL-DUP 5024 | 465 |
| 51 | <sup>g</sup>uuugugacaaauaugggcau | 52 | <sup>a</sup>ugcccauauuugucacaaacuc | AL-DUP 5025 | 2809 |
| 53 | <sup>a</sup>uaccguguauggaaacugcu | 54 | <sup>a</sup>gcaguuuccauacacgguaucc | AL-DUP 5026 | 702 |
| 55 | uaaaucaagugucaucacacu | 56 | <sup>a</sup>gugugaugacacuugauuuaa | AL-DUP 5027 | 10177 |
| 57 | <sup>g</sup>agguguauggcuucaacccu | 58 | <sup>a</sup>gggguugaagccauacaccucuu | AL-DUP 5028 | 464 |

TABLE 3-continued

Nucleic acid sequences of unmodified siRNA duplexes

| SEQ. ID No. | Sequence sense strand | SEQ. ID No. | Sequence antisense strand | Duplex descriptor[a] | Start pos.[b] |
|---|---|---|---|---|---|
| 59 | uggcuucaacccugagggcaa | 60 | uugcccucaggguugaagccaua | AL-DUP 5029 | 472 |
| 61 | gaacaccaacuucuuccacga | 62 | ucguggaagaaguuggguguucau | AL-DUP 5030 | 2866 |
| 63 | guauggcuucaacccugaggg | 64 | cccucagggguugaagccauacac | AL-DUP 5031 | 469 |
| 65 | auggcuucaacccugagggca | 66 | ugcccucagggguugaagccauac | AL-DUP 5032 | 471 |
| 67 | aacaccaacuucuuccacgag | 68 | cucguggaagaaguugguguuca | AL-DUP 5033 | 2867 |
| 69 | acaccaacuucuuccacgagu | 70 | acucguggaagaaguuggguuc | AL-DUP 5034 | 2868 |
| 71 | caccaacuucuuccacgaguc | 72 | gacucguggaagaaguuggguu | AL-DUP 5035 | 2869 |
| 73 | gaugaacaccaacuucuucca | 74 | uggaagaaguuggguguucaucug | AL-DUP 5036 | 2863 |
| 75 | augaacaccaacuucuuccac | 76 | guggaagaaguuggguguucaucu | AL-DUP 5037 | 2864 |
| 77 | agaugaacaccaacuucuucc | 78 | ggaagaaguuggguguucaucugg | AL-DUP 5038 | 2862 |
| 79 | auuccaucugccaucucgaga | 80 | ucucgagauggcagauggaaucc | AL-DUP 5039 | 4144 |
| 81 | uuccaucugccaucucgagag | 82 | cucucgagauggcagauggaauc | AL-DUP 5040 | 4145 |
| 83 | acaagccuugguucagugugg | 84 | ccacacugaaccaaggcuuguaa | AL-DUP 5041 | 1300 |
| 85 | uucaagucugugggauuccau | 86 | auggaaucccacagacuugaagu | AL-DUP 5042 | 4130 |
| 87 | aaucaagugucaucacacuga | 88 | ucagugugaugacacuugauuua | AL-DUP 5043 | 10179 |
| 89 | uauggcuucaacccugagggc | 90 | gcccucagggguugaagccauaca | AL-DUP 5044 | 470 |
| 91 | uugaccuguccauucaaaacu | 92 | aguuuugaauggacaggucaauc | AL-DUP 5045 | 13545 |
| 93 | aucaagugucaucacacugaa | 94 | uucagugugaugacacuugauuu | AL-DUP 5046 | 10180 |
| 95 | ucaagugucaucacacugaau | 96 | auucagugugaugacacuugauu | AL-DUP 5047 | 10181 |
| 97 | gucaucacacugaauaccaau | 98 | auugguauucagugugaugacac | AL-DUP 5048 | 10187 |
| 99 | cuguccauucaaaacuaccac | 100 | gugguaguuugaauggacaggu | AL-DUP 5049 | 13550 |
| 101 | ccuguccauucaaaacuacca | 102 | ugguaguuugaauggacagguc | AL-DUP 5050 | 13549 |
| 103 | aucacacugaauaccaaugcu | 104 | agcauugguauucagugugauga | AL-DUP 5051 | 10190 |
| 105 | accuguccauucaaaacuacc | 106 | gguaguuugaauggacagguca | AL-DUP 5052 | 13548 |
| 107 | gaccuguccauucaaaacuac | 108 | guaguuugaauggacaggucaa | AL-DUP 5053 | 13547 |
| 109 | caucacacugaauaccaaugc | 110 | gcauugguauucagugugaugac | AL-DUP 5054 | 10189 |
| 111 | uacaagccuugguucagugug | 112 | cacacugaaccaaggcuuguaaa | AL-DUP 5055 | 1299 |
| 113 | uguauggcuucaacccugagg | 114 | ccucagggguugaagccauacacc | AL-DUP 5056 | 468 |
| 115 | ugaccuguccauucaaaacua | 116 | uaguuuugaauggacaggucaau | AL-DUP 5057 | 13546 |
| 117 | ucaucacacugaauaccaaug | 118 | cauugguauucagugugaugaca | AL-DUP 5058 | 10188 |
| 119 | uugugacaaauaugggcauca | 120 | ugaugcccauauuugucacaaac | AL-DUP 5059 | 2811 |
| 121 | caagugucaucacacugaaua | 122 | uauucagugugaugacacuugau | AL-DUP 5060 | 10182 |
| 123 | uaacacuaagaaccagaagau | 124 | aucuucugguucuuaguguuagc | AL-DUP 5061 | 11020 |
| 125 | caauuugaucaguauauuaaa | 126 | uuuaauauacugaucaauuugua | AL-DUP 5062 | 6698 |
| 127 | cugaacaucaagaggggcauc | 128 | gaugcccucuugauguucagga | AL-DUP 5084 | 623 |
| 129 | ugaacaucaagaggggcauca | 130 | ugaugcccucuugauguucagg | AL-DUP 5085 | 624 |
| 131 | guccagccccaucacuuuaca | 132 | uguaaagugauggggcuggacac | AL-DUP 5086 | 1282 |

TABLE 3-continued

Nucleic acid sequences of unmodified siRNA duplexes

| SEQ. ID No. | Sequence sense strand | SEQ. ID No. | Sequence antisense strand | Duplex descriptor[a] | Start pos.[b] |
|---|---|---|---|---|---|
| 133 | cagccccaucacuuuacaagc | 134 | gcuuguaaagugauggggcugga | AL-DUP 5087 | 1285 |
| 135 | agccccaucacuuuacaagcc | 136 | ggcuuguaaagugauggggcugg | AL-DUP 5088 | 1286 |
| 137 | gaguuugugacaaauaugggc | 138 | gcccauauuugucacaaacucca | AL-DUP 5089 | 2807 |
| 139 | agggaaucuuauauuugaucc | 140 | ggaucaaauauaagauucccuuc | AL-DUP 5090 | 2131 |
| 141 | uuacugagcugagaggccuca | 142 | ugaggccucucagcucaguaacc | AL-DUP 5091 | 1218 |
| 143 | auugggaagaagaggcagcuu | 144 | aagcugccucuucuucccaauua | AL-DUP 5092 | 12228 |
| 145 | ucacauccuccaguggcugaa | 146 | uucagccacuggaggaugugagu | AL-DUP 5093 | 1339 |
| 147 | gccccaucacuuuacaagccu | 148 | aggcuuguaaagugauggggcug | AL-DUP 5094 | 1287 |
| 149 | ccagccccaucacuuuacaag | 150 | cuuguaaagugauggggcuggac | AL-DUP 5095 | 1284 |
| 151 | agggaaucuuauauuugauc | 152 | gaucaaauauaagauucccuucu | AL-DUP 5096 | 2130 |
| 153 | cuuuacaagccuugguucagu | 154 | acugaaccaaggcuuguaaagug | AL-DUP 5097 | 1296 |
| 155 | ggaaucuuauauuugauccaa | 156 | uuggaucaaauauaagauucccu | AL-DUP 5098 | 2133 |
| 157 | gaagggaaucuuauauuugau | 158 | aucaaauauaagauucccuucua | AL-DUP 5099 | 2129 |
| 159 | aaauagaagggaaucuuauau | 160 | auauaagauucccuucuauuuug | AL-DUP 5100 | 2124 |
| 161 | uagaagggaaucuuauauuug | 162 | caaauauaagauucccuucuauu | AL-DUP 5101 | 2127 |
| 163 | gacuuccugaauaacuaugca | 164 | ugcauaguuauucaggaagucua | | 9350 |
| 165 | gcaaggaucuggagaaacaac | 166 | guuguuucuccagauccuugcac | | 4375 |
| 167 | caaggaucuggagaaacaaca | 168 | uguuguuucuccagauccuugca | | 4376 |

[a]Descriptor refers to annealed duplex siRNA
[b]Position of the 5'-most nucleotide of the corresponding 23 nucleotide region in the ORF of mouse ApoB Alternatively, for the same set of 84 potential target regions, siRNAs may be generated with 19 basepairs and 2 nucleotide dTdT overhangs. The sense strand is then identical to nucleotides 1 to 19, 2 to 20, 3 to 21, 4 to 22, or 5 to 23 from the target region, and two dT nucleotides are added to the 3'-end of the oligonucleotide. The reverse complement of the sense strand so selected would then serve as template for the antisense strand, and two dT nucleotides would be added to the 3'-end.

Example 3 siRNAs Inhibited ApoB Expression, Both on the mRNA as Well as the Protein Level, in Cell Culture The activity of the siRNAs described above was tested in HepG2 cells.

HepG2 cells in culture were used for quantitation of ApoB mRNA in total mRNA isolated from cells incubated with ApoB-specific siRNAs by branched DNA assay, and of ApoB 100 protein in supernatant of cells incubated with ApoB-specific siRNAs by Enzyme-linked immunosorbent assay (ELISA). HepG2 cells were obtained from American Type Culture Collection (Rockville, Md., cat. No. HB-8065) and cultured in MEM (Gibco Invitrogen, Invitrogen GmbH, Karlsruhe, Germany, cat. No. 21090-022) supplemented to contain 10% fetal calf serum (FCS) (Biochrom AG, Berlin, Germany, cat. No. S0115), 2 mM L-Glutamin (Biochrom AG, Berlin, Germany, cat. No. K0238), Penicillin 100 U/ml, Streptomycin 100 µg/ml (Biochrom AG, Berlin, Germany, cat. No. A2213), 1× non-essential amino acids (NEA) (Biochrom AG, Berlin, Germany, cat. No. K0293) and 1 mM sodium pyruvate (Biochrom AG, Berlin, Germany, cat. No. L0473) at 37° C. in an atmosphere with 5% $CO_2$ in a humidified incubator (Heraeus HERAcell, Kendro Laboratory Products, Langenselbold, Germany).

For transfection with siRNA, HepG2 cells were seeded at a density of $1.5 \times 10^4$ cells/well in 96-well plates and cultured for 24 hours. Transfection of siRNA was carried out with oligofectamine (Invitrogen GmbH, Karlsruhe, Germany, cat. No. 12252-011) as described by the manufacturer. SiRNAs were transfected at a concentration of 100 nM for the screening of siRNA duplexes, and 100, 33, 11, 3.7, 1.2, 0.4, 0.14, and 0.05 nM when assessing dose response/inhibitor concentration at 50% maximal inhibition ($IC_{50}$). 24 hours after transfection, the medium was changed and cells were incubated for an additional 24 hours. For the assessment of ApoB100 protein concentration by enzyme-linked immunosorbent assay, as described below, supernatant was collected and stored at −80° C. until analysis. For measurement of ApoB mRNA by branched DNA assay, as described below, cells were harvested and lysed following procedures recommended by the manufacturer of the Quantigene Explore Kit (Genospectra, Fremont, Calif., USA, cat. No. QG-000-02)

for bDNA quantitation of mRNA, except that 2 µl of a 50 µg/µl stock solution of Proteinase K (Epicentre, Madison, Wis., USA, Cat. No. MPRK092) was added to 600 µl of Tissue and Cell Lysis Solution (Epicentre, Madison, Wis., USA, cat. No. MTC096H). Lysates were stored at −80° C. until analysis by branched DNA assay.

NmuLi cells in culture were used for quantitation of murine ApoB mRNA by branched DNA assay (bDNA assay). NmuLi cells (normal murine liver, ATCC Number: CRL-1638) were cultured in DMEM (Biochrom AG, Berlin, Germany, cat. No. F0435) supplemented to contain 10% fetal calf serum (FCS) (Biochrom AG, Berlin, Germany, cat. No. 50115) and 2 mM L-Glutamin (Biochrom AG, Berlin, Germany, cat. No. K0238) at 37° C. under an atmosphere containing 5% $CO_2$ in a humidified incubator (Heraeus HERAcell, Kendro Laboratory Products, Langenselbold, Germany).

One day before transfection, $4 \times 10^3$ cells per well were seeded on 96-well plates. Cells were transfected with siRNAs in triplicate with oligofectamine according to the manufacturer's protocol (Invitrogen GmbH, Karlsruhe, Germany, cat. No. 12252-011). Concentration of the siRNA in the medium during transfection was 200 nM for the screening of 15 unmodified or modified siRNA duplexes. Following transfection, cells were cultured for 24 h, after which the growth medium was exchanged for fresh medium not containing the siRNA. Cell lysates were obtained and stored as described above for HepG2 cells.

The sequences of an siRNA duplex used as a non-cholesterol conjugated control is shown below:

```
AL-DUP HCV
Sense:
5'-acggcuagcugugaaaggucc-3'      SEQ. ID No. 169

Antisense:
5'-ggaccuuucacagcuagccguga-3'    SEQ. ID No. 170
```

The sense strand of AL-DUP HCV corresponds to positions 9472-9493 of the 3'-untranslated region of hepatitis C virus (Accession number: D89815).

The sequences of an siRNA duplex used as a cholesterol-conjugated control is shown below:

```
AL-DUP 5129
Sense:
5'-ccacaugaagcagcacgacuu(Chol)-3'   SEQ. ID No. 171

Antisense:
5'-aagucgugcugcuucaugug-3'          SEQ. ID No. 172
```

Nucleotides 1-21 of the sense strand correspond to positions 843-864 in cloning vector pEGFP-C3 with enhanced green fluorescent protein (GenBank Accession number: U57607).

ApoB 100 protein levels in cell supernatants were measured by ELISA assay. Clear Flat Bottom Polystyrene High Bind Microplates (Corning B.V. Life Sciences, Schiphol-Rijk, The Netherlands, cat. no. 9018) were used for the assays. Polyclonal antibody goat anti-human-apolipoprotein B (Chemicon International GmbH, Hofheim, Germany, cat. no. AB742) was diluted 1:1000 in phosphate buffered saline (PBS) (PBS Dulbecco w/o $Ca^{2+}$, $Mg^{2+}$, Biochrom AG, Berlin, Germany, cat. No. L182-05) and 100 µl of this dilution was coated on 96-well plates at 4° C. overnight. After blocking with 300 µl of 1% bovine serum albumin (BSA) (Carl Roth GmbH & Co KG, Karlsruhe, Germany, cat. no. 8076.2) in PBS the plate was washed three times with PBS.

Cell culture supernatant was thawed and diluted 1:1 with PBS containing 0.1% Tween 20 (Carl Roth GmbH & Co KG, Karlsruhe, Germany, cat. No. 9127.1) and 0.1% BSA. 100 µl of this dilution was added to each well. After an incubation time of 2 hours at room temperature, the plate was washed five times with PBS containing 0.1% Tween 20 followed by three washes with PBS. 100 µl of a horseradish-peroxidase conjugated Goat Anti-Human Apolipoprotein B-100 polyclonal antibody (Academy Bio-Medical Company, Houston, Tex., USA, cat. No. 20H-G1-b) diluted 1:1000 in PBS containing 0.1% Tween 20 and 3% BSA was added to each well. The plate was incubated for 2 hours at room temperature. After washing the plate five times with PBS containing 0.1% Tween 20 and three times with PBS, wells were incubated with 0.9 mg/ml OPD (o-phenylendiamine dihydrochloride, Merck Biosciences GmbH, Bad Soden, Germany cat. No. 523121) in 24 mmol/L citric acid buffer (Sigma-Aldrich, Taufkirchen, Germany, cat. no. C1909-1KG), pH 5.0, containing 0.03% hydrogen peroxide (Merck Biosciences GmbH, Bad Soden, Germany cat. No. 386790). The enzyme reaction was halted by adding 0.5 mol/L $H_2SO_4$ (Merck KgaA, Darmstadt, Germany, cat. No. 100731) and absorbance at 490 nm was measured on a spectrophotometer (Perkin Elmer Wallac Victor3 1420 multilabel reader, PerkinElmer LAS GmbH, Rodgau, Germany). siRNA duplexes unrelated to any mouse gene were used as control, and the activity of a given ApoB specific siRNA duplex was expressed as percent ApoB protein concentration in the supernatant of treated cells relative to ApoB protein concentration in the supernatant of cells treated with the control siRNA duplex. The conjugation of a cholesterol moiety to the sense strand of siRNA duplexes enhanced the ApoB secretion-inducing effect in cultured HepG2 cells. Therefore, one siRNA duplex control included a conjugated cholesterol moiety (AL-DUP 5129).

ApoB100 mRNA levels were measured by branched-DNA (bDNA) assay. The assay was performed using the Quantigene Explore Kit (Genospectra, Fremont, Calif., USA, cat. No. QG-000-02). Frozen lysates were thawed at room temperature, and ApoB and GAPDH mRNA quantified using the Quantigene Explore Kit according to manufacturer's instructions. Nucleic acid sequences for Capture Extender (CE), Label Extender (LE) and blocking (BL) probes were selected from the nucleic acid sequences of ApoB and GAPDH with the help of the QuantiGene ProbeDesigner Software 2.0 (Genospectra, Fremont, Calif., USA, cat. No. QG-002-02). Probe nucleotide sequences used in quantization of murine and human ApoB are shown in Table 4 and Table 5, respectively. Probe nucleotide sequences used in quantization of murine and human GAPDH are shown in Table 6 and Table 7, respectively.

TABLE 4

DNA probes for murine ApoB used in branched-DNA assays

| Probe type[a] | Nucleotide sequence | SEQ. ID. No. |
|---|---|---|
| CE | CTCATTCTCCAGCAGCAGGGTTTTCTCTTGGAAAGAAAGT | 173 |
| CE | GAAGCGGCCGTTTGTTGATATTTTCTCTTGGAAAGAAAGT | 174 |
| CE | GTTTTTGCTGTCTGCACCCATTTTCTCTTGGAAAGAAAGT | 175 |
| CE | TAAATATTGTCCATTTTTGAGAAGAAGTTTTCTCTTGGAAAGAAAGT | 176 |
| CE | CATTCAGCTTCAGTGGCTCCATTTTCTCTTGGAAAGAAAGT | 177 |
| CE | AATGTCTGCATTTAGCCTATGGCTTTTTCTCTTGGAAAGAAAGT | 178 |
| LE | AGCCCAAGCTCTGCATTCAATTTTTAGGCATAGGACCCGTGTCT | 179 |
| LE | ATTTCATGGATGCCCCAGAGTTTTTAGGCATAGGACCCGTGTCT | 180 |
| LE | ACTGAATTTTGCATGGTGTTCTTTTTTTAGGCATAGGACCCGTGTCT | 181 |
| LE | GGGCAGCTCTCCCATCAAGTTTTTAGGCATAGGACCCGTGTCT | 182 |
| LE | GAATCATGGCCTGGTAAATGCTTTTTAGGCATAGGACCCGTGTCT | 183 |
| LE | CAGCATAGGAGCCCATCAAATCATTTTTAGGCATAGGACCCGTGTCT | 184 |
| LE | GACTGTGTGTGTGGTCAAGTTTCATCTTTTTAGGCATAGGACCCGTGTCT | 185 |
| LE | ATAGGGCTGTAGCTGTAAGTTAAAATTTTTAGGCATAGGACCCGTGTCT | 186 |
| LE | GTCAAATCTAGAGCACCATATCTCAGTTTTAGGCATAGGACCCGTGTCT | 187 |
| LE | GCCGAAACCTTCCATTGTTGTTTTAGGCATAGGACCCGTGTCT | 188 |
| LE | AGATATGTTTCAGCTCATTATTTTGATAGTTTTTAGGCATAGGACCCGTGTCT | 189 |
| LE | CTACTACCAGGTCAGTATAAGATATGGTATTTTTAGGCATAGGACCCGTGTCT | 190 |
| LE | GAATTCGACACCCTGAACCTTAGTTTTTAGGCATAGGACCCGTGTCT | 191 |
| BL | TCCCCAGTGACACCTCTGTGA | 192 |
| BL | TCGGCTGAGTTTGAAGTTGAAGAT | 193 |
| BL | TGGACAGCCTCAGCCCTTC | 194 |
| BL | TCCAGTGAGAGACCTGCAATGTTCA | 195 |
| BL | TCTGCTTATAGAACTTGTCTCCACTG | 196 |
| BL | GTCGTTGCTTAAAGTAGTTATGAAAGA | 197 |
| BL | GTTCCTTTAAAGTTGCCACCCA | 198 |
| BL | CCACAGTGTCTGCTCTGTAACTTG | 199 |

[a] CE = Capture Extender probe; LE = Label Extender probe; BL = blocking probe

TABLE 5

DNA probes for human ApoB used in branched-DNA assays

| Probe type[a] | Nucleotide sequence | SEQ. ID. No. |
|---|---|---|
| CE | GATTGGATTTTCAGAATACTGTATAGCTTTTTCTCTTGGAAAGAAAGT | 200 |
| CE | CCTGCTTCGTTTGCTGAGGTTTTTCTCTTGGAAAGAAAGT | 201 |
| CE | GCAGTGATGGAAGCTGCGATATTTTCTCTTGGAAAGAAAGT | 202 |
| CE | GAACTTCTAATTTGGACTCTCCTTTGTTTTTCTCTTGGAAAGAAAGT | 203 |
| CE | ACTCCTTCAGAGCCAGCGGTTTTTCTCTTGGAAAGAAAGT | 204 |

TABLE 5-continued

DNA probes for human ApoB used in branched-DNA assays

| Probe type[a] | Nucleotide sequence | SEQ. ID. No. |
|---|---|---|
| CE | *A*CTCCCATGCTCCGTTCTCATTTTTCTCTTGGAAAGAAAGT | 205 |
| CE | *A*GGGTAAGCTGATTGTTTATCTTGATTTTTCTCTTGGAAAGAAAGT | 206 |
| LE | *G*GTTCCATTCCCTATGTCAGCATTTTTAGGCATAGGACCCGTGTCT | 207 |
| LE | *A*TTAATCTTAGGGTTTGAGAGTTGTGTTTTTAGGCATAGGACCCGTGTCT | 208 |
| LE | *C*ACTGTGTTTGATTTTCCCTCAATATTTTTAGGCATAGGACCCGTGTCT | 209 |
| LE | *T*GTATTTTTTTCTGTGTGTAAACTTGCTTTTTAGGCATAGGACCCGTGTCT | 210 |
| LE | *C*AATCACTCCATTACTAAGCTCCAGTTTTTAGGCATAGGACCCGTGTCT | 211 |
| BL | *T*GCCAAAAGTAGGTACTTCAATTG | 212 |
| BL | *T*TTGCATCTAATGTGAAAAGAGGA | 213 |
| BL | *C*ATTTGCTTGAAAATCAAAATTGA | 214 |
| BL | *G*GTACTTGCTGGAGAACTTCACTG | 215 |
| BL | *G*CATTTCCAAAAAACAGCATTTC | 216 |

[a]CE = Capture Extender probe; LE = Label Extender probe; BL = blocking probe

TABLE 6

DNA probes for murine GAPDH used in branched-DNA assays

| Probe type[a] | Nucleotide sequence | SEQ. ID. No. |
|---|---|---|
| CE | *C*AAATGGCAGCCCTGGTGATTTTTCTCTTGGAAAGAAAGT | 217 |
| CE | *C*CTTGACTGTGCCGTTGAATTTTTTTCTCTTGGAAAGAAAGT | 218 |
| CE | *G*TCTCGCTCCTGGAAGATGGTTTTTCTCTTGGAAAGAAAGT | 219 |
| CE | *C*CCGGCCTTCTCCATGGTTTTTTCTCTTGGAAAGAAAGT | 220 |
| LE | *A*ACAATCTCCACTTTGCCACTGTTTTTAGGCATAGGACCCGTGTCT | 221 |
| LE | *C*ATGTAGACCATGTAGTTGAGGTCAATTTTTAGGCATAGGACCCGTGTCT | 222 |
| LE | *G*ACAAGCTTCCCATTCTCGGTTTTTAGGCATAGGACCCGTGTCT | 223 |
| LE | *T*GATGGGCTTCCCGTTGATTTTTTAGGCATAGGACCCGTGTCT | 224 |
| LE | *G*ACATACTCAGCACCGGCCTTTTTAGGCATAGGACCCGTGTCT | 225 |
| BL | *T*GAAGGGGTCGTTGATGGC | 226 |
| BL | *C*CGTGAGTGGAGTCATACTGGAA | 227 |
| BL | *C*ACCCCATTTGATGTTAGTGGG | 228 |
| BL | *G*GTGAAGACACCAGTAGACTCCAC | 229 |

[a]CE = Capture Extender probe; LB = Label Extender probe; BL = blocking probe

TABLE 7

DNA probes for human GAPDH used in branched-DNA assays

| Probe type[a] | Nucleotide sequence | SEQ. ID. No. |
|---|---|---|
| CE | *G*AATTTGCCATGGGTGGAATTTTTTCTCTTGGAAAGAAAGT | 230 |
| CE | *G*GAGGGATCTCGCTCCTGGATTTTTCTCTTGGAAAGAAAGT | 231 |

TABLE 7-continued

DNA probes for human GAPDH used in branched-DNA assays

| Probe type[a] | Nucleotide sequence | SEQ. ID. No. |
|---|---|---|
| CE | CCCCAGCCTTCTCCATGGTTTTTCTCTTGGAAAGAAAGT | 232 |
| CE | GCTCCCCCCTGCAAATGAGTTTTTCTCTTGGAAAGAAAGT | 233 |
| LE | AGCCTTGACGGTGCCATGTTTTTAGGCATAGGACCCGTGTCT | 234 |
| LE | GATGACAAGCTTCCCGTTCTCTTTTTAGGCATAGGACCCGTGTCT | 235 |
| LE | AGATGGTGATGGGATTTCCATTTTTTTAGGCATAGGACCCGTGTCT | 236 |
| LE | GCATCGCCCCACTTGATTTTTTTTAGGCATAGGACCCGTGTCT | 237 |
| LE | CACGACGTACTCAGCGCCATTTTTAGGCATAGGACCCGTGTCT | 238 |
| LE | GGCAGAGATGATGACCCTTTTGTTTTTAGGCATAGGACCCGTGTCT | 239 |
| BL | GGTGAAGACGCCAGTGGACTC | 240 |

[a]CE = Capture Extender probe; LE = Label Extender probe; BL = blocking probe

The ApoB mRNA levels were normalized across different samples by comparing the ratio of ApoB mRNA to GAPDH mRNA present in the samples. AL-DUP HCV, which does not target any mouse gene, and the cholesterol conjugated AL-DUP 5129 were used as controls. The activity of a given ApoB specific siRNA duplex was expressed as a percentage of ApoB mRNA (ApoB mRNA/GAPDH mRNA) in treated cells relative to cells treated with the control siRNA.

Table 8 shows the results from screening 81 siRNA duplexes for their activity in reducing ApoB mRNA levels in HepG2 cell cultures and ApoB protein levels in the supernatant of NmuLi cell cultures.

TABLE 8

Percentage ApoB mRNA and protein following treatment with siRNA

| Duplex descriptor | (ApoB mRNA/GAPDH mRNA) in HEPG2 cultured cells relative to controls | ApoB protein in HepG2 cell culture supernatant relative to controls |
|---|---|---|
| AL-DUP 5000 | 204 | 35 |
| AL-DUP 5001 | 141 | 37 |
| AL-DUP 5002 | 68 | 29 |
| AL-DUP 5003 | 121 | 119 |
| AL-DUP 5004 | 55 | 55 |
| AL-DUP 5005 | 250 | 129 |
| AL-DUP 5006 | 174 | 99 |
| AL-DUP 5007 | 96 | 72 |
| AL-DUP 5008 | 93 | 67 |
| AL-DUP 5009 | 68 | 92 |
| AL-DUP 5010 | 79 | 41 |
| AL-DUP 5011 | 98 | 44 |
| AL-DUP 5012 | 111 | 40 |
| AL-DUP 5013 | 37 | 24 |
| AL-DUP 5014 | 112 | 43 |
| AL-DUP 5015 | 165 | 54 |
| AL-DUP 5016 | 108 | 44 |
| AL-DUP 5017 | 117 | 46 |
| AL-DUP 5018 | 414 | 93 |
| AL-DUP 5019 | 46 | 56 |
| AL-DUP 5020 | 43 | 43 |
| AL-DUP 5021 | 103 | 45 |
| AL-DUP 5022 | 86 | 26 |
| AL-DUP 5023 | 218 | 74 |
| AL-DUP 5024 | 25 | 19 |
| AL-DUP 5025 | 64 | 47 |
| AL-DUP 5026 | 84 | 70 |
| AL-DUP 5027 | 45 | 51 |

TABLE 8-continued

Percentage ApoB mRNA and protein following treatment with siRNA

| Duplex descriptor | (ApoB mRNA/GAPDH mRNA) in HEPG2 cultured cells relative to controls | ApoB protein in HepG2 cell culture supernatant relative to controls |
|---|---|---|
| AL-DUP 5028 | 41 | 31 |
| AL-DUP 5029 | 44 | 29 |
| AL-DUP 5030 | 49 | 27 |
| AL-DUP 5031 | 45 | 36 |
| AL-DUP 5032 | 82 | 47 |
| AL-DUP 5033 | 115 | 87 |
| AL-DUP 5034 | 58 | 38 |
| AL-DUP 5035 | 46 | 26 |
| AL-DUP 5036 | 47 | 24 |
| AL-DUP 5037 | 120 | 53 |
| AL-DUP 5038 | 62 | 33 |
| AL-DUP 5039 | 56 | 45 |
| AL-DUP 5040 | 78 | 70 |
| AL-DUP 5041 | 387 | 45 |
| AL-DUP 5042 | 232 | 52 |
| AL-DUP 5043 | 65 | 54 |
| AL-DUP 5044 | 95 | 55 |
| AL-DUP 5045 | 65 | 57 |
| AL-DUP 5046 | 28 | 37 |
| AL-DUP 5047 | 29 | 56 |
| AL-DUP 5048 | 28 | 16 |
| AL-DUP 5049 | 31 | 36 |
| AL-DUP 5050 | 55 | 54 |
| AL-DUP 5051 | 65 | 55 |
| AL-DUP 5052 | 49 | 49 |
| AL-DUP 5053 | 37 | 46 |
| AL-DUP 5054 | 54 | 43 |
| AL-DUP 5055 | 205 | 101 |
| AL-DUP 5056 | 67 | 72 |
| AL-DUP 5057 | 77 | 66 |
| AL-DUP 5058 | 85 | 37 |
| AL-DUP 5059 | 116 | 61 |
| AL-DUP 5060 | 45 | 35 |
| AL-DUP 5061 | 40 | 43 |
| AL-DUP 5062 | 63 | 47 |
| AL-DUP 5084 | 26 | 52 |
| AL-DUP 5085 | 35 | 57 |
| AL-DUP 5086 | 36 | 69 |
| AL-DUP 5087 | 71 | 27 |
| AL-DUP 5088 | 35 | 28 |
| AL-DUP 5089 | 26 | 33 |
| AL-DUP 5090 | 64 | 51 |
| AL-DUP 5091 | 76 | 90 |
| AL-DUP 5092 | 37 | 81 |

TABLE 8-continued

Percentage ApoB mRNA and protein following treatment with siRNA

| Duplex descriptor | (ApoB mRNA/GAPDH mRNA) in HEPG2 cultured cells relative to controls | ApoB protein in HepG2 cell culture supernatant relative to controls |
|---|---|---|
| AL-DUP 5093 | 21 | 64 |
| AL-DUP 5094 | 15 | 29 |
| AL-DUP 5095 | 54 | 57 |
| AL-DUP 5096 | 55 | 62 |
| AL-DUP 5097 | 8 | 29 |
| AL-DUP 5098 | 11 | 24 |
| AL-DUP 5099 | 43 | 48 |
| AL-DUP 5100 | 17 | 57 |
| AL-DUP 5101 | 15 | 39 |

The 27 most active siRNA duplexes of Table 8 were determined to be those with a residual ApoB mRNA/GAPDH mRNA<31% of controls or residual ApoB protein levels <35% of controls. These siRNA duplexes were chosen for further analysis and establishment of IC50 values. These were: AL-DUP 5000, AL-DUP 5002, AL-DUP 5013, AL-DUP 5022, AL-DUP 5024, AL-DUP 5028, AL-DUP 5029, AL-DUP 5030, AL-DUP 5035, AL-DUP 5036, AL-DUP 5038, AL-DUP 5046, AL-DUP 5047, AL-DUP 5048, AL-DUP 5049, AL-DUP 5060, AL-DUP 5083, AL-DUP 5084, AL-DUP 5087, AL-DUP 5088, AL-DUP 5089, AL-DUP 5093, AL-DUP 5094, AL-DUP 5097, AL-DUP 5098, AL-DUP 5100, AL-DUP 5101.

Figure 2:
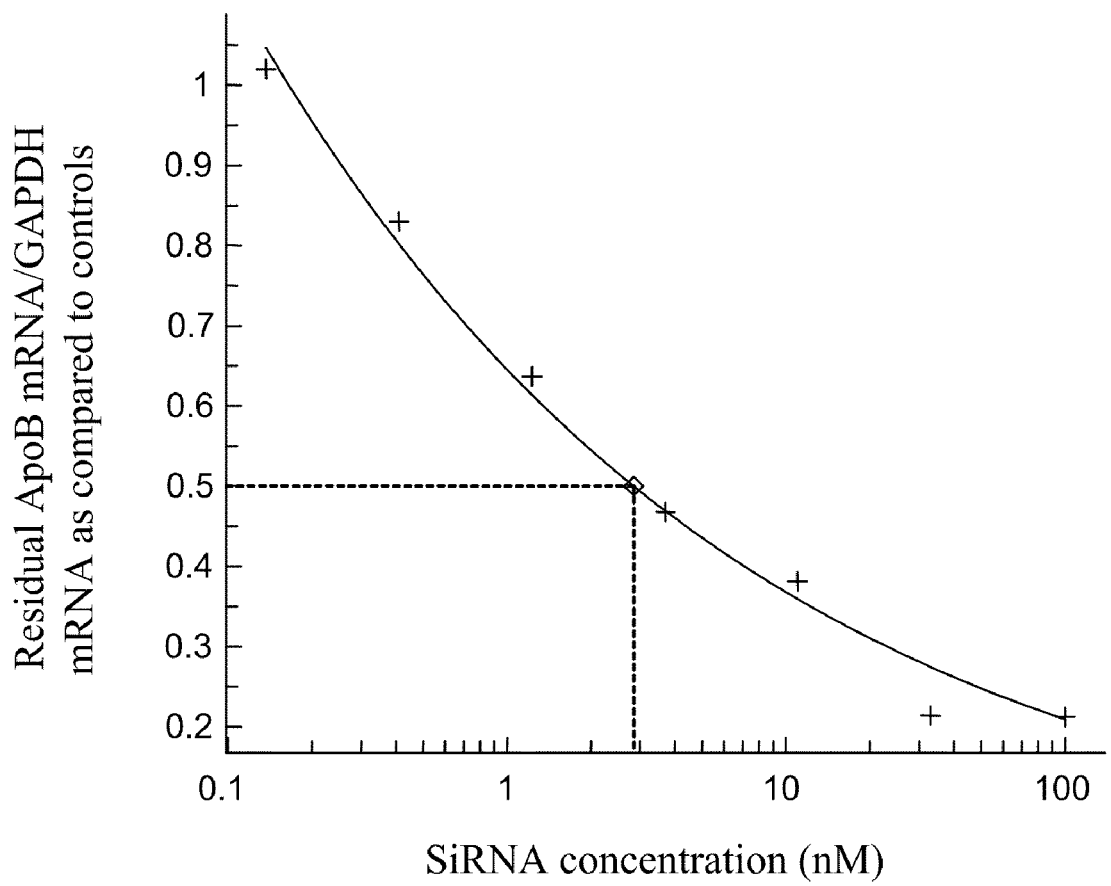
FIG. 2 is a graph depicting the ratio [ApoB mRNA]/[GAPDH control mRNA] following treatment of cells with increasing levels of siRNA, AL-DUP5024. Determination of the inhibitor concentration at 50% maximal inhibition ($IC_{50}$) was determined by curve fitting using the computer software Xlfit using the following parameters: Dose Response One Site, 4 Parameter Logistic Model, fit=$(A+((B-A)/(1+(((10\char`\^C)/x)\char`\^D))))$, inv=$((10\char`\^C)/((((B-A)/(y-A))-1)\char`\^(1/D)))$, res=$(y-fit)$.

Dose escalation studies were performed using the above-mentioned 27 siRNA duplexes, where ApoB mRNA was quantified in NmuLi cells and ApoB protein was quantified in cell culture supernatant of HepG2 cells after incubation with 100, 33, 11, 3.7, 1.2, 0.4, 0.14, or 0.05 nM solutions of the respective siRNA duplex. The minimum residual ApoB mRNA and ApoB protein levels were determined. For those 15 of the above 27 siRNA showing the lowest combined minimum residual ApoB mRNA and protein levels, the dose escalation was repeated three times, the resulting data were used to calculate inhibitor concentration at 50% maximal inhibition (IC50), and an average value was computed over the three determinations. IC50 was calculated by applying the data from the dose escalation experiments to curve fitting routines implemented in the computer software Xlfit 4 (ID Business Solutions Ltd., Guildford, UK). IC50 values were computed using the parameterized equations obtained from the line fit using the following parameters: Dose Response One Site, 4 Parameter Logistic Model, fit=$(A+((B-A)/(1+(((10^C)/x)^D))))$, inv=$((10^C)/((((B-A)/(y-A))-1)^{(1/D)}))$, res=(y-fit) (by way of example, see FIG. 2).

Table 9 shows the average IC50 values for the five ApoB siRNAs that reduced both mRNA and protein levels by >70% in NmuLi cells. Control experiments measured minimal residual ApoB mRNA/GAPDH mRNA in cultured NmuLi cells in percentage of untreated controls, and minimal residual ApoB protein in HepG2 cell supernatant in percentage of untested controls

TABLE 9

IC50 of selected siRNAs

| Duplex denominator | $IC_{50}$ (ApoB protein concentration) | Minimum residual ApoB mRNA/ GAPDH mRNA in % of controls | Minimum residual ApoB protein in cell supernatant in % of controls |
|---|---|---|---|
| AL-DUP 5097 | 0.3 nM | 15% | 18% |
| AL-DUP 5098 | 0.7 nM | 9% | 20% |
| AL-DUP 5094 | 0.7 nM | 14% | 7% |
| AL-DUP 5048 | 0.9 nM | 11% | 6% |
| AL-DUP 5024 | 2.8 nM | 12% | 21% |

AL-DUP 5024 and AL-DUP 5048 were chosen for further investigations.

Example 6 siRNA Duplexes were Modified and Exhibited Improved Resistance to Nucleases

The siRNA duplexes AL-DUP 5024 and AL-DUP 5048 were altered with various chemical modifications in an attempt to enhance the resistance of the oligonucleotide strands against degradation by nucleases present in biological fluids, such as, for example, serum and the intracellular medium. Specifically, phosphorothioate linkages were introduced between positions 21 and 22 and between positions 22 and 23 of the antisense strands, and/or between positions 20 and 21 of the sense strands (see Table 10), thereby increasing the stability of the siRNAs against exonucleolytic degradation.

TABLE 10 siRNAs for stability assays

| Duplex descriptor | SEQ. ID No. | Sense strand sequence | SEQ. ID No. | Antisense strand sequence |
|---|---|---|---|---|
| SiRNA duplexes derived from AL-DUP 5024 ||||||
| AL-DUP 5163 | 241 | ᵃgguguauggcuucaacccug (chol) | 242 | ᶜaggguugaagccauacaccum<u>cm</u>u |
| AL-DUP 5164 | 243 | ᵃggumgumaumggcumucmaacccumg (chol) | 244 | ᶜmagggumumgaagccmaumacmaccu<u>cu</u> |
| AL-DUP 5165 | 241 | ᵃgguguauggcuucaacccug (chol) | 244 | ᶜmagggumumgaagccmaumacmaccu<u>cu</u> |
| AL-DUP 5166 | 243 | ᵃggumgumaumggcumucmaacccumg (chol) | 242 | ᶜaggguugaagccauacaccum<u>cm</u>u |
| AL-DUP 5180 | 249 | ᵃggumgumaumggcumucmaacccum<u>g</u> | 242 | ᶜaggguugaagccauacaccum<u>cm</u>u |
| AL-DUP 5181 | 249 | ᵃggumgumaumggcumucmaacccum<u>g</u> | 244 | ᶜmagggumumgaagccmaumacmaccu<u>cu</u> |

TABLE 10-continued siRNAs for stability assays

| Duplex descriptor | SEQ. ID No. | Sense strand sequence | SEQ. ID No. | Antisense strand sequence |
|---|---|---|---|---|
| SiRNA duplexes derived from AL-DUP 5048 | | | | |
| AL-DUP 5167 | 253 | gucaucacacugaauaccaau (chol) | 254 | auugguauucagugugaugacmamc |
| AL-DUP 5168 | 255 | gucmaucmacmacumgaaumaccmaau (chol) | 256 | aumumggumaumucmagumgumgaumgacmac |
| AL-DUP 5169 | 253 | gucaucacacugaauaccaau (chol) | 256 | aumumggumaumucmagumgumgaumgacmac |
| AL-DUP 5170 | 255 | gucmaucmacmacumgaaumaccmaau (chol) | 254 | auugguauucagugugaugacmamc |
| AL-DUP 5182 | 261 | gucmaucmacmacumgaaumaccmaau | 254 | auugguauucagugugaugacmamc |
| AL-DUP 5183 | 261 | gucmaucmacmacumgaaumaccmaau | 256 | aumumggumaumucmagumgumgaumgacmac | m = 2'O-methyl modification; "(chol)" indicates cholesterol conjugated to the 3'-end via a pyrrolidine linker comprising a phosphorothioate Previously, this laboratory identified certain sequence motifs in siRNA duplexes which are particularly prone to degradative attack by endonucleases (see co-owned and co-pending application U.S. 60/574,744). Specifically, these motifs are 5'-UA-3', 5'-UG-3',5'-CA-3',5'-UU-3', and 5'-CC-3'. SiRNAs comprising these sequence motifs can be stabilized towards degradative attack by endonucleases by replacing the 2'-OH of the ribose subunit of the 5'-most nucleotide in these dinucleotide motifs with 2'-O—CH$_3$ (also referred to herein as 2'-O-Methyl or 2'-O-Me). Hence, siRNAs were synthesized wherein the respective nucleotides bear a 2'-O-Me group in all occurrences of these dinucleotide motifs, except for occurrences of 5'-CC-3', on either the sense strand, the antisense strand, or both.

A further modification tested was the conjugation of a cholesterol moiety to the 3'-end of the sense strand of the siRNAs (see FIG. 1). This modification is thought to facilitate the uptake of RNA into cells (Manoharan, M. et al., *Antisense and Nucleic Acid Drug Development* 2002, 12:103-128).

The siRNA duplexes listed in Table 10 were synthesized and tested for their stability towards nucleolytic degradation in the serum incubation assay, as well as their activity in reducing the amount of ApoB protein secreted into supernatant by cultured NmuLi cells.

The nucleotide sequences of siRNA AL-DUP 5024, AL-DUP 5163, AL-DUP 5164, AL-DUP 5165, AL-DUP 5166, AL-DUP 5180, and AL-DUP 5181 are identical except for the following:

AL-DUP 5024 consists entirely of unmodified nucleotides;

AL-DUP 5163 bears 2'-O-Me groups in positions 21 and 22 and phosphorothioate linkages between positions 21 and 22, and 22 and 23, of the antisense strand, and a cholesterol moiety conjugated to the 3'-end of the sense strand;

AL-DUP 5164 bears 2'-O-Me groups in positions 4, 6, 8, 12, 14, and 20 of its sense strand and in positions 1, 6, 7, 13, 15, and 17 of its antisense strand, phosphorothioate linkages between positions 21 and 22, and 22 and 23, of the antisense strand, and a cholesterol moiety conjugated to the 3'-end of the sense strand;

AL-DUP 5165 bears 2'-O-Me groups in positions 1, 6, 7, 13, 15, and 17 of its antisense strand, phosphorothioate linkages between positions 21 and 22, and 22 and 23, of the antisense strand, and a cholesterol moiety conjugated to the 3'-end of the sense strand;

AL-DUP 5166 bears 2'-O-Me modifications in positions 4, 6, 8, 12, 14, and 20 of its sense strand and in positions 21 and 22 of its antisense strand, phosphorothioate linkages between positions 21 and 22, and 22 and 23, of the antisense strand, and a cholesterol moiety conjugated to the 3'-end of the sense strand;

AL-DUP 5180 bears 2'-O-Me modifications in positions 4, 6, 8, 12, 14, and 20 of its sense strand and in positions 21 and 22 of its antisense strand, and phosphorothioate linkages between positions 21 and 22, and 22 and 23, of the antisense strand and between position 20 and 21 of the sense strand; and AL-DUP 5181 bears 2'-O-Me modifications in positions 4, 6, 8, 12, 14, and 20 of its sense strand and in positions 1, 6, 7, 13, 15, and 17 of its antisense strand, and phosphorothioate linkages between positions 21 and 22, and 22 and 23, of the antisense strand and between position 20 and 21 of the sense strand.

The nucleotide sequences of siRNA duplexes AL-DUP 5048, AL-DUP 5167, AL-DUP 5168, AL-DUP 5169, AL-DUP 5170, AL-DUP 5182, and AL-DUP 5183 are identical except that:

AL-DUP 5048 consists entirely of unmodified nucleotides;

AL-DUP 5167 bears 2'-O-Me groups in positions 21 and 22 and phosphorothioate linkages between positions 21 and 22, and 22 and 23, of the antisense strand, and a cholesterol moiety conjugated to the 3'-end of the sense strand;

AL-DUP 5168 bears 2'-O-Me groups in positions 3, 6, 8, 11, 15, and 18 of its sense strand and positions 2, 3, 6, 8, 10, 13, 15, 18, and 21 of its antisense strand, phosphorothioate linkages between positions 21 and 22, and 22 and 23, of the antisense strand, and a cholesterol moiety conjugated to the 3'-end of the sense strand;

AL-DUP 5169 bears 2'-O-Me groups in positions 2, 3, 6, 8, 10, 13, 15, 18, and 21 of its antisense strand, phosphorothioate linkages between positions 21 and 22, and 22 and 23, of the antisense strand, and a cholesterol moiety conjugated to the 3'-end of the sense strand;

AL-DUP 5170 bears 2'-O-Me modifications in positions 3, 6, 8, 11, 15, and 18 of its sense strand and in positions 21 and 22 of its antisense strand, phosphorothioate linkages between positions 21 and 22, and 22 and 23, of the antisense strand, and a cholesterol moiety conjugated to the 3'-end of the sense strand;

AL-DUP 5182 bears 2'-O-Me modifications in positions 3, 6, 8, 11, 15, and 18 of its sense strand and in positions 21 and 22 of its antisense strand, and phosphorothioate linkages between positions 21 and 22, and 22 and 23, of the antisense strand and between position 20 and 21 of the sense strand; and AL-DUP 5183 bears 2'-O-Me modifications in positions 3, 6, 8, 11, 15, and 18 of its sense strand and in positions 2, 3, 6, 8, 10, 13, 15, 18, and 21 of its antisense strand, and phosphorothioate linkages between positions 21 and 22, and 22 and 23, of the antisense strand and between position 20 and 21 of the sense strand.

Stability of the siRNAs listed in Table 10 was tested in mouse and 95% human serum. Mouse serum was obtained from Sigma (Sigma-Aldrich Chemie GmbH, Taufkirchen, Germany, cat. No. M5905) or Charles River (Charles River Laboratories, Sulzfeld, Germany, cat. No. MASER). Assay results reported herein were consistent among the different serum sources tested. To test the stability of the modified siRNA in human serum, blood from eight human volunteers (270 mL) was collected and kept at room temperature for 3 hours. The blood pool was then centrifuged at 20° C. and 3000 rcf using Megafuge 1.0 (Heraeus Instruments, Kendro Laboratory Products GmbH, Langenselbold) to separate serum from the cellular fraction. The supernatant was stored in aliquots at −20° C. and used as needed. Human serum obtained from Sigma (Sigma-Aldrich Chemie GmbH, Taufkirchen, Germany, cat. No. H1513) was used in control assays.

Double stranded RNAs (300 pmol, ca. 4.2 µg) dissolved in 6 µl PBS were added to 60 µl human serum, and the mixture was incubated at 37° C. for varying extents of time, e.g. 0, 15, or 30 minutes, or 1, 2, 4, 8, 16, or 24 hours. Subsequently, the whole tube containing the RNA/serum solution was frozen in liquid nitrogen and stored at −80° C.

For analysis of non-cholesterol conjugated siRNAs, the frozen samples were placed on ice and 450 µl of 0.5 M NaCl was added. After complete thawing, the solution was transferred to Phase-Lock Gel tubes (Eppendorf, Hamburg, Germany; cat. No. 0032 005.152), mixed with 500 µl 50% phenol, 48% chloroform, 2% isoamylacohol (Carl Roth GmbH & Co KG, Karlsruhe, Germany, cat. No. A156.2), and an additional 300 µl Chloroform were added. The tubes were vortexed vigorously for 30 seconds and subsequently centrifuged for 15 min at 16,200 rcf at 4° C. The aqueous supernatant was transferred to a fresh tube and mixed with 40 µl 3M Na-acetate pH 5.2, 1 µl GlycoBlue (Ambion, Tex., USA; cat. No. 9516) and 1 ml Ethanol 95%. RNA was precipitated overnight at −20° C.

Cholesterol-conjugated siRNAs were isolated by hot phenol-extraction in presence of SDS (Sodium Dodecylsulfate). The serum sample (66 µl) was mixed with 200 µl RNA buffer (0.5% SDS, 10 mM EDTA, 10 mM Tris pH7.5) and 200 µl water-saturated phenol (Carl Roth GmbH & Co KG Karlsruhe, Germany; cat. No. A980.1). The reaction tube was incubated for 20 min at 65° C. In order to achieve phase separation, the tubes were placed on ice for 5 min and subsequently centrifuged for 10 min at 16,200 rcf at 4° C. The aqueous phase was transferred to a fresh tube. The remaining phenol phase was extracted a second time with 150 µl RNA potion and vigorous vortexing for 10 sec. The tubes were placed on ice for 2 min and then centrifuged for 10 min at 16,200 rcf at 4° C. The aqueous phase of the second extraction was transferred and combined with the supernatant of the first extraction. The RNA was precipitated by adding 2 µl GlycoBlue (Ambion, Austin, Tex., USA; Cat. No. 9516) and 1 ml Ethanol 95%. Precipitation of RNA was brought to completion overnight at −20° C.

Isolated RNA was analyzed by denaturing gel electrophoresis. Tubes containing the precipitated RNA were centrifuged for 10 min at 16,200 rcf at 4° C. The supernatant was removed and discarded. The RNA pellet was washed with 400 µl 70% Ethanol, and re-pelleted by centrifugation for 5 min at 16,200 rcf at 4° C. All liquid was removed and the pellet was dissolved in 20 µl STOP buffer (95% formamide, 5% EDTA 0.5M, 0.02% xylene cyanol). The samples were boiled for 3 min at 92° C. and chilled quickly on ice. 10 µl were loaded on a denaturing 14% polyacrylamide gel (6M Urea, 20% formamide, Carl Roth GmbH & Co KG Karlsruhe, Germany). The RNA was separated for about 2 h at 45 mA. RNA bands were visualized by staining with the "stains-all" reagent (Sigma-Aldrich Chemie GmbH, Steinheim, Germany, cat. no. E9379) according to manufacturer's instructions.

Figure 3:
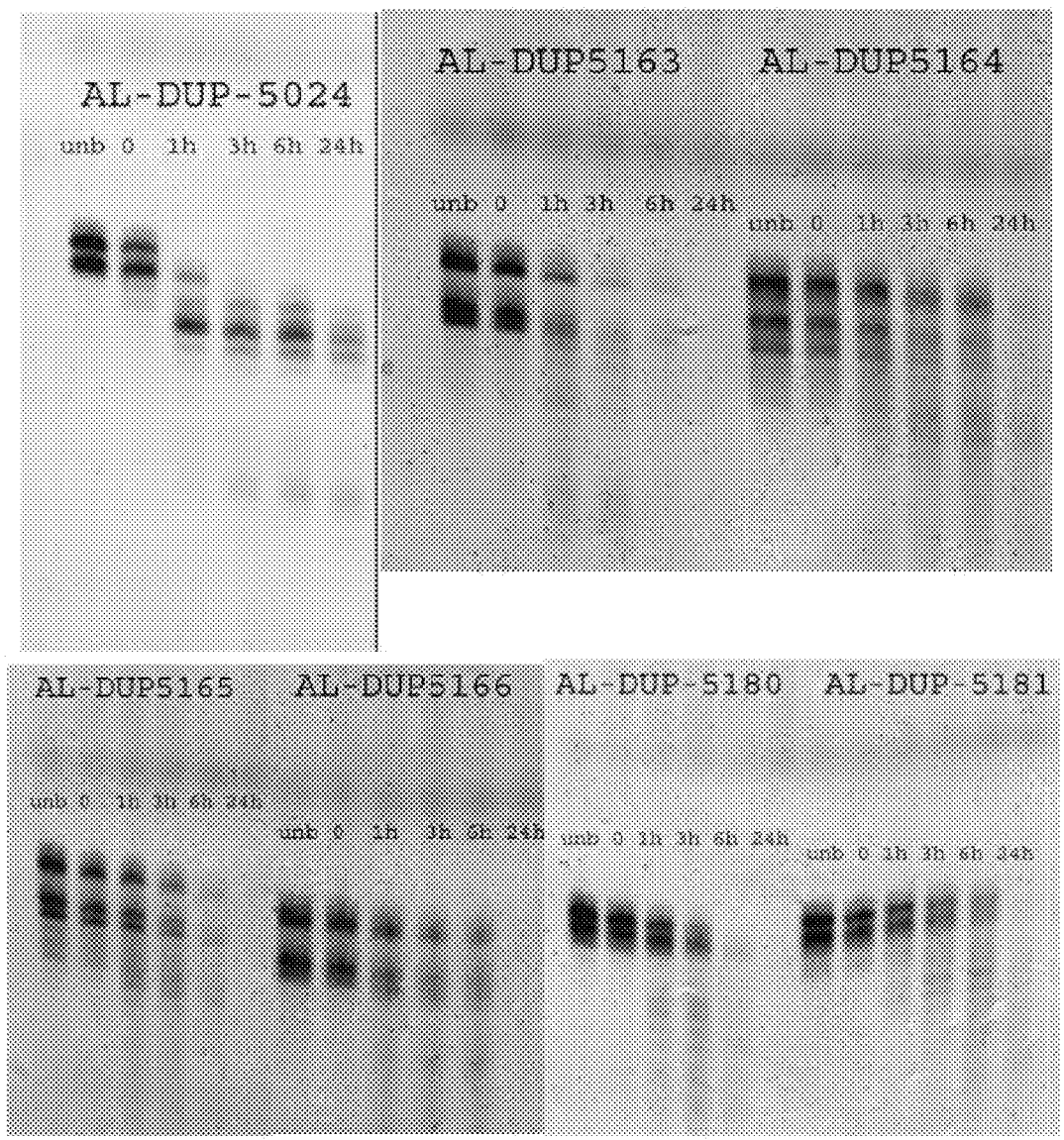
FIG. 3 is a panel of polyacrylamide gels depicting the degradation of siRNA duplexes AL-DUP 5024, AL-DUP 5163, AL-DUP 5164, AL-DUP 5165, AL-DUP 5166, AL-DUP 5180, and AL-DUP 5181 by mouse serum nucleases. siRNA duplexes were incubated in mouse serum for 0, 1, 3, 6 or 24 hours. The lanes marked "unb" represent an untreated control.
Figure 4:
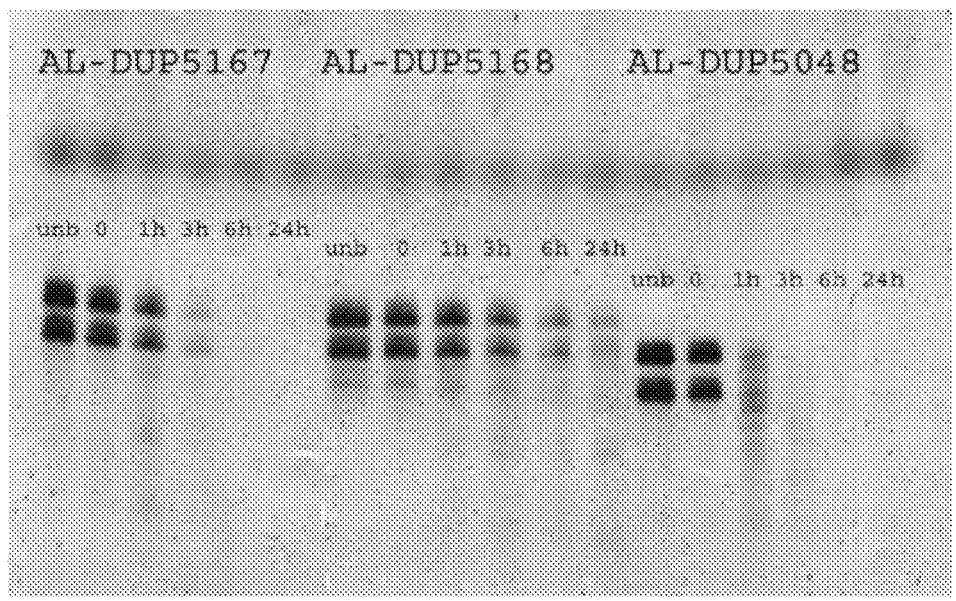
FIG. 4 is a panel of polyacrylamide gels depicting the degradation of siRNA duplexes AL-DUP 5167, AL-DUP 5168, AL-DUP 5048, AL-DUP 5169, AL-DUP 5170, AL-DUP 5182, and AL-DUP 5183 by mouse serum nucleases. siRNA duplexes were incubated in mouse serum for 0, 1, 3, 6 or 24 hours. The lanes marked "unb" represent an untreated control.
Figure 4:
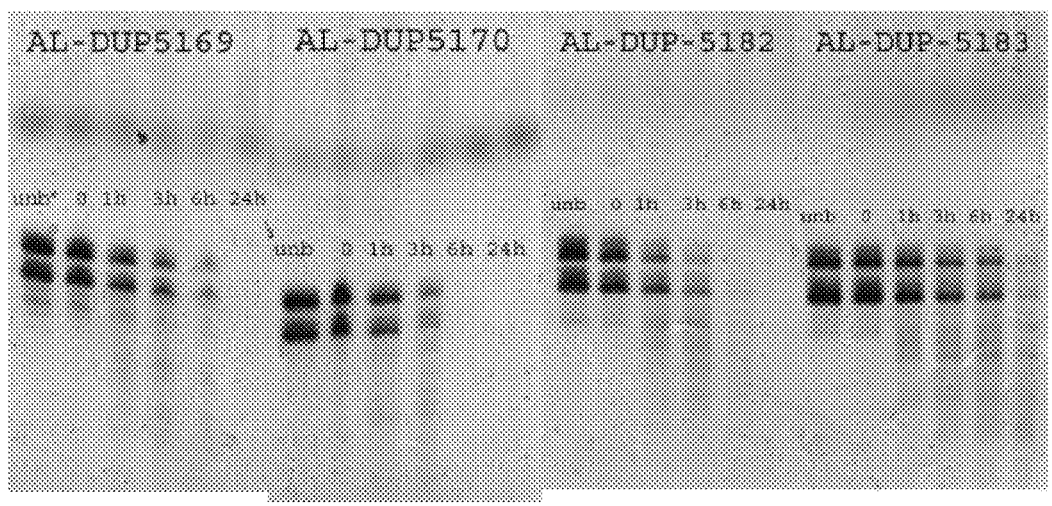
Figure 5A:
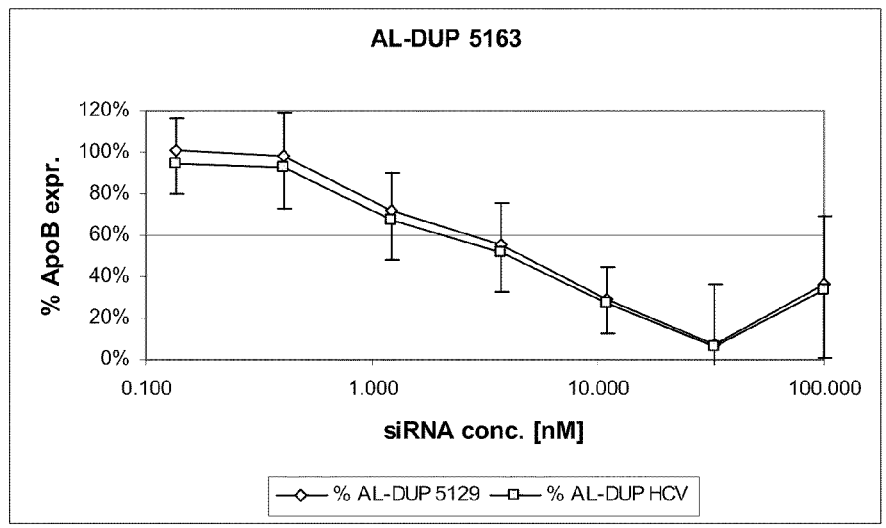
FIG. 5A is a dose-response plot of ApoB protein secretion into supernatant by cultured human HepG2 cells incubated with media containing 100, 33, 11, 3.7, 1.2, 0.4, 0.14, or 0.05 nM of ApoB-specific siRNA duplex AL-DUP 5163. The response is expressed as the ratio of ApoB protein concentrations in the supernatant of cells treated with the ApoB-specific siRNA duplex to the ApoB concentration in the supernatant of cells treated with an unspecific control siRNA duplex with (AL-DUP 5129, diamonds) or without (AL-DUP HCV, squares) cholesterol-conjugation.
Figure 5B:
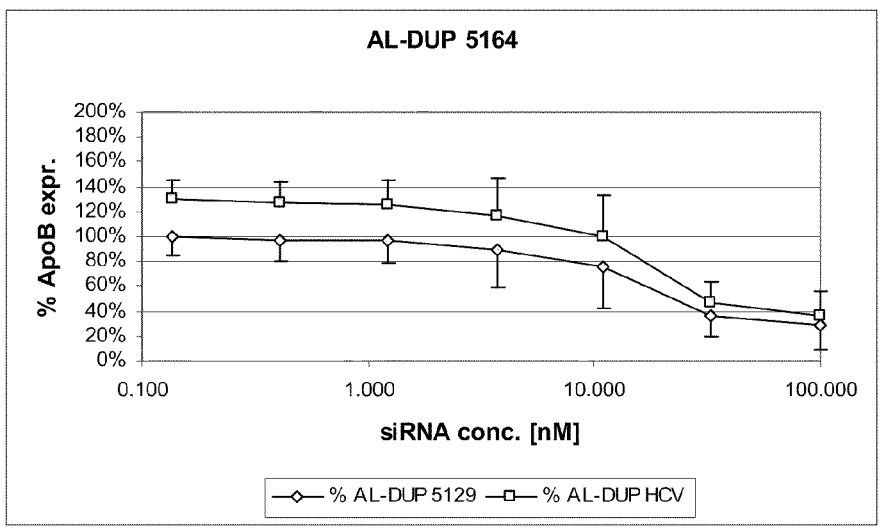
FIG. 5B is a dose-response plot of ApoB protein secretion according to the method described in FIG. 5A. The HepG2 cells were incubated with the siRNA duplex 5164 at the concentration ranges described for FIG. 5A.
Figure 5C:
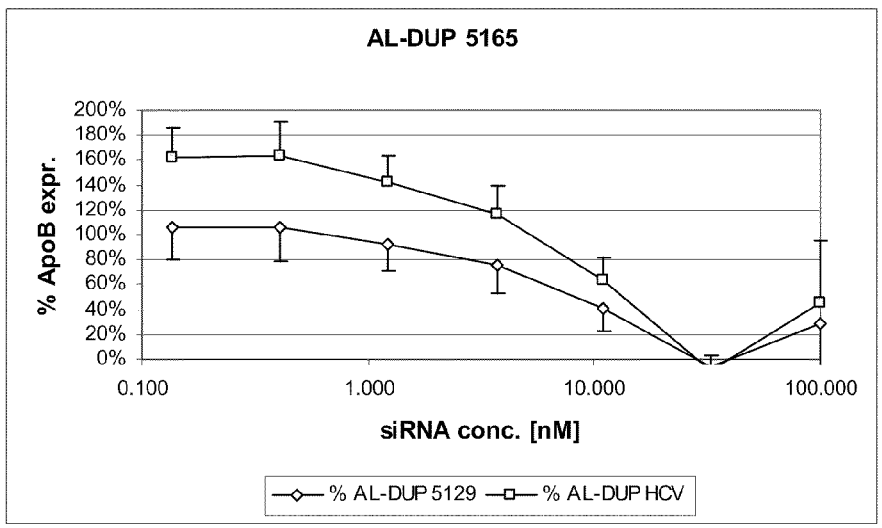
FIG. 5C is a dose-response plot of ApoB protein secretion according to the method described in FIG. 5A. The HepG2 cells were incubated with the siRNA duplex 5165 at the concentration ranges described for FIG. 5A.
Figure 5D:
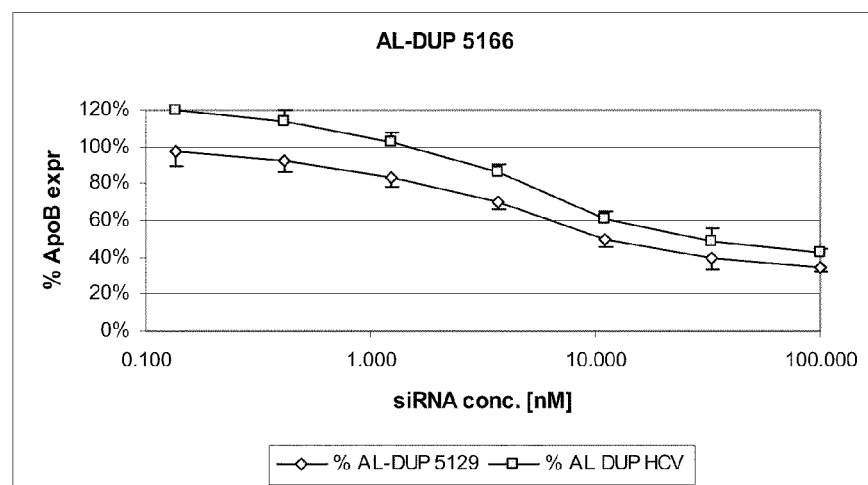
FIG. 5D is a dose-response plot of ApoB protein secretion according to the method described in FIG. 5A. The HepG2 cells were incubated with the siRNA duplex 5166 at the concentration ranges described for FIG. 5A.
Figure 5E:
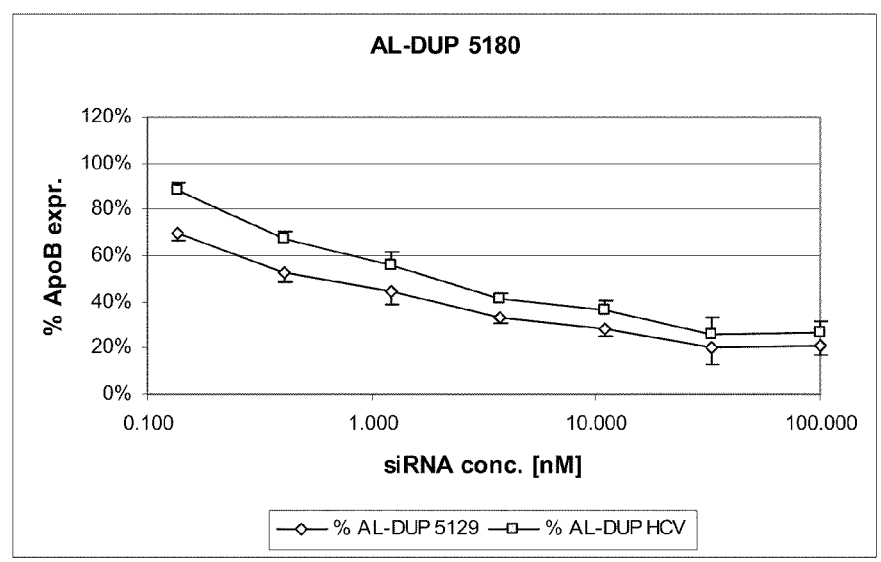
FIG. 5E is a dose-response plot of ApoB protein secretion according to the method described in FIG. 5A. The HepG2 cells were incubated with the siRNA duplex 5180 at the concentration ranges described for FIG. 5A.
Figure 5F:
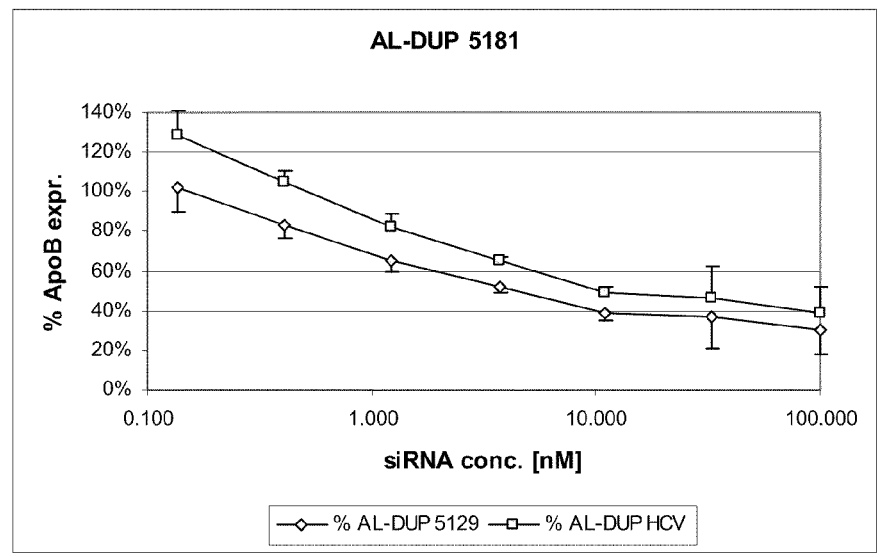
FIG. 5F is a dose-response plot of ApoB protein secretion according to the method described in FIG. 5A. The HepG2 cells were incubated with the siRNA duplex 5181 at the concentration ranges described for FIG. 5A.
Figure 5G:
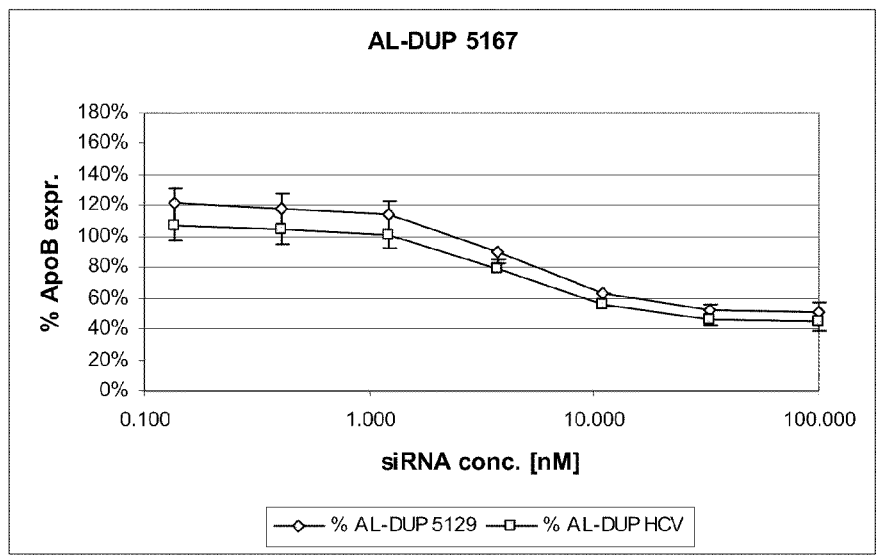
FIG. 5G is a dose-response plot of ApoB protein secretion according to the method described in FIG. 5A. The HepG2 cells were incubated with the siRNA duplex 5167 at the concentration ranges described for FIG. 5A.
Figure 5H:
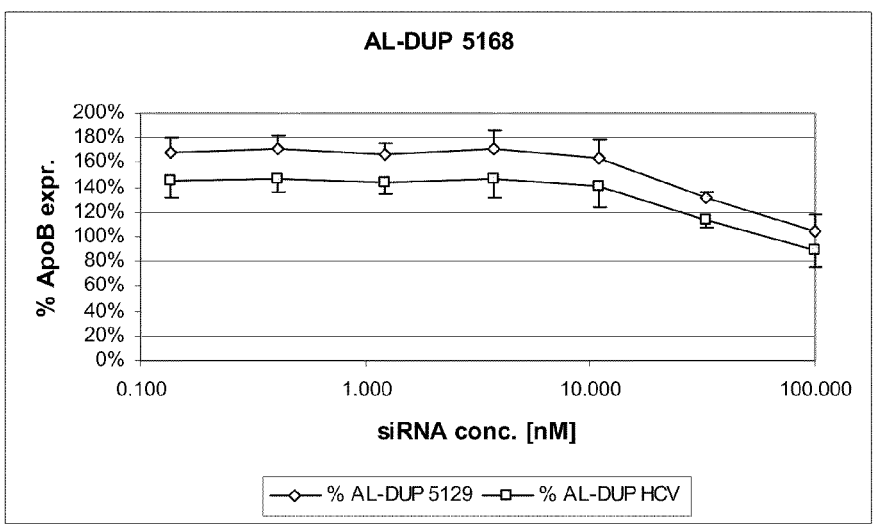
FIG. 5H is a dose-response plot of ApoB protein secretion according to the method described in FIG. 5A. The HepG2 cells were incubated with the siRNA duplex 5168 at the concentration ranges described for FIG. 5A.
Figure 5I:
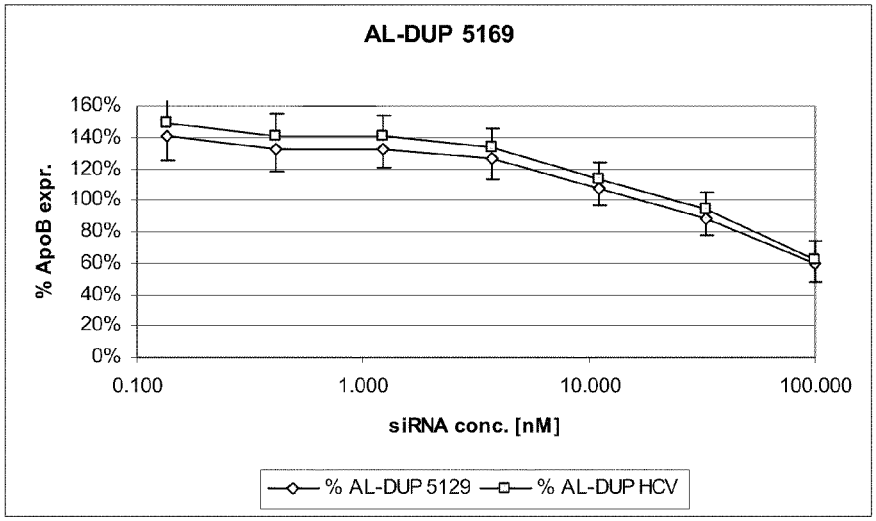
FIG. 5I is a dose-response plot of ApoB protein secretion according to the method described in FIG. 5A. The HepG2 cells were incubated with the siRNA duplex 5169 at the concentration ranges described for FIG. 5A.
Figure 5J:
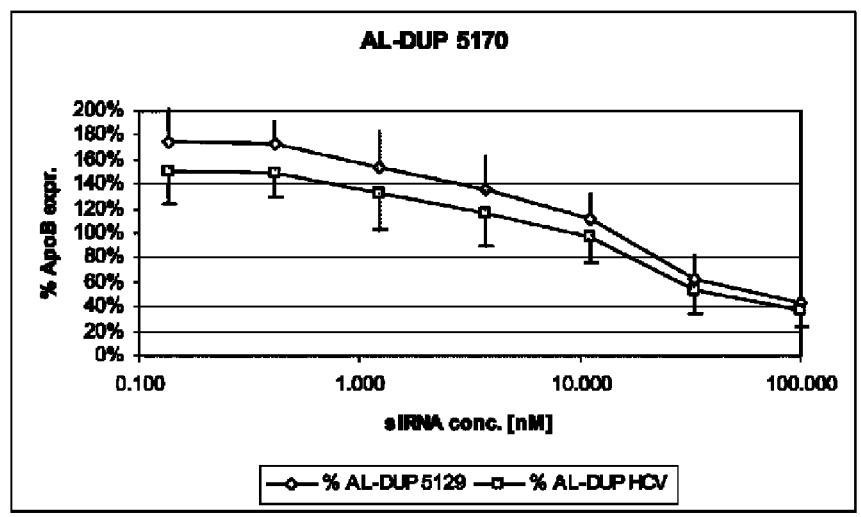
FIG. 5J is a dose-response plot of ApoB protein secretion according to the method described in FIG. 5A. The HepG2 cells were incubated with the siRNA duplex 5170 at the concentration ranges described for FIG. 5A.
Figure 5K:
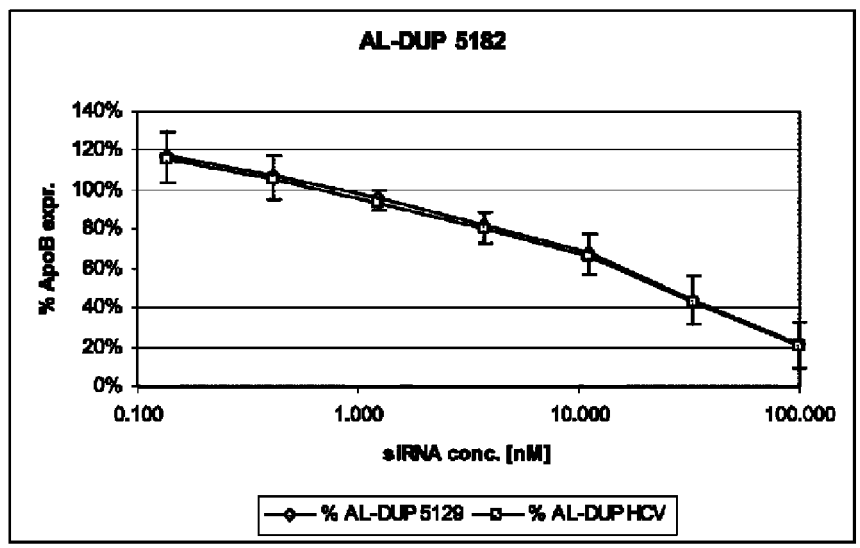
FIG. 5K is a dose-response plot of ApoB protein secretion according to the method described in FIG. 5A. The HepG2 cells were incubated with the siRNA duplex 5182 at the concentration ranges described for FIG. 5A.
Figure 5L:
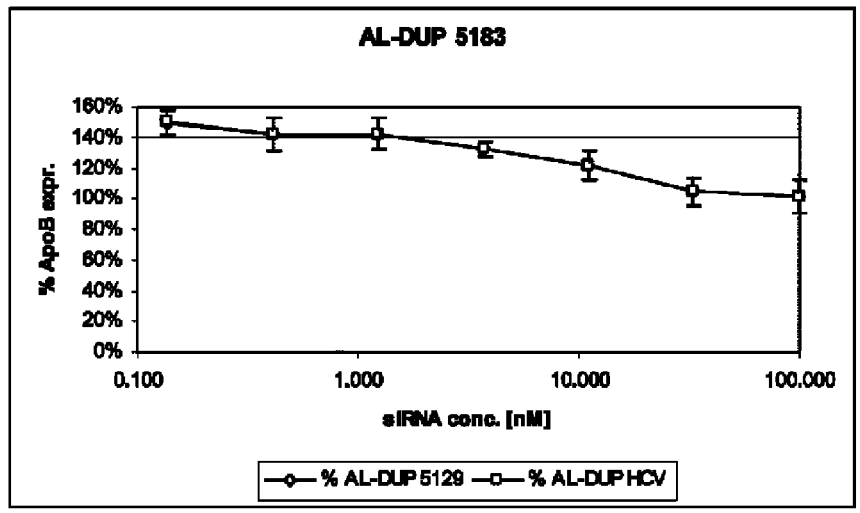
FIG. 5L is a dose-response plot of ApoB protein secretion according to the method described in FIG. 5A. The HepG2 cells were incubated with the siRNA duplex 5183 at the concentration ranges described for FIG. 5A.

While the unmodified AL-DUP 5024 was almost completely degraded after 1 h of incubation with mouse and human serum, the modified siRNAs were more resistant to degradation (see FIG. 3). Following electrophoretic separation, full length RNA was stained with stains-all reagent for up to 3 hours for AL-DUP 5163, and up to 6 hours of incubation for AL-DUP 5164, AL-DUP 5165, AL-DUP 5166, AL-DUP 5180, and AL-DUP 5181. The greatest stabilizing effect was seen in AL-DUP 5164, AL-DUP 5166, and AL-DUP 5181, indicating that the modification of sites prone to degradation in the sense strand was most effective. Additional modification of the antisense strand imparted only a small additional stabilizing effect. (See FIG. 3)

Similarly, the unmodified AL-DUP 5048 was almost completely degraded after 1 h of incubation with mouse serum, while the modified dsRNAs were less sensitive to degradation. Following electrophoretic separation, full length RNA was stained with the stains-all reagent after up to 3 hours for AL-DUP 5167, AL-DUP 5170, and AL-DUP 5182, and up to 6 hours for AL-DUP 5169, and up to 24 hours for AL-DUP 5168 and AL-DUP 5183. (See FIG. 3)

The siRNA duplexes listed in Table 10 were tested for their efficacy in reducing ApoB protein secretion into supernatant by cultured HepG2 cells in order to select the most active duplexes for further examination in vivo.

The silencing activity of cholesterol modified siRNAs specific for ApoB in in vitro assays in HepG2 cells was comparable to that of unmodified ApoB-specific siRNAs. At 200 nM concentrations the two unconjugated siRNAs AL-DUP 5024 and AL-DUP 5048 reduced murine ApoB mRNA levels by 84±9% and 72±9%, respectively, whereas the corresponding conjugated and modified siRNAs AL-DUP 5167 and AL-DUP 5163 had an inhibitory activity of 61±8% % and 68±9%, respectively.

FIGS. 5A through 5L show dose-response curves of ApoB protein secretion into supernatant of cultured human HepG2 cells incubated with media containing 100, 33, 11, 3.7, 1.2, 0.4, 0.14, or 0.05 nM of the ApoB-specific siRNA duplexes. The response is expressed as the ratio of ApoB protein concentrations in the supernatant of cells treated with the ApoB-specific siRNA duplex to the ApoB concentration in the supernatant of cells treated with an unspecific control siRNA duplex. On the basis of these results, AL-DUP 5163, AL-DUP 5165, AL-DUP 5166 and AL-DUP 5167 were chosen for testing in mice (see results below).

Example 7

Modified siRNA Duplexes Reduced ApoB mRNA Amounts in Tissue Sections from Liver and Jejunum, and ApoB Protein's Cholesterol Levels in Serum of Male C57Bl/6 Mice Bolus dosing of siRNAs in mice was performed by tail vein injection using a 27 G needle. SiRNAs were dissolved in PBS at a concentration allowing the delivery of the intended dose in 8 µl/g body weight. Mice were kept under an infrared lamp for approximately 3 min prior to dosing to ease injection.

Pre-treatment blood samples were collected several days before dosing by collecting 4-7 drops from the tail vein. Upon sacrifice by $CO_2$-asphyxiation, ca. 0.7 ml blood was collected by heart puncture, the liver and jejunum were collected, and tissue aliquots of 20-40 mg were frozen in liquid nitrogen and stored at −80° C. until analysis.

ApoB100 mRNA levels were measured by branched-DNA-assay as described above. Triplicate samples of frozen tissue sections (liver or jejunum) of about 10-30 mg each were homogenized by sonication (Bandelin Sonopuls HD 2070, BANDELIN electronic GmbH & Co. KG, Berlin, Germany) in 1 ml of Tissue and Cell Lysis solution (Epicentre, Madison, Wis., USA, cat. No. MTC096H) containing 84 µg/ml Proteinase K (Epicentre, Madison, Wis., USA, cat. No. MPRK092) using 3-9 pulses of 0.9 sec each at an amplitude of ca. 150 µm. Lysates were kept at −80° C. for at least 12 h (overnight) before analysis.

Frozen lysates were thawed at room temperature, and ApoB and GAPDH mRNA quantified using the Quantigene Explore Kit according to manufacturer's instructions. Nucleic acid sequences for Capture Extender (CE), Label Extender (LE) and blocking (BL) probes were selected from the nucleic acid sequences of ApoB and GAPDH with the help of the QuantiGene ProbeDesigner Software 2.0 (Genospectra, Fremont, Calif., USA, cat. No. QG-002-02). Probe nucleotide sequences used in ApoB quantization are shown in Table 4. Probe nucleotide sequences used in GAPDH quantization are shown in Table 6.

The ratio of ApoB mRNA to GAPDH mRNA in tissue samples was averaged over each treatment group and compared to an untreated control group or a control group treated with an unrelated siRNA duplex.

ELISA assays were performed to quantitate the amount of ApoB 100 protein in mouse serum. To perform the assay, a 96 well plate was coated with 100 µl of the mouse ApoB-100-specific monoclonal antibody LF3 (25 µg/ml; Zlot, C. H. et al., J. Lipid Res. 1999, 40:76-84) and the plate was incubated for 2 hours at 37° C. The plate was washed three times with phosphate buffered saline (PBS) (PS Dulbecco without $Ca^{2+}$, $Mg^{2+}$, Biochrom AG, Berlin, Germany, cat. No. L182-05), and then the remaining binding sites were blocked by adding 300 µl PBS containing 3% bovine serum albumin (BSA) (Carl Roth GmbH & Co KG, Karlsruhe, Germany, cat. no. 8076.2) to each well. Plates were incubated for 1 hour at room temperature. The plate was then washed 5 times with PBS. 0.2 µl mouse serum diluted in 100 µl PBS containing 0.1% Tween (Carl Roth GmbH & Co KG, Karlsruhe, Germany, cat. No. 9127.1) and 3% BSA was added to each well. After an incubation of 2 hours at 37° C. the plate was washed 5 times with PBS. 100 µl of a 1:500 dilution of the polyclonal rabbit anti-mouse apolipoprotein B48/100 antibody (Acris Antibodies GmbH, Hiddenheim, Germany, cat. no. BP2050) was added to the wells and incubated for 2 hours at 37° C. After washing the plate 5 times with PBS, 100 µl of a donkey anti-rabbit IgG conjugated to horse radish peroxidase (Santa Cruz Biotechnology, Santa Cruz, Calif., USA, cat. no. sc2004) was added and incubated for 1 hour at 37° C. The plate was washed 5 times with PBS and wells were incubated with 0.9 mg/ml OPD (o-phenylendiamine dihydrochloride, Merck Biosciences GmbH, Bad Soden, Germany cat. No. 523121) in 24 mmol/L citric acid buffer (Sigma-Aldrich, Taufkirchen, Germany, cat. no. C1909-1KG), pH 5.0 containing 0.03% hydrogen peroxide (Merck Biosciences GmbH, Bad Soden, Germany, cat. No. 386790). The enzyme reaction was stopped by adding 0.5 mol/L $H_2SO_4$ (Merck KgaA, Darmstadt, Germany, cat. No. 100731) and absorbance at 490 nm was measured on a spectrophotometer (Perkin Elmer Wallac Victor3 1420 multilabel reader, PerkinElmer LAS GmbH, Rodgau, Germany).

Total serum cholesterol in mouse serum was measured using the Cholesterol FS reagent kit (DiaSys Diagnostic Systems GmbH, Holzheim, Germany) according to manufacturer's instructions. Measurements were taken on a spectral photometer (DU 640B, Beckman Coulter GmbH, Unterschleißheim, Germany).

S1-nuclease protection assay were used to detect siRNAs in liver and jejunum tissue and in serum following injections. Small pieces (10-30 mg) of animal tissue were homogenized as described above for the branched-DNA assay. These lysates were either processed immediately, or stored at −80° C. and thawed at room temperature prior to assay performance. 100 µl lysate was transferred to a fresh reaction tube and mixed with 200 µl STE (Sodium chloride-TRIS-EDTA buffer; 500 mM NaCl, 9 mM Tris pH 7.5, 0.9 mM EDTA) and 200 µl phenol (TRIS-EDTA saturated phenol, Roti-phenol, Carl Roth GmbH & Co KG, Karlsruhe, Germany, cat. no. 0038.1). The tubes were vigorously mixed on a Vortex Genie 2 (Scientific Industries, Inc., Bohemia, N.Y., USA, cat. no. SI-0256) at maximum speed for 30 seconds, and subsequently centrifuged for 10 min at 16,200 rcf and 4° C. About 310 µl aqueous supernatant was carefully aspired and transferred to a new reaction tube, mixed with 50 µg E. coli tRNA (Roche Diagnostics, Penzberg, Germany; cat. No. 109 541) and 900 µl Ethanol 95%. Precipitation of RNA was continued over night at −20° C.

DNA probes for use in the S1-nuclease protection assays were radioactively labelled. Probes of 25 to 27 nucleotides length corresponded to the 21 nucleotide sense-strand sequence of the siRNA molecules, but contained an additional 4 to 6 nucleotides at their 3'-end serving as non-complementary extension. The DNA oligonucleotides probes were phosphorylated with $\gamma$-$^{32}$P ATP to introduce a radioactive phosphate group at their 5'-end. Fifteen picomoles of the respective probe were mixed with 50 µCi of $\gamma$-$^{32}$P ATP (Amersham GE-Healthcare, Freiburg, Germany, cat. no. AA0018) and 10 U Polynucleotide kinase (New England Biolabs, Frankfurt, Germany, M0201S) were mixed in a total volume of 50 µl Polynucleotide kinase buffer (New England Biolabs, Frankfurt, Germany, cat. no. M0201S). This solution was incubated at 37° C. for 1 hour. The labelling reaction was terminated by passing the reaction mixture through a Microspin G-25 desalting column following instructions by the manufacturer (Amersham GE-Healthcare, Freiburg, Germany, cat. no. 27-5325-01). The resulting probe solutions were used within 1-3 days.

To detect siRNAs from mouse tissue lysates, precipitated total RNA from the lysates was centrifuged for 10 min at 16,200 rcf and 4° C. The supernatant was carefully removed and discarded while keeping the nucleic acid pellet. This pellet was first resuspended in 50 µl S1-hybridization buffer (300 mM NaCl, 1 mM EDTA, 38 mM HEPES pH 7.0, 0.1% Triton X-100) and then 1 µl of radioactive DNA probe solution was added. The hybridization reaction mixture was heated to 92° C. for 2 min. The reaction tubes were immediately transferred to a heating block kept at 37° C. and further incubated for 30 min. The hybridization was continued at room temperature for an additional 2 hours.

For the determination of siRNA concentrations in serum, 1 µl of serum was mixed with 50 µl S1-hybridization buffer and 1 µl of radioactive DNA probe, and the hybridization continued as above.

The following probes were used:
For AL-DUP 3001 and AL-DUP 5386:

5'-GAACTGTGTGTGAGAGGTCCTTCTT-3' SEQ. ID NO. 265

For AL-DUP 5311

5'-GTGATCAGACTCAATACGAATTCTTCTT-3' SEQ. ID NO. 266

For siRNAs derived from AL-DUP 5048 (AL-DUP 5048, AL-DUP 5167, AL-DUP 5168, AL-DUP 5169, AL-DUP 5170, AL-DUP 5182, AL-DUP 5183, AL-DUP 5385, AL-DUP 5546)

5'-GTCATCACACTGAATACCAATTCTTCT-3' SEQ. ID NO. 267

For siRNAs derived from AL-DUP 5024 (AL-DUP 5024, AL-DUP 5163, AL-DUP 5164, AL-DUP 5165, AL-DUP 5166, AL-DUP 5180, AL-DUP 5181)

5'-AGGTGTATGGCTTCAACCCTGTCTTCT-3' SEQ. ID NO. 268

For siRNAs derived from AL-DUP 5002 (AL-DUP 5536, AL-DUP 5537)

5'-GATTGATTGACCTGTCCATTCTCTTCTT-3' SEQ. ID NO. 245

For siRNAs derived from AL-DUP 5035 (AL-DUP 5538, AL-DUP 5539)

5'-CACCAACTTCTTCCACGAGTCTCTTCTT-3' SEQ. ID NO. 246

For siRNAs derived from AL-DUP 5089 (AL-DUP 5540, AL-DUP 5541)

5'-GAGTTTGTGACAAATATGGGCTCTTCTT-3' SEQ. ID NO. 247

For siRNAs derived from AL-DUP 5097 (AL-DUP 5542, AL-DUP 5543)

5'-CTTTACAAGCCTTGGTTCAGTTCTTCTT-3' SEQ. ID NO. 248

For siRNAs derived from AL-DUP 5098 (AL-DUP 5544, AL-DUP 5545)

5'-GGAATCTTATATTTGATCCAATCTTCT-3' SEQ. ID NO. 250

In addition, two probes hybridizing with micro-RNAs endogenously expressed in liver (miRNA122) and jejunum (miRNA143) were used as a loading control.
For miRNA 122:

5'-AAACACCATTGTCACACTCCATCTTCTT-3' SEQ. ID NO. 269

For miRNA 143:

5'-GAGCTACAGTGCTTCATCTCATCTTCTT-3' SEQ. ID NO. 270

After hybridization, 450 µl of S1-nuclease digestion mix was added to each tube (450 µl S1-reaction mix: 333 mM NaCl, 2.2 mM Zn-acetate, 66.7 mM Na-acetate pH 4.5, 0.02% Triton X-100 and 100 U S1-Nuclease; Amersham GE-Healthcare, Freiburg, Germany; cat. no. E2410Y) to degrade any unhybridized probe. The digestion reaction mixture was incubated at 37° C. for 30 min. The reaction digestion was terminated by the addition of 30 µg tRNA (Roche Diagnostics, Penzberg, Germany; 109 541) in 7 µl of 500 mM EDTA, pH 8.0, and 900 µl Ethanol 95%. The protected probes were precipitated at −20° C. over night or at −80° C. for 90 min.

Following precipitation, the protected probes were analyzed by denaturing gel electrophoresis. The precipitated duplexed RNA was centrifuged for 10 min at 16,200 rcf and 4° C. The supernatant was carefully removed and discarded. The pellet was dissolved in 12 µl STOP buffer (95% formamide, 5% EDTA 0.5M, 0.02% xylene cyanol). The tubes were heated to 92° C. for 2 min and then immediately chilled on ice. 4 µl of the solution were loaded per lane of a denaturing sequencing gel (12.5% acrylamide, 1× standard TBE buffer, 19 cm×20 cm×0.4 mm Length×Width×Depth; Rotiphorese DNA sequencing system, Carl Roth GmbH & Co KG, Karlsruhe, Germany, cat. no. A431.1). The gel was run for 45 min at 600 V corresponding to a voltage gradient of approximately 30 V/cm (EPS 3501XL, Amersham Biosciences, Uppsala, Sweden; cat. no. 18-1130-05). The gel was dried on paper and exposed overnight to a general purpose phosphor screen imager (Amersham GE-Healthcare, Freiburg, Germany; cat. no. 63-0034-88). On the following day, radioactive bands were visualized on a Typhoon 9200 high performance imager (Amersham GE-Healthcare, Freiburg, Germany; cat. no. 63-0038-49). Quantitation of radioactive band intensity was performed using the ImageQuant TL software version 2003.01 supplied with Typhoon 9200 imager by comparison to a dilution series of 60, 20, 6.6, and 2.2 fmol of the respective radioactive probe loaded onto the gel.

All animal experiments, except those involving animals transgenic for the expression of human ApoB described below, were carried out in compliance with the regulations of the European Convention for the Protection of Vertebrate Animals used for Experimental and other Scientific Purposes. Male C57Bl/6 mice were obtained from Charles River Laboratories, Sulzfeld, Germany, and acclimatized for at least 5 days before use. Animals were housed at 22±2° C. and 55±10% rel. humidity. Day/night rhythm was 12 hours, changing at 6:00 am (light) and 6:00 pm (dark). Animals were fed Ssniff R/M-H chow (Ssniff Spezialdiäten GmbH, Soest, Germany, cat. No. V1531) ad libitum, unless specifically specified otherwise below.

The following experimental protocols were performed.

A.) Three groups of 7 animals, age 3.5 months, received daily doses of 50 mg/kg on three consecutive days of either AL-DUP 5163, AL-DUP 5166 (sequences see Table 10), or an equivalent amount of carrier, and were sacrificed on the fourth day. Total serum cholesterol, serum ApoB 100 concentration, and liver and jejunum ApoB mRNA levels were determined.

The 2'-O-methyl modification of the nucleotides in positions 4, 6, 8, 12, 14, and 20 in the sense strand of AL-DUP 5166 as compared to the otherwise identical AL-DUP 5163 afforded greater stability to AL-DUP 5166 with respect to its degradation in serum (see FIG. 3). This experiment was designed to test the ability of siRNA specific for mouse ApoB to down-regulate the expression of the ApoB gene in the liver and jejunum of mice, and to lower ApoB protein levels and cholesterol levels in serum. This experiment also tested whether an siRNA bearing 2'-O-Me modifications on its sense strand, which increases its stability in biological serum was more potent in down-regulating the expression of ApoB, than an siRNA lacking the 2'OMe sense strand modification.

ApoB mRNA levels in liver and jejunum tissue were assayed by the branched DNA assay. AL-DUP 5163 was found to lower the levels of ApoB mRNA in samples of liver tissue to 50±13% of the levels present in liver tissue of control animals. Levels of ApoB mRNA in jejunum were lowered to 40±6% of the levels in control animals.

AL-DUP 5166 was found to lower the levels of ApoB mRNA in liver tissue to 59±9% of the mRNA levels in tissue of control animals. Levels of ApoB mRNA in jejunum were lowered to 14±3% of the levels in control animals.

B.) Two groups of 7 animals, age 3.5 months were treated for three consecutive days with daily doses of 50 mg/kg of either AL-DUP 5167 (sequences see Table 10) or an equivalent amount of carrier. The mice were sacrificed on the fourth day. Total serum cholesterol, serum ApoB 100 concentration, and liver and jejunum ApoB mRNA levels were determined.

ApoB mRNA levels were determined by branched DNA assay. AL-DUP 5167 was found to lower the levels of ApoB mRNA present in samples of liver tissue from treated mice to 41±6% of the mRNA levels present in liver tissue of control animals. Levels of ApoB mRNA in jejunum were lowered to 29±9% of the levels in control animals. Serum ApoB protein concentration in mouse sera was essentially unchanged at 101±9% of control levels. Serum cholesterol was lowered to 60±22% of carrier controls.

C.) Three groups of 7 animals, age 2.5 months, received daily doses of 50 mg/kg, on three consecutive days, of AL-DUP 5165 or an equivalent amount of carrier, and were sacrificed on the fourth day. Total serum cholesterol, serum ApoB 100 concentration, and liver ApoB mRNA levels were determined.

The 2'-O-Me modification of the nucleotides in positions 1, 6, 7, 13, 15, and 17 of its antisense strand of AL-DUP 5165 as compared to the otherwise identical AL-DUP 5163 (sequences see Table 10) afforded greater stability to AL-DUP 5165 with respect to its degradation in serum (see FIG. 3), but the stabilizing effect was not quite as strong as seen in AL-DUP 5166. This experiment compared the ability of siRNA specific for mouse ApoB, and bearing stabilizing modifications on the antisense strand, to down-regulate the expression of the ApoB gene in the liver and jejunum of mice, and lower serum ApoB and cholesterol levels. The experiment also tested whether an siRNA modified to possess increased stability in serum was more potent in down-regulating the expression of ApoB.

The branched DNA assay was used to measure ApoB mRNA levels. AL-DUP 5165 was found to lower the levels of ApoB mRNA in liver tissue from treated mice to 68±12% of the mRNA levels present in liver tissue of control animals receiving carrier only. Serum ApoB protein concentration in mouse sera was lowered to 63±6% of control levels. Serum cholesterol was found unchanged at 99±26% of carrier control levels.

D.) Four groups of 6 animals, age 2.5 months, received daily doses of 50 mg/kg, on three consecutive days, of either AL-DUP 5167, AL-DUP 3001, AL-DUP 5311, or an equivalent amount of carrier, and were sacrificed on the fourth day. Total serum cholesterol, serum ApoB 100 concentration, and liver and jejunum ApoB mRNA levels were determined.

The nucleotide sequences of AL-DUP 5167 is shown in Table 10. The sequences of AL-DUP 5311 and AL-DUP 3001 are as follows

```
AL-DUP 5311
Sense:
                                    SEQ. ID No. 271
5'-gugaucagacugaauacgaau(Chol)-3'

Antisense:
                                    SEQ. ID No. 272
5'-auucguauugagucugaucacmamc-3'

AL-DUP 3001
Sense:
                                   (SEQ. ID No. 273)
5'-gaacugugugugagagguccu(Chol)-3'

Antisense:
                                   (SEQ. ID No. 274)
5'-aggaccucucacacacaguucgmcm-3'
```

AL-DUP 5311 represents a mouse ApoB mRNA mismatch siRNA to AL-DUP 5167 where four G/C switches in positions 4, 10, 14, and 19 were made. This siRNA was a negative control for comparison with AL-DUP 5167.

AL-DUP 3001 represents an unrelated control siRNA. The sequence of positions 1 to 21 of the sense strand of AL-DUP 3001 corresponds to nucleotides 1252 to 1272 of cloning vector pGL3-Basic (Promega GmbH, Mannheim, Germany, cat. no. E1751), accession number U47295, and is part of a sequence encoding firefly (*Photinus pyralis*) luciferase. AL-DUP 3001 was meant to serve as an additional negative control to AL-DUP 5167.

This experiment was meant to confirm the earlier findings obtained with AL-DUP 5167, and to further show that the effects seen with AL-DUP 5167 are sequence-specific.

ApoB mRNA levels were determined by branched-DNA assay. AL-DUP 5167 was found to lower the levels of ApoB mRNA in liver tissue from treated mice to 36±11% of the mRNA levels present in liver tissue of control animals. Levels of ApoB mRNA in jejunum were lowered to 27±8% of the levels in control animals. Serum ApoB protein concentration in mouse sera was lowered to approximately 29±16% of carrier control levels. Serum cholesterol levels were essentially unchanged at 73±35%.

AL-DUP 5311 was found to leave the levels of ApoB mRNA in liver tissue from treated mice essentially unchanged at 95±16% of the mRNA levels present in liver tissue of control animals injected with carrier. Levels of ApoB mRNA in jejunum were found essentially unchanged at 120±19% of the levels in control animals. Serum ApoB protein concentration in mouse sera was essentially unchanged at 109±76% of carrier control levels. Serum cholesterol levels were found essentially unchanged at 77±43% of carrier controls.

AL-DUP 3001 was found to leave the levels of ApoB mRNA in liver tissue from treated mice essentially unchanged at 79±22% of the mRNA levels in liver tissue of control animals receiving carrier only. Levels of ApoB mRNA in jejunum were found essentially unchanged at 130±33% of the levels in control animals. Serum ApoB protein concentration in mouse sera was found essentially unchanged at 104±55% of carrier control levels. Serum cholesterol levels were found essentially unchanged at 108±46% of carrier control levels.

E.) Seven groups of six animals, age 2.5 months, received daily doses of 50 mg/kg, on three consecutive days, of either AL-DUP 5167, AL-DUP 3001, AL-DUP 5311, or an equivalent amount of carrier, or daily doses of 10 mg/kg of AL-DUP 5167 on three consecutive days, or daily doses of 2 mg/kg of AL-DUP 5167 on three consecutive days, or a single dose of 50 mg/kg on day 1. The mice were sacrificed on the fourth day. Another group of 6 animals received an osmotic pump implant (Alzet 1007D, ALZET Osmotic Pumps DURECT Corporation, Cupertino, Calif., USA) subcutaneously on their back slightly posterior to the scapulae on day 1. The pump was set to deliver 0.5 µl/hr of a solution of 0.33 mg/µAL-DUP 5167 for 7 days, amounting to a daily dose of approximately 4 mg/kg body weight per day per animal. This group of animals was sacrificed on day 8. Total serum cholesterol, serum ApoB 100 concentration, and liver and jejunum ApoB mRNA levels were determined.

The nucleotide sequence of AL-DUP 5167, AL-DUP 5311 and AL-DUP 3001 are given above.

This experiment was meant to confirm the earlier findings obtained with AL-DUP 5167, using carrier, a mismatched siRNA (AL-DUP 5311), and an unrelated siRNA (AL-DUP 3001) as controls, and to further determine whether bolus intravenous doses of 2 or 10 mg/kg body weight on three consecutive days, or a single dose of 50 mg/kg body weight on day 1, could suffice to elicit the effects seen when dosing 50 mg/kg body weight intravenously on three consecutive days in (C) and (D) above. Furthermore, this experiment set out to compare these dosing regimens with continuous delivery of a lower dose of 4 mg/kg body weight per day over 7 days from an osmotic pump.

At a dose of 50 mg/kg body weight, administered intravenously on three consecutive days followed by sacrifice on day 4, AL-DUP 5167 was found to lower the levels of ApoB mRNA present in samples of liver tissue from treated mice to 69±17% of the mRNA levels present in liver tissue of animals receiving carrier only, and levels of ApoB mRNA in jejunum were lowered to 24±8% of the levels in control animals, as determined by the branched-DNA assay. Serum ApoB protein concentration in mouse sera was lowered to 69±9% of carrier control levels. Serum cholesterol was found essentially unchanged at 95±29% of carrier control levels.

At a dose of 10 mg/kg body weight, administered intravenously on three consecutive days followed by sacrifice on day 4, AL-DUP 5167 was found to leave the levels of ApoB mRNA present in samples of liver tissue from treated mice essentially unchanged at 81±32% of the mRNA levels present in liver tissue of animals receiving carrier only, and levels of ApoB mRNA in jejunum came to 62±13% of the levels in control animals, as determined by the branched-DNA assay. Serum ApoB protein concentration in mouse sera was essentially unchanged at 101±19% of carrier control levels. Serum cholesterol was found essentially unchanged at 101±29% of carrier control levels.

At a dose of 2 mg/kg body weight, administered intravenously on three consecutive days followed by sacrifice on day 4, AL-DUP 5167 was found to leave the levels of ApoB mRNA present in samples of liver tissue from treated mice essentially unchanged at 109±38% of the mRNA levels present in liver tissue of animals receiving carrier only, and levels of ApoB mRNA in jejunum came to 97±21% of the levels in control animals, as determined by the branched-DNA assay. Serum ApoB protein concentration in mouse sera was essentially unchanged at 115±13% of carrier control levels. Serum cholesterol was found essentially unchanged at 114±26% of carrier control levels.

At a dose of 50 mg/kg body weight, administered intravenously once on day 1 followed by sacrifice on day 4, AL-DUP 5167 was found to lower the levels of ApoB mRNA present in samples of liver tissue from treated mice to 41±20% of the mRNA levels present in liver tissue of animals receiving carrier only, and levels of ApoB mRNA in jejunum were lowered to 62±23% of the levels in control animals, as determined by the branched-DNA assay. Serum ApoB protein concentration in mouse sera was lowered to 52±11% of carrier control levels. Serum cholesterol was found essentially unchanged at 95±25% of carrier control levels.

At a dose of 50 mg/kg body weight, administered intravenously on three consecutive days followed by sacrifice on day 4, AL-DUP 5311 was found to leave the levels of ApoB mRNA present in samples of liver tissue from treated mice essentially unchanged at 100±16% of the mRNA levels present in liver tissue of animals receiving carrier only, and levels of ApoB mRNA in jejunum came to 100±20% of the levels in control animals, as determined by the branched-DNA assay. Serum ApoB protein concentration in mouse sera was essentially unchanged at 97±11% of carrier control levels. Serum cholesterol was found essentially unchanged at 129±37% of carrier control levels.

At a dose of 50 mg/kg body weight, administered intravenously on three consecutive days followed by sacrifice on day 4, AL-DUP 3001 was found to leave the levels of ApoB mRNA present in samples of liver tissue from treated mice essentially unchanged at 97±28% of the mRNA levels present in liver tissue of animals receiving carrier only, and levels of ApoB mRNA in jejunum came to 101±16% of the levels in control animals, as determined by the branched-DNA assay. Serum ApoB protein concentration in mouse sera was lowered to 106±6% of carrier control levels. Serum cholesterol was found essentially unchanged at 129±43% of carrier control levels.

At a dose of 4 mg/kg body weight per day over 7 days delivered from an osmotic pump, followed by sacrifice on day 8, AL-DUP 5167 was found to leave the levels of ApoB mRNA present in samples of liver tissue from treated mice essentially unchanged at 79±24% of the mRNA levels present in liver tissue of animals receiving carrier only, and levels of ApoB mRNA in jejunum came to 70±19% of the levels in control animals, as determined by the branched-DNA assay. Serum ApoB protein concentration in mouse sera was lowered to 106±6% of carrier control levels. Serum cholesterol was found essentially unchanged at 129±43% of carrier control levels.

F.) Seven groups of six animals, age 2.5 months, received one bolus dose of 50 mg/kg on day 1 of AL-DUP 5167. A control group of six animals received an equivalent amount of carrier. Groups of animals receiving siRNA were sacrificed 12, 24, 36, 60, 84 and 108 hours post-dosing. The control group receiving carrier was sacrificed 84 hours post-dosing. Liver and jejunum ApoB mRNA levels were determined.

The nucleotide sequence of AL-DUP 5167 is given above.

This experiment was designed to yield the time course of the effects of AL-DUP 5167 on ApoB mRNA levels in liver and jejunum, and on serum ApoB and cholesterol concentrations.

In animals sacrificed 12 hours post dosing of 50 mg/kg AL-DUP 5167 intravenously, 100±32% of the ApoB mRNA levels present in liver tissue of animals receiving carrier only were found in the liver, and 145±78% of the ApoB mRNA levels present in jejunum tissue of animals receiving carrier only were found in the jejunum. Serum ApoB protein concentration in mouse sera was determined to 124±14% of carrier control levels.

In animals sacrificed 24 hours post dosing of 50 mg/kg AL-DUP 5167 intravenously, 85±21% of the ApoB mRNA levels present in liver tissue of animals receiving carrier only were found in the liver, and 84±32% of the ApoB mRNA levels present in jejunum tissue of animals receiving carrier only were found in the jejunum. Serum ApoB protein concentration in mouse sera was determined to 92±52% of carrier control levels.

In animals sacrificed 36 hours post dosing of 50 mg/kg AL-DUP 5167 intravenously, 64±20% of the ApoB mRNA levels present in liver tissue of animals receiving carrier only were found in the liver, and 88±19% of the ApoB mRNA levels present in jejunum tissue of animals receiving carrier only were found in the jejunum. Serum ApoB protein concentration in mouse sera was lowered to 55±12% of carrier control levels.

In animals sacrificed 60 hours post dosing of 50 mg/kg AL-DUP 5167 intravenously, 73±10% of the ApoB mRNA levels present in liver tissue of animals receiving carrier only were found in the liver, and 41±13% of the ApoB mRNA levels present in jejunum tissue of animals receiving carrier only were found in the jejunum. Serum ApoB protein concentration in mouse sera was lowered to 43±16% of carrier control levels.

In animals sacrificed 84 hours post dosing of 50 mg/kg AL-DUP 5167 intravenously, 72±13% of the ApoB mRNA levels present in liver tissue of animals receiving carrier only were found in the liver, and 68±22% of the ApoB mRNA levels present in jejunum tissue of animals receiving carrier only were found in the jejunum. Serum ApoB protein concentration in mouse sera was lowered to 54±15% of carrier control levels.

In animals sacrificed 108 hours post dosing of 50 mg/kg AL-DUP 5167 intravenously, 68±15% of the ApoB mRNA levels present in liver tissue of animals receiving carrier only were found in the liver, and 85±15% of the ApoB mRNA levels present in jejunum tissue of animals receiving carrier only were found in the jejunum. Serum ApoB protein concentration in mouse sera was lowered to 51±8% of carrier control levels.

G.): Five groups of 10 animals, age 2.5 months, received daily doses of 50 mg/kg body weight intravenously on three consecutive days of either AL-DUP 5167, AL-DUP 5385, AL-DUP 5311, AL-DUP 5386 or an equivalent amount of carrier, one group of 7 animals received AL-DUP 5163 by the same dosing regimen, and all animals were sacrificed on the fourth day. Total serum cholesterol, serum ApoB 100 concentration, and liver and jejunum ApoB mRNA levels were determined. In addition, the amount of siRNA present in samples of liver and jejunum was approximated by the S1-nuclease protection assay (see FIG. 6).

The nucleotide sequences of AL-DUP 5167, AL-DUP 5163, and AL-DUP 5311 are given above. The nucleotide sequences of AL-DUP 5385 and AL-DUP 5386 are:

```
AL-DUP 5385
Sense:
5'-gucaucacacugaauaccaau-3'        SEQ. ID NO. 275
Antisense:
5'-auugguauucagugugaugacmamc-3'    SEQ. ID NO. 276

AL-DUP 5386
Sense:
5'-gaacugugugugagagguccu(Chol)-3'  SEQ. ID NO. 277
Antisense:
5'-aggaccucucacacaguucmgmc-3'      SEQ. ID NO. 278
```

AL-DUP 5385 is identical to AL-DUP 5167, except that it bears no cholesterol moiety on the 3'-end of the sense strand, and has a phosphorothioate linkage between positions 20 and 21 of the sense strand. The latter phosphorothioate group was meant to confer similar protection towards exonucleolytic degradation as the phosphorothioate-bearing cholesterol modification (see FIG. 1).

AL-DUP 5386 is identical to AL-DUP 3001, except that the 2'-O-methyl-modification in position 23 of the antisense strand was removed, and a 2'-O-methyl-modification was added in position 21. This was believed to confer superior stabilization towards degradation of AL-DUP 5386 over AL-DUP 3001.

This experiment was designed to confirm results obtained in (E) above, to further compare the activity of the cholesterol-conjugated AL-DUP 5167 to the activity of the otherwise identical but cholesterol-lacking AL-DUP 5385, and to confirm that the lack of ApoB mRNA expression inhibiting activity seen with AL-DUP 3001 was not due to rapid degradation of AL-DUP 3001 in the serum of treated mice.

Figure 6A:
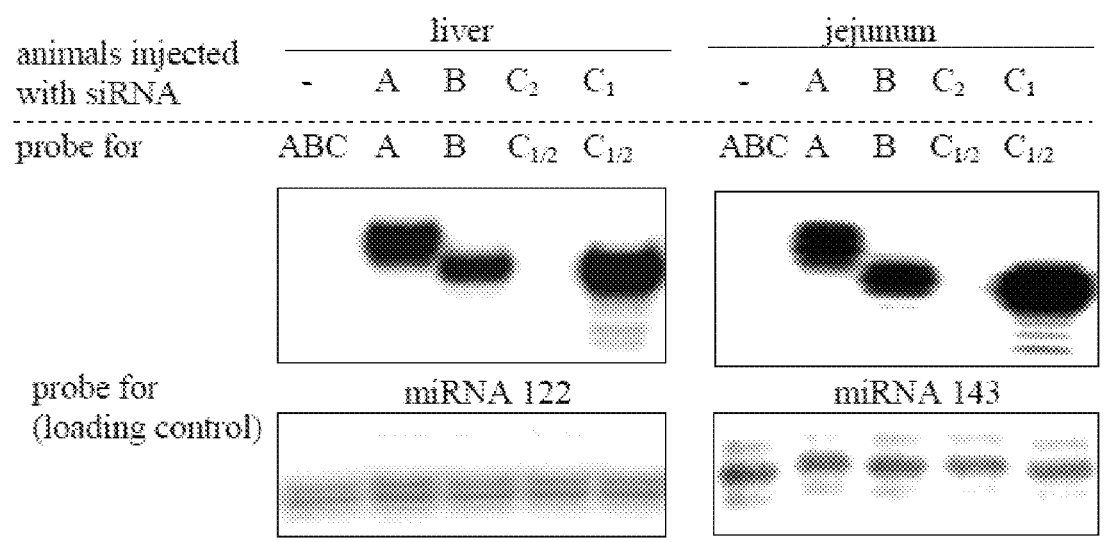
FIG. 6A to D depict, by way of example, results obtained in experiments described in Example 7, (H), below.
Figure 6B:
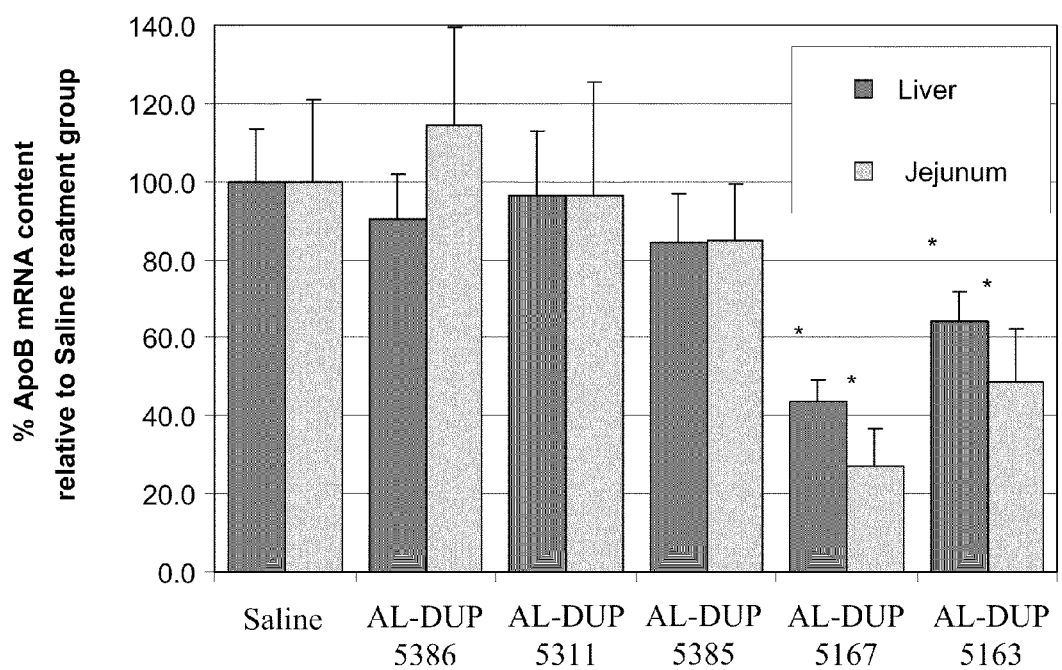
Figure 6C:
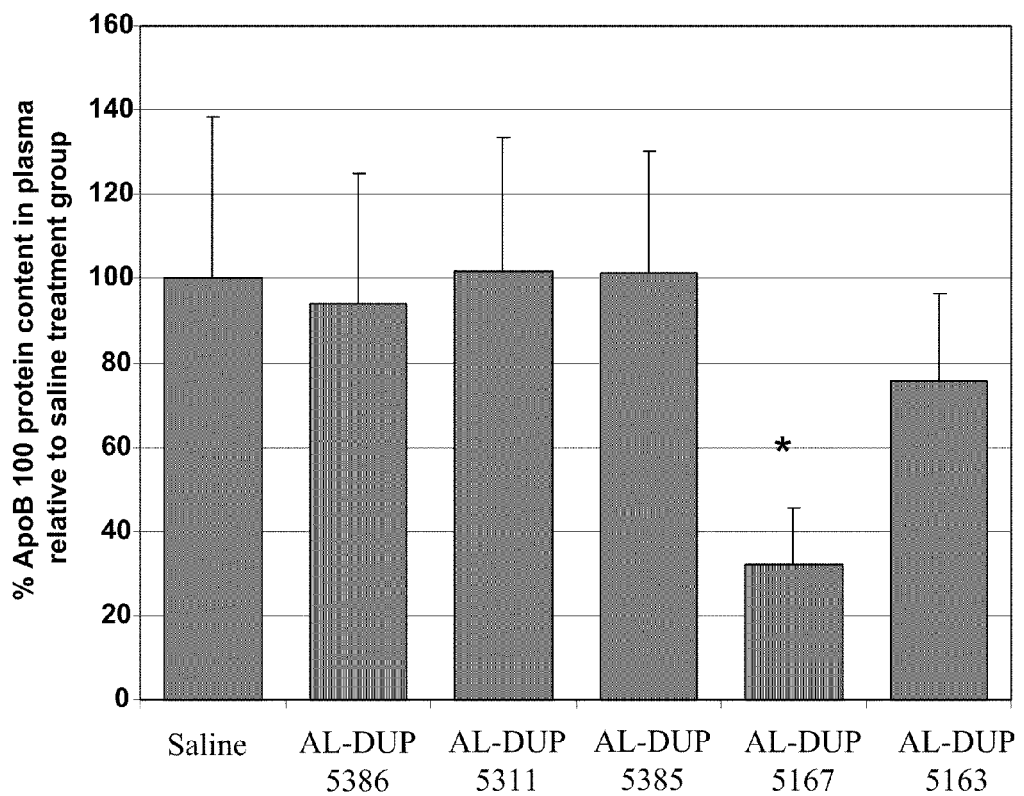
Figure 6D:
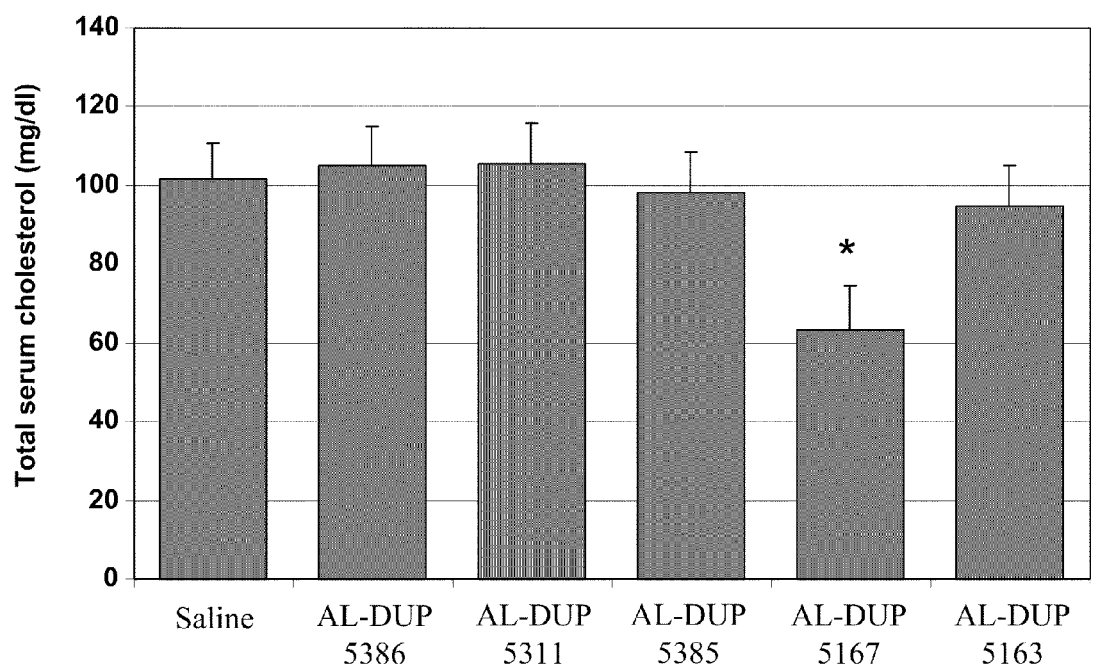

AL-DUP 5167 was found to lower the levels of ApoB mRNA present in samples of liver tissue from treated mice to 43±6% of the mRNA levels present in liver tissue of animals receiving carrier only, and levels of ApoB mRNA in jejunum were lowered to 27±10% of the levels in control animals, as determined by the branched-DNA assay. Serum ApoB protein concentration in mouse sera was lowered to 32±14% of carrier control levels. Serum cholesterol concentration in mouse sera was lowered to 63±11% of carrier control levels. Approx. 100-200 ng/ of AL-DUP 5167 per g tissue was detected in liver and jejunum tissue samples by the S1-nuclease protection assay (FIG. 6A).

AL-DUP 5163 was found to lower the levels of ApoB mRNA present in samples of liver tissue from treated mice to 64±8% of the mRNA levels present in liver tissue of animals receiving carrier only, and levels of ApoB mRNA in jejunum were lowered to 49±13% of the levels in control animals, as determined by the branched-DNA assay. Serum ApoB protein concentration in mouse sera was lowered to 66±20% of carrier control levels. Serum cholesterol concentration in mouse sera was essentially unchanged at 94±10% of carrier control levels. Approx. 50-150 ng/ of AL-DUP 5163 per g tissue was detected in liver and jejunum tissue samples by the S1-nuclease protection assay.

AL-DUP 5385 was found to leave the levels of ApoB mRNA present in samples of liver tissue from treated mice essentially unchanged at 84±12% of the mRNA levels present in liver tissue of animals receiving carrier only, and levels of ApoB mRNA in jejunum came to 115±25% of the levels in control animals, as determined by the branched-DNA assay. Serum ApoB protein concentration in mouse sera was found unchanged at 101±24% of carrier control levels. Serum cholesterol concentration in mouse sera was essentially unchanged at 97±10% of carrier control levels. AL-DUP 5385 remained undetectable in liver and jejunum tissue samples in the S1-nuclease protection assay (FIG. 6A).

AL-DUP 5311 was found to leave the levels of ApoB mRNA present in samples of liver tissue from treated mice essentially unchanged at 96±16% of the mRNA levels present in liver tissue of animals receiving carrier only, and levels of ApoB mRNA in jejunum came to 96±28% of the levels in control animals, as determined by the branched-DNA assay. Serum ApoB protein concentration in mouse sera was found unchanged at 102±32% of carrier control levels. Serum cholesterol concentration in mouse sera was essentially unchanged at 104±10% of carrier control levels. Approx. 50-200 ng/ of AL-DUP 5311 per g tissue was detected in liver and jejunum tissue samples by the S1-nuclease protection assay (FIG. 6A).

AL-DUP 5386 was found to leave the levels of ApoB mRNA present in samples of liver tissue from treated mice essentially unchanged at 89±11% of the mRNA levels present in liver tissue of animals receiving carrier only, and levels of ApoB mRNA in jejunum came to 85±14% of the levels in control animals, as determined by the branched-DNA assay. Serum ApoB protein concentration in mouse sera was found unchanged at 94±31% of carrier control levels. Serum cholesterol concentration in mouse sera was essentially unchanged at 104±10% of carrier control levels. Approx. 50-200 ng/ of AL-DUP 5386 per g tissue was detected in liver and jejunum tissue samples by the S1-nuclease protection assay (FIG. 6A).

H.): Six groups of 6 animals, age 2.5 months, received a single intravenous bolus dose of 100, 50, 25 or 12.5 mg/kg body weight of AL-DUP 5167, or an equivalent amount of carrier. Animals were sacrificed 72 h post-dosing. Total serum cholesterol, serum ApoB 100 concentration, and liver and jejunum ApoB mRNA levels were determined.

The nucleotide sequence of AL-DUP 5167 is given above in Table 10.

This experiment was undertaken to assess the dose response for AL-DUP 5167.

At a dose of 100 mg/kg body weight, AL-DUP 5167 was found to lower the levels of ApoB mRNA present in samples of liver tissue from treated mice to 48±13% of the mRNA levels present in liver tissue of animals receiving carrier only, and levels of ApoB mRNA in jejunum were lowered to 37±3% of the levels in control animals, as determined by the branched-DNA assay. Serum ApoB protein concentration in mouse sera was lowered to 57±14% of carrier control levels. Serum cholesterol was lowered to 71±14% of carrier control levels.

At a dose of 50 mg/kg body weight, AL-DUP 5167 was found to lower the levels of ApoB mRNA present in samples of liver tissue from treated mice to 79±15% of the mRNA levels present in liver tissue of animals receiving carrier only, and levels of ApoB mRNA in jejunum were lowered to 67±15% of the levels in control animals, as determined by the branched-DNA assay. Serum ApoB protein concentration in mouse sera was lowered to 69±17% of carrier control levels. Serum cholesterol was found essentially unchanged at 90±28% of carrier control levels.

At a dose of 25 mg/kg body weight, AL-DUP 5167 was found to leave the levels of ApoB mRNA present in samples of liver tissue from treated mice essentially unchanged at 96±7% of the mRNA levels present in liver tissue of animals receiving carrier only, and levels of ApoB mRNA in jejunum were lowered to 56±11% of the levels in control animals, as determined by the branched-DNA assay. Serum ApoB protein concentration in mouse sera were determined to 68±26% of carrier control levels. Serum cholesterol was found essentially unchanged at 93±8% of carrier control levels.

At a dose of 12.5 mg/kg body weight, AL-DUP 5167 was found to leave the levels of ApoB mRNA present in samples of liver tissue from treated mice essentially unchanged at 90±14% of the mRNA levels present in liver tissue of animals receiving carrier only, and levels of ApoB mRNA in jejunum were unchanged at 77±22% of the levels in control animals, as determined by the branched-DNA assay. Serum ApoB protein concentration in mouse sera were determined to 95±5% of carrier control levels. Serum cholesterol was found essentially unchanged at 91±14% of carrier control levels.

I): 8 groups of 6 animals, age 2.5 months, received a single intravenous bolus dose of 100 mg/kg body weight of AL-DUP 5167 (for sequence, see Table 10), or an equivalent amount of carrier. Groups of animals treated with AL-DUP 5167 were sacrificed 18 h, 66 h, 96 h, 168 h, and 336 h post-dosing; groups of animals treated with carrier were sacrificed 18 h, 66 h, and 240 h post-dosing. The group sacrificed after 240 h was used as the control, all values are expressed as percent of the average found in this group. Total serum cholesterol, serum ApoB 100 concentration, and liver and jejunum ApoB mRNA levels were determined. An S1-nuclease protection assay was used to determine the amounts of AL-DUP-5167 present in liver tissues.

This experiment was designed to confirm the time course of the effects of AL-DUP 5167 on ApoB mRNA levels in liver and jejunum, and on serum ApoB and cholesterol concentrations, and to extend the time of observation.

18 h post-dosing, 3.3 µg/g tissue of AL-DUP 5167 were recovered in liver samples, which dropped to 22 ng/g tissue after 66 h, and below the limit of detection thereafter.

In animals sacrificed 18 hours post dosing of 100 mg/kg AL-DUP 5167 intravenously, 37±16% of the ApoB mRNA levels present in liver tissue of the 240 h carrier control group were found in the liver, and 87±29% of the ApoB mRNA levels present in jejunum tissue of the 240 h carrier control group were found in the jejunum. Serum ApoB protein concentration in mouse sera was lowered to XX±X % of carrier control levels.

In animals sacrificed 66 hours post dosing of 100 mg/kg AL-DUP 5167 intravenously, 47±7% of the ApoB mRNA levels present in liver tissue of the 240 h carrier control group were found in the liver, and 43±8% of the ApoB mRNA levels present in jejunum tissue of the 240 h carrier control group were found in the jejunum. Serum ApoB protein concentration in mouse sera was lowered to XX±X % of carrier control levels.

In animals sacrificed 96 hours post dosing of 100 mg/kg AL-DUP 5167 intravenously, 38±9% of the ApoB mRNA levels present in liver tissue of the 240 h carrier control group were found in the liver, and 78±14% of the ApoB mRNA levels present in jejunum tissue of the 240 h carrier control group were found in the jejunum. Serum ApoB protein concentration in mouse sera was lowered to XX±X % of carrier control levels.

In animals sacrificed 168 hours post dosing of 100 mg/kg AL-DUP 5167 intravenously, 57±5% of the ApoB mRNA levels present in liver tissue of the 240 h carrier control group were found in the liver, and 87±27% of the ApoB mRNA levels present in jejunum tissue of the 240 h carrier control group were found in the jejunum. Serum ApoB protein concentration in mouse sera was lowered to XX±X % of carrier control levels.

In animals sacrificed 336 hours post dosing of 100 mg/kg AL-DUP 5167 intravenously, 94±10% of the ApoB mRNA levels present in liver tissue of the 240 h carrier control group were found in the liver, and 109±12% of the ApoB mRNA levels present in jejunum tissue of the 240 h carrier control group were found in the jejunum. Serum ApoB protein concentration in mouse sera was lowered to XX±X % of carrier control levels.

In animals sacrificed 18 hours post dosing of saline control AL-DUP 5167 intravenously, 83±21% of the ApoB mRNA levels present in liver tissue of the 240 h carrier control group were found in the liver, and 109±26% of the ApoB mRNA levels present in jejunum tissue of the 240 h carrier control group were found in the jejunum. Serum ApoB protein concentration in mouse sera was lowered to 51±8% of carrier control levels.

In animals sacrificed 18 hours post dosing of 100 mg/kg AL-DUP 5167 intravenously, 104±19% of the ApoB mRNA levels present in liver tissue of the 240 h carrier control group were found in the liver, and 97±21% of the ApoB mRNA levels present in jejunum tissue of the 240 h carrier control group were found in the jejunum. Serum ApoB protein concentration in mouse sera was lowered to 51±8% of carrier control levels.

This experiment shows that the action of a cholesterol-conjugated siRNA may persist for 7 days or more in the liver, and 3 days or more in the gut. The latter is consistent with the average lifespan of the intestinal enterocyte.

Conclusions from experiments A)-I): An important consideration for siRNA based inhibition to gene expression is whether the observed effects are specific and not due to "off target" effects and potential interferon responses that have been reported with siRNAs in vitro and other oligonucleotide-based approaches. In our experiments, the effects of ApoB-specific, cholesterol-conjugated siRNAs were seen with several independent siRNAs targeting separate sequence regions of the ApoB mRNA. Further, the in vivo silencing of ApoB was specific as neither an unspecific siRNA nor a mismatch control siRNA mediated a significant reduction in ApoB mRNA, plasma ApoB protein levels, or total cholesterol. Cholesterol-conjugated ApoB-specific siRNAs, but not unconjugated ApoB-specific siRNAs, showed biological activity, demonstrating an important role for cholesterol conjugation to achieve systemic in vivo activity and suggesting the opportunity to further optimize activity based on systemic administration through chemical conjugation strategies.

Example 8

Cholesterol Stabilizes siRNA Activity

In exploring the potential for synthetic siRNAs to silence endogenous target genes in vivo, we have found that chemically-stabilized and cholesterol-conjugated siRNAs have markedly improved pharmacologic properties in vitro and in vivo. Chemically stabilized siRNAs with partial phosphorothioate backbone and 2'-O-methyl modifications on the sense and antisense strands showed significantly enhanced resistance towards degradation by exo- and endonucleases in serum and tissue homogenates. The conjugation of cholesterol at the 3'-end of the sense strand of a siRNA via a pyrrolidine linker (thereby generating cholesterol-conjugated siRNA) did not result in a significant loss of gene silencing activity in cell culture. In HeLa cells transiently expressing luciferase from a transfected plasmid and in the absence of transfection reagent or electroporation only a cholesterol-conjugated siRNA inhibited luciferase expression ($IC_{50}$ 200 nM) whereas unconjugated siRNA was inactive. Binding of cholesterol-conjugated siRNAs to human serum albumin (HSA) was determined by surface plasmon resonance measurement; unconjugated siRNAs demonstrated no measurable binding to HSA, while cholesterol-conjugated siRNAs were found to bind to HSA with an estimated $K_D$=1 µM. Due to enhanced binding to serum proteins, cholesterol-conjugated siRNAs administered to rats by IV injection showed improved in vivo pharmacokinetic properties as compared to unconjugated siRNAs. Following IV injection in rats at 50 mg/kg, radioactively-labeled cholesterol-conjugated siRNAs had a $t_{1/2}$=95+/−13 min in plasma whereas unconjugated siRNAs had a plasma $t_{1/2}$=6.2+/−0.6 min, as determined by curve fitting simulation assuming a two compartment model, first order elimination rate, using WinNonLin 4.1 (Pharsight Corporation, Mountain View, Calif., USA). As measured by RNase protection assay, cholesterol-conjugated siRNAs showed broad tissue biodistribution 24 h after a single 50 mg/kg IV bolus injection in mice. Whereas no detectable amounts of unconjugated siRNAs were observed in tissue samples, significant levels of cholesterol-conjugated siRNAs of about 200 ng/g tissue were detected in liver, heart, kidney, and lung samples. Together, these studies demonstrated that cholesterol conjugation significantly improves in vivo pharmacokinetic properties of siRNAs.

Example 9

ApoB Expression in Human ApoB-100 Transgenic Mice is Reduced by siRNAs Specific for Human and Mouse ApoB The experimental procedures were approved by the Alnylam Institutional Animal Care and Use Committee, and were performed in accordance with city of Cambridge, Mass. regulations regarding animal welfare.

Hemizygous male Human ApoB-100 transgenic mice (strain designation: B6.SSJL-Tg(APOB100)N20) were obtained from Taconic (Taconic, Germantown, N.Y., USA, cat. no. 1004-T) and were housed at constant temperature and humidity on a 12 hr light/dark cycle (6:30 AM/6:30 PM). Animals were fed irradiated standard rodent chow (PicoLab® Rodent Diet 20, Purina Mills, LLC, St. Louis, Mo., USA, cat. no. 5053).

Animals at 30-32 weeks of age were divided into three groups of eight for treatment. One group received three daily tail vein injections (24 hours between doses) of phosphate buffered saline (10 µl per gram body weight). A second group received three daily tail vein injections (24 hours between injections) of 50 mg siRNA AL-DUP 5167 per kilogram body weight in a dosing volume of 10 µl per gram body weight. The third group received three daily tail vein injections (24 hours between injections) of 50 mg siRNA AL-DUP 5311 per kilogram body weight in a dosing volume of 10 µl per gram body weight. The siRNA duplexes were formulated in phosphate buffered saline.

Twenty-four hours after the final injection, animals were sacrificed by $CO_2$ asphyxiation. Whole liver as well as the segment of the small intestine corresponding to the jejunum was harvested from each animal and rapidly frozen in liquid nitrogen. Frozen tissues were ground to a fine powder using a mortar and pestle.

Approximately 10 mg of each tissue powder was added to an ice-cold 1.5 ml Eppendorf tube, and 1 ml Tissue and Cell Lysis Solution (Epicentre, Madison, Wis., USA, cat. No. MTC096H) containing 3.3 µl (10 µl per 3 ml) of a 50 µg/µl stock solution of Proteinase K (Epicentre, Madison, Wis., USA, cat. No. MPRK092) were added. The tubes were vortexed and incubated at 65° C. for 15 minutes; vortexing every 5 minutes. Cellular debris was pelleted at 5000 rcf for 10 minutes at RT, and 800 µl supernatant were transferred to a fresh tube. Lysates were used immediately in the branched DNA assay (described above) to determine relative levels of ApoB and GAPDH mRNA, or stored at −80° C. for later use.

The ApoB specific siRNA AL-DUP 5167 was found to reduce mouse ApoB mRNA levels (significantly different at p<0.01); 43±10% in liver and 58±12% in jejunum of mouse ApoB mRNA levels in carrier treated animals were found in animals treated with AL-DUP 5167. Human ApoB mRNA in liver was reduced to 40±10% of levels in livers of control animals. The mismatch control siRNA AL-DUP 5311 was found to leave ApoB mRNA levels essentially unchanged; 93±20% in liver and 104±13% in jejunum of mouse ApoB mRNA levels in carrier treated animals were found in animals treated with AL-DUP 5167. Human ApoB mRNA in liver was determined to 92±24% of levels in livers of control animals.

Example 10

Specific ApoB Cleavage Sites can be Identified by 5'-RACE PCR

Primers were purchased from Operon Biotechnologies, Inc. (Alameda, Calif., USA).

The specific siRNA-induced cleavage products of ApoB mRNA in pooled liver and jejunum from each of the treatment groups of experiment (G.) above (Example 7) were identified by 5'-RACE as described in Llave, et al. *Science* 2002, 297: 2053-6, and Yekta, et al. *Science* 2004, 304:594-6, with the following modifications and primers given below. In such experiment, an adaptor is reacted with 5'-phosphate-bearing RNA present in an RNA sample, such as the 3'-products of the cleavage of mRNA by siRNA-complexed RISC. The products of most, if not all, nucleolytic reactions catalyzed by nucleases do not contain a 5'-phosphate group and therefore will not react with the adaptor. In the subsequent PCR reactions, only those molecular species comprising both the adaptor sequences as well as the target gene sequence are amplified by appropriate selection of primers.

Following ligation of the RACE adapter ("GeneRacer" adapter, Invitrogen), cDNA synthesis was primed using a gene specific primer, 5167GSP, to yield "5167" cDNA. Sequences corresponding to ApoB were amplified in sequential PCR reactions using the following primer pairs:

PCR reaction 1: GR5'-XbaI(forward)+5167 ApoB Rev2-SalI (reverse)

PCR reaction 2: GS5'Nest F-XbaI(forward)+5167 ApoB Rev3-SalI(reverse)

Figure 7A:
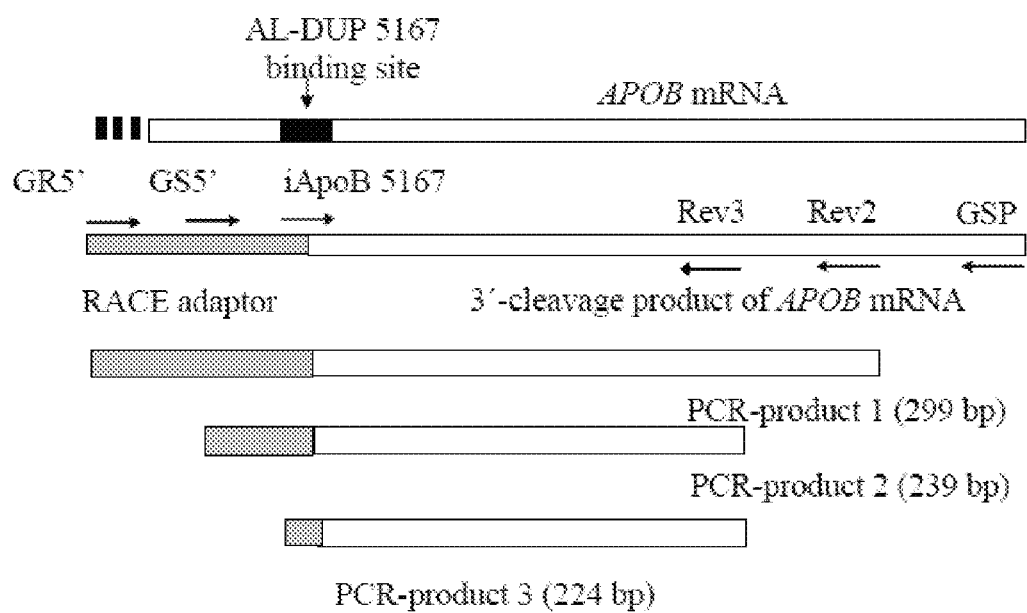
FIG. 7A is a schematic representation of the ApoB mRNA and of the adapter ligated ApoB cDNA used for 5'-RACE PCR. The schematic shows the relative target sites of the AL-DUP 5167 siRNA and the PCR primers, and the size of PCR reaction products.
Figure 7B:
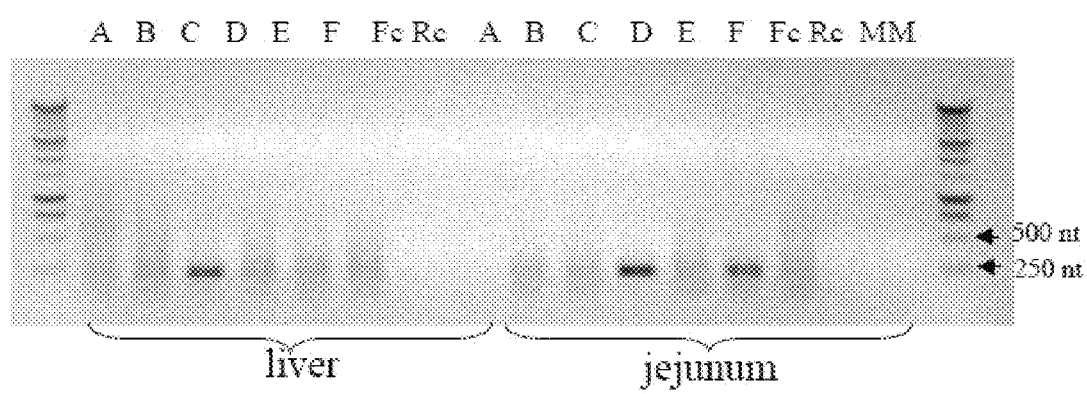
FIG. 7B is an agarose gel of RACE-PCR amplification 3. The electrophoretic analysis indicates specific cleavage products in liver and jejunum of mice treated with ApoB specific AL-DUP 5167 only. The lanes of the gel are marked by capital letters that indicate treatment groups and controls. The lanes are marked as follows: A: PBS; B: AL-DUP 5386; C: AL-DUP 5167; D: AL-DUP 5163, E: AL DUP 5385; F: AL-DUP 5311; Fc: Control, Forward primer only using cDNA from group C; RC: Control, Reverse primer only using cDNA from group C.

A fifty-fold dilution of PCR reaction 1 was used in PCR reaction 2. Products of each PCR reaction were analyzed by agarose gel electrophoresis, and visualized by ethidium bromide staining. Specific bands of the expected size corresponding to siRNA-directed cleavage were seen in liver from animals receiving AL-DUP 5167 and in jejunum from animals receiving AL-DUP 5167 and, to a lesser extent, AL-DUP 5385 (see FIG. 7).

The specific bands from PCR reaction 1 were excised and sequenced (sequencing primer: 5167 ApoB Rev3-SalI) to confirm the presence of the junction between the RACE adapter and nucleotide 10226 of mouse ApoB (Accession number: XM137955).

To specifically amplify fragments corresponding to the predicted siRNA cleavage site, PCR reaction 1 was diluted fifty fold and amplified with the following primer pairs:

PCR reaction 3: iApoB 5167-XbaI(forward)+5167 ApoB Rev3-SalI (reverse)

A PCR product is formed in PCR reaction 3 if and only if a reaction product is present in PCR reaction 1 combining the RACE adaptor with the RISC cleavage product of ApoB mRNA predicted by RNA interference mediated by AL-DUP 5167. Products of this PCR reaction were visualized as described above (FIG. 7). Confirmatory sequencing of the amplified bands was performed as above.

Primer sequences:

GR5'-XbaI

SEQ. ID NO. 279
5'-CTCTAGAGCGACTGGAGCACGAGGACACTGA-3'

GS5'Nest F-XbaI

SEQ. ID NO. 280
5'-CTCTAGAGGGACACTGACATGGACTGAAGGAGTA-3'

5167 GSP

SEQ. ID NO. 281
5'-CTCCTGTTGCAGTAGAGTGCAGCT-3'

5167 ApoB Rev2- Sal I

SEQ. ID NO. 282
5'-ACGCGTCGACGTGGGAGCATGGAGGTTGGCAGTTGTTC-3'

5167 ApoB Rev3-Sal I

SEQ. ID NO. 283
5'-ACGCGTCGACGTAATGGTGCTGTCATGACTGCCCTT-3' iApoB 5167- Xba I

SEQ. ID NO. 284
5'-CTCTAGAGCATGGACTGAAGGAGTAGAAAGAA-3'

Example 11

Further Testing of Modified siRNAs

Design of further modified siRNAs

Further siRNAs representing modified versions of AL-DUP 5002, AL-DUP 5035, AL-DUP 5048, AL-DUP 5089, AL-DUP 5097, and AL-DUP 5098 were tested for stability and activity towards inhibiting the expression of ApoB. A modified version of AL-DUP 5048 was synthesized bearing a cholesteryl moiety linked to the 3'-end of the sense strand via a pyrrolidine linker. For each of the unmodified iRNA agents AL-DUP 5002, AL-DUP 5035, AL-DUP 5089, AL-DUP 5097, and AL-DUP 5098, one iRNA agent was synthesized with a 21-nucleotide sense strand, a 23-nucleotide antisense strand forming a 2-nucleotide 3'-overhang, bearing a cholesteryl moiety on the 3'-end of the sense strand linked via a phosphorothioate-comprising linker, 2'-O-methyl nucleotides in positions 21 and 22 of the antisense strand, and phosphorothioate linkages between positions 21 and 22, and 22 and 23, of the antisense strand. This configuration corresponds to the pattern of modifications already used in AL-DUP 5167, and is meant to protect the iRNA agent from the degrading activity of exonucleases.

In addition, a second iRNA agent was synthesized representing a modified version of AL-DUP 5002, AL-DUP 5035, AL-DUP 5089, AL-DUP 5097, and AL-DUP 5098, bearing a cholesteryl moiety on the 3'-end of the sense strand linked via a phosphorothioate-comprising linker, 2'-O-methyl modified nucleotides in the positions of the 5'-most pyrimidines in all occurrences of the sequence motifs 5'-UA-3', 5'-CA-3', 5'-UU-3', and 5'-UG-3', and phosphorothioate linkages between positions 21 and 22, and 22 and 23, of the antisense strand. These additional modifications were made to protect these siRNAs from the degrading activity of endonucleases. The corresponding sequences are listed in Table 11.

TABLE 11

Modified iRNA agents for stability and activity assays

| Duplex descriptor | SEQ. ID No. | Sense strand sequence | SEQ. ID No. | Antisense strand sequence |
|---|---|---|---|---|
| AL-DUB 5546 | 285 | gucaucacacugaauaccaau(chol) | 286 | cagggguugaagccauacaccumcmu |
| AL-DUB 5536 | 287 | gaumumgaumumgaccumguccmaumuc(chol) | 288 | gaaumggacmaggucaaucmaaucmumu |
| AL-DUB 5537 | 289 | gauugauugaccuguccauuc(chol) | 290 | gaauggacaggucaaucaaucmumu |
| AL-DUB 5538 | 291 | cmaccmaacumucumuccmacgaguc(chol) | 292 | gacucgumggaagaagumumggumgmumu |
| AL-DUB 5539 | 293 | caccaacuucuuccacgaguc(chol) | 294 | gacucguggaagaaguuggugmumu |
| AL-DUB 5540 | 295 | gagumumumgumgacmaaaumaumgggc(chol) | 296 | gcccmaumaumumumgucmacmaaacucmcma |
| AL-DUB 5541 | 297 | gaguuugugacaaauaugggc(chol) | 264 | gcccauauuugucacaaacucmcma |
| AL-DUB 5542 | 262 | cumumumacmaagccumumggumucmagu(chol) | 263 | acumgaaccmaaggcumumgumaaagmumq |
| AL-DUB 5543 | 260 | cuuuacaagccuugguucagu(chol) | 259 | acugaaccaaggcuuguaaagmumq |
| AL-DUB 5544 | 258 | ggaaucumumaumaumumumgauccmaa(chol) | 257 | umumggaucmaaaumaumaagaumuccmcmu |
| AL-DUB 5545 | 252 | ggaaucuuauauuugauccaa(chol) | 251 | uuggaucaaauauaagauuccmcmu | m = 2'O-methyl modification; "(chol)" indicates cholesterol conjugated to the 3'-end via a pyrrolidine linker comprising a phosphorothioate; "(chol)" indicates cholesterol conjugated to the 3'-end via a pyrrolidine linker lacking a phosphorothioate siRNA Stability Testing The siRNAs, the sequences of which are shown in Table 11, were tested for stability by incubation in human serum (Sigma-Aldrich Chemie GmbH, Taufkirchen, Germany, cat. No. H1513) followed by isolation of separation of fragments by HPLC. A 50 µM solution of the respective siRNA in phosphate buffered saline (PBS, Sigma-Aldrich Chemie GmbH, Taufkirchen, Germany) was incubated with serum at a ratio of 10:1 serum:siRNA solution for 30 min, 1, 2, 4, 8, 16 and 24 hours, and samples were analysed as described below.

Determination of siRNA Degradation Time Course by HPLC Following Proteinase K Treatment of Serum Samples Proteinase K (20 mg/ml) was obtained from peQLab (Erlangen, Germany; Cat.-No. 04-1075) and diluted 1:1 with deionized water (18.2 mΩ) to a final concentration of 10 mg/ml Proteinase K. Proteinase K Buffer (4.0 ml TRIS-HCl 1M pH 7.5, 1.0 ml EDTA 0.5M, 1.2 ml NaCl 5M, 4.0 ml SDS 10%) was prepared fresh and kept at 50° C. until use to avoid precipitation.

A 40 mer of poly(L-dT), (L-dT)$_{40}$ was obtained from Noxxon Pharma AG (Berlin, Germany) and used as an internal standard. Polymers of the L-enantiomers of nucleic acids show an extraordinary stability towards nucleolytic degradation (Klussman S, et al., Nature Biotechn. 1996, 14:1112) but otherwise very similar properties when compared to naturally occurring nucleic acids consisting of R-enantiomers.

To terminate the siRNA-degradation, 25 µl of Proteinase K buffer were added to serum incubation samples immediately after expiry of the respective incubation period, the mixture vortexed at highest speed for 5 s (Vortex Genie 2, Scientific Industries, Inc., Bohemia, N.Y., USA, cat. no. SI 0256), 8 µl Proteinase K (10 mg/ml) were added followed by vortexing for 5 s, and finally the mixture was incubated for 20 min in a thermomixer at 42° C. and 1050 rpm.

5 µl of a 50 µM solution (250 pmole) of (L-dT)$_{40}$ were added as an internal standard to each well, the solution was vortexed for 5 s, and the tube centrifuged for 1 min in a tabletop centrifuge to collect all droplets clinging to the inner surfaces of the wells at the bottom. The solution was transferred to a 96 well Captiva 0.2 um filter plate (Varian, Germany, Cat. No. A5960002) and filtered by centrifugation at 21900 rcf for 45 min.

The incubation wells were washed with 47.5 µl deionized water (18.2 mΩ), the wash filtered through the Captiva Filter Unit at 21900 rcf for 15 min, and the wash step repeated. Approximately 180 µl of the theoretical total volume of 200 µl are on average recovered after the second washing step.

Ion exchange chromatographic separation of siRNA single strands from each other and from degradation products:

A Dionex BioLC HPLC-system equipped with inline-degasser, autosampler, column oven and fixed wavelength UV-detector (Dionex GmbH, Idstein, Germany) was used under denaturing conditions. Standard run parameters were:

| | |
|---|---|
| Column: | Dionex DNA-Pac100; 4 × 250 mm |
| Temperature: | 75° C. |
| Eluent A: | 10 mM NaClO$_4$, 20 mM TRIS-HCl, 1 mM EDTA; 10% acetonitrile, pH = 8.0 |
| Eluent B: | 800 mM NaClO$_4$, 20 mM TRIS-HCl, 1 mM EDTA; 10% acetonitrile, pH = 8.0 |
| Detection: | @ 260 nm |
| Gradient: | 0-1 min: 10% B |
| | 1-11 min: 10% -> 35% B |
| | 11-12 min: 35% B -> 100% B |
| | 12-14 min: 100% B->10% B |
| | 14-16 min: 10% B for column reequilibration |
| Injection volume: | 20 µl |

Where separation between the two strands of an siRNA was not satisfactory or a degradation fragment co-eluted with one strand, the chromatographic parameters were adjusted by changing temperature, pH, replacement of NaClO$_4$ by NaBr, the concentration of acetonitrile, and/or adjusting the slope of the eluent gradient until separation was achieved which allowed separate quantitation of the peaks from sense and antisense strand.

Peak areas for full length strands were obtained by integration of the UV detector signal using software supplied by the manufacturer of the instrument (Chromeleon 6.6; Dionex GmbH, Idstein, Germany).

Data Analysis:

Integrated sense strand, antisense strand, and internal standard peak areas were obtained for all samples and the normalization control.

A correction factor CF, accounting for liquid losses in the filtration and washing steps, was determined for every sample by calculating the ratio of experimental to theoretical internal standard peak area. The theoretical internal standard peak area is obtained, e.g. from a calibration curve of the internal standard obtained by injecting 50 µl each of a serial dilution of the 50 µM solution of (L-dT)$_{40}$ onto the HPLC column, and calculation of the theoretical peak area corresponding to 25 pmole (L-dT)$_{40}$ with the equation obtained by linear least square fit to the peak areas from the dilution series. The correction factor CF to be applied to the peak areas of the sense and antisense strand is the obtained as:

$$CF = PeakArea_{intStd}(theoretical)/PeakArea_{intStd}(Sample)$$

This treatment assumes that, by virtue of washing the filter twice, virtually complete recovery is achieved in the combined filtrates, and corrects for the variable volume of wash water retained in the filter, such that peak areas from different samples can be compared.

The peak areas obtained for the sense and antisense strand peaks for each time point are then multiplied with the correction factor CF to obtain Normalized Peak Areas (NPA$_{sense,t}$, NPA$_{antisense,t}$):

$$NPA_{sense\ or\ antisense,t} = (PeakArea_{sense\ or\ antisense,t}) \times CF$$

To obtain the relative amount of remaining Full Length Product (% FLP) for the sense and antisense strands at time t, the Normalized Peak Area for each strand at time t=0 min (NPA$_{sense,t=0}$, NPA$_{antisense,t=0}$) is set as 100%, and the NPAs from other time points are divided by these values.

$$\% FLP_{t=1,2,3...n} = (NPA_{t=1,2,3...n}/NPA_{t=0})*100$$

The value obtained from the control sample, where the siRNA was incubated with annealing buffer only, may serve as a control of the accuracy of the method. The % FLP for both strands should lie near 100%, within error margins, regardless of time of incubation.

The degradation half life $t_{1/2}$ may then be calculated for each strand, assuming first order kinetics, from the slope of a linear least square fit to a plot of ln(% FLP) versus time as:

$$t_{1/2} = ln(0,5)/slope$$

Serum Half Lifes of siRNAs Described by the Sequences in Table 11

The degradation half lifes of the full length products of the siRNAs described by the sequences shown in Table 11 are given in Table 12. As is evident from the difference in the half life of the antisense strand of AL-DUP 5546 compared to the half life of its sense strand or the antisense strand of AL-DUP 5167, protecting the 3'-end of a strand by means of 2'-O-methyl groups and phosphorothioate linkages in the 3'-penultimate nucleotides affords an increase of approximately 6- to 7-fold in terms of the degradation half life. Further substituting 2'-O-methyl modified nucleotides at sites particularly prone to endonucleolytic degradation further improved half lifes by approximately 3- to 4-fold, except for AL-DUP 5543, where the average-fold improvement was 20.

TABLE 12

Serum half lifes of siRNAs with different stabilizing modifications

| Duplex descriptor | $t_{1/2}$ (sense strand) [h] | $t_{1/2}$ (antisense strand) [h] | average-fold improvement[1] |
|---|---|---|---|
| AL-DUP 5167 | 8.7 | 6.5 | 4 |
| AL-DUP 5546 | 6.8 | 0.9 | |
| AL-DUP 5536 | 22.7 | 16.6 | 3 |
| AL-DUP 5537 | 7.4 | 7.7 | |
| AL-DUP 5538 | 21.1 | 18.4 | 4 |
| AL-DUP 5539 | 6.3 | 3.7 | |
| AL-DUP 5540 | 27.3 | 24.7 | 3 |
| AL-DUP 5541 | 8.2 | 9.0 | |
| AL-DUP 5542 | 40.3 | 15.9 | 20 |
| AL-DUP 5543 | 1.5 | 1.2 | |
| AL-DUP 5544 | 17.5 | 14.9 | 3 |
| AL-DUP 5545 | 5.7 | 6.8 | |

[1] [(($t_{1/2}$(modified sense strand)/$t_{1/2}$(unmodified sense strand)) + ($t_{1/2}$(modified antisense strand)/$t_{1/2}$(unmodified antisense strand)))/2]

In Vitro Activity of siRNAs Modified to Resist Endonucleolytic Degradation

In vitro activity of the siRNAs of Table 11 was tested as described in Example 3 hereinabove. Results are shown in Table 13.

TABLE 13

In vitro activity of siRNAs modified to resist endonucleolytic degradation compared to

| Duplex descriptor | IC$_{50}$ modified [nM] | Duplex descriptor | IC$_{50}$ unmodified [nM] |
|---|---|---|---|
| AL-DUP 5167 | 0.4 | AL-DUP 5546 | 0.5 |
| AL-DUP 5536 | 0.6 | AL-DUP 5537 | 0.6 |
| AL-DUP 5538 | 21 | AL-DUP 5539 | 1 |
| AL-DUP 5540 | 7 | AL-DUP 5541 | 7 |
| AL-DUP 5542 | 3 | AL-DUP 5543 | 6 |
| AL-DUP 5544 | 7 | AL-DUP 5545 | 4 |

As is evident from the comparison of the IC$_{50}$ for AL-DUP 5167 and AL-DUP 5546 in Table 13, the introduction of phosphorothioate linkages between positions 21 and 22, and 22 and 23, and 2'-O-methyl groups in positions 21 and 22, of the antisense strand, in AL-DUP 5167 did not adversely affect the activity of this siRNA. Furthermore, as can be seen from a comparison of the IC$_{50}$ for AL DUP 5536 vs. AL-DUP 5537, AL DUP 5538 vs. AL DUP 5539. AL DUP 5540 vs. AL-DUP 5541, AL DUP 5542 vs. AL-DUP 5543, and AL DUP 5544 vs. AL DUP 5545, the introduction of 2'-O-methyl modified nucleotides in the positions of the 5'-most pyrimidines in all occurrences of the sequence motifs 5'-UA-3',5'-CA-3',5'-UU-3', and 5'-UG-3' in most cases had no adverse impact on the activity of these molecules either.

In Vivo Activity of siRNAs Modified to Resist Endonucleolytic Degradation

The following experiment was performed using routines and procedures as described in Example 7 above.

13 groups of 5 animals, age 2.5 months, received a single intravenous bolus dose of 100 mg/kg body weight of AL-DUP 5167, AL DUP 5536, AL-DUP 5537, AL DUP 5538, AL DUP 5539, AL DUP 5540, AL-DUP 5541, AL DUP 5542, AL-DUP 5543, AL DUP 5544, AL DUP 5545, or an equivalent amount of carrier. Animals were sacrificed 72 h post-dosing. Total serum cholesterol, serum ApoB 100 concentration, and liver and jejunum ApoB mRNA levels were determined. In addition, the concentration of the siRNA was determined in liver, jejunum, and serum samples from 3 animals from each group by the S1-nuclease protection assay as described in Example 7; however, quantitation of radioactive band intensity was performed by visual comparison of bands to the dilution series, and standard deviations were not calculated.

The nucleotide sequence of AL-DUP 5167 is given above in Table 10. The nucleotide sequences of AL DUP 5536, AL-DUP 5537, AL DUP 5538, AL DUP 5539, AL DUP 5540, AL-DUP 5541, AL DUP 5542, AL-DUP 5543, AL DUP 5544, and AL DUP 5545 are given above in Table 11.

This experiment was undertaken to assess the impact of modifications introduced into siRNAs to improve their stability in biological media on their gene expression inhibiting activity in vivo.

At a dose of 100 mg/kg body weight, AL-DUP 5167 was found to lower the levels of ApoB mRNA present in samples of liver tissue from treated mice to 42±12% of the mRNA levels present in liver tissue of animals receiving carrier only, and levels of ApoB mRNA in jejunum were lowered to 45±8% of the levels in control animals, as determined by the branched-DNA assay. Serum ApoB protein concentration in mouse sera was lowered to 44±23% of carrier control levels. Serum cholesterol was left essentially unchanged at 75±20% of carrier control levels. Average iRNA concentrations for 3 animals were found as approximately: liver, 70 ng/g, jejunum 14 ng/g, serum 14 ng/g.

At a dose of 100 mg/kg body weight, AL-DUP 5546 was found to leave the levels of ApoB mRNA present in samples of liver tissue from treated mice essentially unchanged at 95±9% of the mRNA levels present in liver tissue of animals receiving carrier only, and levels of ApoB mRNA in jejunum were at 102±16% of the levels in control animals, as determined by the branched-DNA assay. Serum ApoB protein concentration in mouse sera was left essentially unchanged at 113±39% of carrier control levels. Serum cholesterol was elevated to 132±10% of carrier control levels. Average iRNA concentrations for 3 animals were found as approximately: liver, 1 ng/g; jejunum, not detectable; serum, not detectable.

At a dose of 100 mg/kg body weight, AL-DUP 5536 was found to lower the levels of ApoB mRNA present in samples of liver tissue from treated mice to 56±8% of the mRNA levels present in liver tissue of animals receiving carrier only, and levels of ApoB mRNA in jejunum were lowered to 28±8% of the levels in control animals, as determined by the branched-DNA assay. Serum ApoB protein concentration in mouse sera was lowered to 46±6% of carrier control levels. Serum cholesterol was lowered to 74±33% of carrier control levels. Average iRNA concentrations for 3 animals were found as approximately: liver, 2 ng/g; jejunum, 6 ng/g, serum, 6 ng/g.

At a dose of 100 mg/kg body weight, AL-DUP 5537 was found to lower the levels of ApoB mRNA present in samples of liver tissue from treated mice to 72±11% of the mRNA levels present in liver tissue of animals receiving carrier only, and levels of ApoB mRNA in jejunum were essentially unchanged at 94±9% of the levels in control animals, as determined by the branched-DNA assay. Serum ApoB protein concentration in mouse sera was left essentially unchanged at 75±25% of carrier control levels. Serum cholesterol was left essentially unchanged at 118±9% of carrier control levels. Average iRNA concentrations for 3 animals were found as approximately: liver, not detectable; jejunum, not detectable, serum, 1 ng/g.

At a dose of 100 mg/kg body weight, AL-DUP 5538 was found to lower the levels of ApoB mRNA present in samples of liver tissue from treated mice to 56±16% of the mRNA levels present in liver tissue of animals receiving carrier only, and levels of ApoB mRNA in jejunum were lowered to 75±1% of the levels in control animals, as determined by the branched-DNA assay. Serum ApoB protein concentration in mouse sera was left essentially unchanged at 102±27% of carrier control levels. Serum cholesterol left essentially unchanged at 117±18% of carrier control levels. Average iRNA concentrations for 3 animals were found as approximately: liver, 35 ng/g; jejunum, 7 ng/g, serum, 18 ng/g.

At a dose of 100 mg/kg body weight, AL-DUP 5539 was found to leave the levels of ApoB mRNA present in samples of liver tissue from treated mice essentially unchanged at 76±18% of the mRNA levels present in liver tissue of animals receiving carrier only, and levels of ApoB mRNA in jejunum were lowered to 62±12% of the levels in control animals, as determined by the branched-DNA assay. Serum ApoB protein concentration in mouse sera was left essentially unchanged at 108±23% of carrier control levels. Serum cholesterol was left essentially unchanged at 102±18% of carrier control levels. Average iRNA concentrations for 3 animals were found as approximately: liver, 7 ng/g; jejunum, 4 ng/g, serum, 2 ng/g.

At a dose of 100 mg/kg body weight, AL-DUP 5540 was found to lower the levels of ApoB mRNA present in samples of liver tissue from treated mice to 54±12% of the mRNA levels present in liver tissue of animals receiving carrier only, and levels of ApoB mRNA in jejunum were lowered to 54±12% of the levels in control animals, as determined by the branched-DNA assay. Serum ApoB protein concentration in mouse sera was left essentially unchanged at 72±30% of carrier control levels. Serum cholesterol was left essentially unchanged at 91±10% of carrier control levels. Average iRNA concentrations for 3 animals were found as approximately: liver, 130 ng/g; jejunum, 28 ng/g, serum, 25 ng/g.

At a dose of 100 mg/kg body weight, AL-DUP 5541 was found to lower the levels of ApoB mRNA present in samples of liver tissue from treated mice to 73±10% of the mRNA levels present in liver tissue of animals receiving carrier only, and levels of ApoB mRNA in jejunum were lowered to 68±5% of the levels in control animals, as determined by the branched-DNA assay. Serum ApoB protein concentration in mouse sera was left essentially unchanged at 90±8% of carrier control levels. Serum cholesterol was left essentially unchanged at 99±8% of carrier control levels. Average iRNA concentrations for 3 animals were found as approximately: liver, 72 ng/g; jejunum, 10 ng/g, serum, 7 ng/g.

At a dose of 100 mg/kg body weight, AL-DUP 5542 was found to lower the levels of ApoB mRNA present in samples of liver tissue from treated mice to 58±9% of the mRNA levels present in liver tissue of animals receiving carrier only, and levels of ApoB mRNA in jejunum were lowered to 28±4% of the levels in control animals, as determined by the branched-DNA assay. Serum ApoB protein concentration in mouse sera was lowered to 55±9% of carrier control levels. Serum cholesterol was left essentially unchanged at 61±27% of carrier control levels. Average iRNA concentrations for 3 animals were found as approximately: liver, 8 ng/g; jejunum, 17 ng/g, serum, 22 ng/g.

At a dose of 100 mg/kg body weight, AL-DUP 5543 was found to lower the levels of ApoB mRNA present in samples of liver tissue from treated mice to 77±5% of the mRNA levels present in liver tissue of animals receiving carrier only, and levels of ApoB mRNA in jejunum were essentially unchanged at 91±14% of the levels in control animals, as determined by the branched-DNA assay. Serum ApoB protein concentration in mouse sera was left essentially unchanged at 97±16% of carrier control levels. Serum cholesterol was left essentially unchanged at 128±24% of carrier control levels. Average iRNA concentrations for 3 animals were found as approximately: liver, not detectable; jejunum, not detectable, serum, not detectable.

At a dose of 100 mg/kg body weight, AL-DUP 5544 was found to lower the levels of ApoB mRNA present in samples of liver tissue from treated mice to 63±6% of the mRNA levels present in liver tissue of animals receiving carrier only, and levels of ApoB mRNA in jejunum were lowered to 20±3% of the levels in control animals, as determined by the branched-DNA assay. Serum ApoB protein concentration in mouse sera was lowered to 46±5% of carrier control levels. Serum cholesterol was lowered to 55±5% of carrier control levels. Average iRNA concentrations for 3 animals were found as approximately: liver, >900 ng/g; jejunum, 60 ng/g; serum, 40 ng/g.

At a dose of 100 mg/kg body weight, AL-DUP 5545 was found to lower the levels of ApoB mRNA present in samples of liver tissue from treated mice to 58±11% of the mRNA levels present in liver tissue of animals receiving carrier only, and levels of ApoB mRNA in jejunum were lowered to 37±11% of the levels in control animals, as determined by the branched-DNA assay. Serum ApoB protein concentration in mouse sera was lowered to 50±6% of carrier control levels. Serum cholesterol was left essentially unchanged at 75±28% of carrier control levels. Average iRNA concentrations for 3 animals were found as approximately: liver, 70 ng/g; jejunum, 7 ng/g; serum, not detectable.

Example 12

Testing siRNAs for Immunogenic Potential

Recently, several reports have been published that postulated a potential of siRNA agents to illicit a possibly adverse immunogenic response (see, for example, Hornung et al., Nature Med 2005, 11:263-270). Little is known about the biological consequences of, for example, a temporary interferon-α (IFN-α) increase in humans potentially caused by siRNA. To circumvent unnecessary, hazardous side effects, it is desirable to have a potent antiviral siRNA with little or no detectable immunostimulatory activity. Albeit a true simulation of the exact processes in humans are not possible, we consider the described experiment as appropriate for predicting immunostimulation by oligonucleotides and siRNA.

We tested the immunogenicity of the siRNAs listed in Table 11 by measuring the induction of IFN-α in peripheral blood mononuclear cells (PBMC) by siRNAs AL-DUP 5167, AL-DUP 5536, AL-DUP 5537, AL DUP 5538, AL DUP 5539, AL DUP 5542, AL-DUP 5543, AL DUP 5544, and AL DUP 5545, AL-DUP 5311 was included as an unrelated sequence control. ODN2216, a strong inducer of IFN-α (Hornung et al., Nature Med 2005, 11:263-270) was used as a positive control, PBS as negatice control. The nucleotide sequence of ODN2216 is

5'-G̲GGGGACGATCGTCG̲G̲G̲G̲G̲G̲-3'  SEQ. ID NO. 306

PBMC were isolated by Ficoll gradient centrifugation as described in Chang, H. S., and Sack, D. A., Clin. Diag. Lab. Immunology 2001, 8: 482-488, except that an unfiltered, erythrocyte depleted leukocyte concentrate (Buffy Coat) from single donors obtained from the Institute for Transfusion Medicine gGmbH, Suhl, Germany, diluted 1:1 with PBS, was employed as starting material, and that the final suspension in RPMI complete medium (RPMI1640 complete; 10% FCS; 1% L-Glu) was adjusted to $1 \times 10^6$ cells/ml.

Cells were incubated with ODN2216 or siRNAs in Opti-MEM or Opti-MEM plus the transfection reagent GenPorter 2 (GP2; Peqlab Biotechnologie GmbH, Erlangen, Germany). 100 μl cell suspension (100.000 cells) per well of a 96 well plate were combined with 50 μl of a 1.5 μM solution of oligonucleotide in Opti-MEM (final oligonucleotide conc. 500 nM), or 50 μl of a 1:1 mixture of a) a mixture of 6 μl of GP2 reagent with 119 μl Opti-MEM, and b) a mixture of 1 μl 100 μM solution of oligonucleotide in PBS and 124 μl Diluent B from the GP2 kit (final oligonucleotide conc. 133 nM). The incubation was kept at 37° C. for 24 h, and 50 μl supernatant were carefully removed from the top of the well. These were employed for IFN-α determination using the huIFN-α instant ELISA (BenderMed Systems, Vienna, Austria, catalogue no. BMS216INST). Table 14 summarizes the results.

TABLE 14

IFN-α production by peripheral blood mononuclear cells incubated with siRNAs or ODN2216

| Duplex descriptor | IFN-α [pg/ml supernatant] |
| --- | --- |
| Saline | 0 ± 3 |
| ODN 2216 | 383 ± 62 |
| AL-DUP 5311 | 77 ± 4 |
| AL-DUP 5167 | 193 ± 9 |
| AL-DUP 5546 | 159 ± 33 |
| AL-DUP 5536 | 0 ± 1 |
| AL-DUP 5537 | 2 ± 1 |
| AL-DUP 5538 | −5 ± 0 |
| AL-DUP 5539 | −10 ± 1 |
| AL-DUP 5542 | −3 ± 1 |
| AL-DUP 5543 | −2 ± 0 |
| AL-DUP 5544 | −2 ± 0 |
| AL-DUP 5545 | −10 ± 0 |

Conclusions from Examples 11 and 12:

a) Oligonucleotides with modified nucleotides in certain particularly degradation-prone sites benefit in terms of in vitro half life in biological media while their in vitro and in vivo gene expression inhibiting activity is largely unaffected b) Depending on their sequence, siRNAs can be, but are not generally, immunostimulatory agents.

c) AL-DUP 5536, AL-DUP 5540 and AL-DUP 5542 are particularly promising candidates as iRNA agents for the inhibition of apoB expression, and therefore as therapeutics for disorders involving aberrant expression of apoB.

Table 15 lists the agent numbers that may be used herein to designate the iRNA agents described above:

TABLE 15

IFN-α production by peripheral blood mononuclear cells incubated with siRNAs or ODN2216

| Duplex descriptor | Agent number |
| --- | --- |
| AL-DUP 5163 | 54 |
| AL-DUP 5164 | 55 |
| AL-DUP 5165 | 56 |
| AL-DUP 5166 | 57 |
| AL-DUP 5167 | 58 |
| AL-DUP 5168 | 59 |
| AL-DUP 5169 | 60 |
| AL-DUP 5170 | 61 |
| AL-DUP 5180 | 62 |

TABLE 15-continued

IFN-α production by peripheral blood mononuclear cells incubated with siRNAs or ODN2216

| Duplex descriptor | Agent number |
|---|---|
| AL-DUP 5181 | 63 |
| AL-DUP 5182 | 64 |
| AL-DUP 5183 | 65 |
| AL-DUP 5536 | 66 |
| AL-DUP 5537 | 67 |
| AL-DUP 5538 | 68 |
| AL-DUP 5539 | 69 |
| AL-DUP 5542 | 70 |
| AL-DUP 5543 | 71 |
| AL-DUP 5544 | 72 |
| AL-DUP 5545 | 73 |
| AL-DUP 5545 | 74 |

Other Embodiments

A number of embodiments of the invention have been described. Nevertheless, it will be understood that various modifications may be made without departing from the spirit and scope of the invention.

---

What is claimed is:

1. An iRNA agent comprising a sense strand and an antisense strand, wherein said sense strand comprises a first sequence and said antisense strand comprises a second sequence, wherein said first sequence is complementary to said second sequence, and wherein said second sequence comprises at least 15 contiguous nucleotides of SED ID NO: 98, and wherein each strand of said iRNA agent is between 15 and 30 base pairs in length.

2. The iRNA agent of claim 1, comprising a non-nucleotide moiety.

3. The iRNA agent of claim 1, comprising a phosphorothioate linkage.

4. The iRNA agent of claim 3, wherein said iRNA agent comprises a phosphorothioate at the first and second internucleotide linkage at the 3' end of the antisense strand.

5. The iRNA agent of claim 3, wherein said iRNA agent comprises a phosphorothioate at the first internucleotide linkage at the 3' end of the sense strand.

6. The iRNA agent of claim 1, comprising a 2'-modified nucleotide.

7. The iRNA agent of claim 6, wherein the 2'-modification is chosen from the group of: 2'-deoxy, 2'-deoxy-2'-fluoro, 2'-O-methyl, 2'-O-methoxyethyl (2'-O-MOE), 2'-0-aminopropyl (2'-O-AP), 2'-0-dimethylaminoethyl (2'-O-DMAOE), 2'-dimethylaminopropyl (2'-O-DMAP), 2'-O-dimethylaminoethyloxyethyl (2'-O-DMAEOE), and 2'-O—N-methylacetamido (2'-O-NMA).

8. The iRNA agent of claim 6, comprising: at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; or at least one 5'-uridine-uridine-3' (5'-UU-3') dinucleotide, wherein the 5'-uridine is a 2'-modified nucleotide.

9. The iRNA agent of claim 8, wherein said antisense strand consists of SEQ ID NO:254.

10. The iRNA agent of claim 8, wherein the 5'-most pyrimidines in all occurrences of sequence motif 5'-UA-3',5'-CA-3',5'-UU-3', and 5'-UG-3' on the antisense strand are 2'-modified nucleotides.

11. The iRNA agent of claim 10, wherein said antisense strand consists of SEQ ID NO:256.

12. The iRNA agent of claim 1, wherein a 5'-end of said iRNA agent comprises an adenosine, cytidine, guanosine, thymidine, or uridine.

13. The iRNA agent of claim 1, comprising a nucleotide overhang having 1 to 4 nucleotides.

14. The iRNA agent of claim 13, wherein the nucleotide overhang has 2 or 3 unpaired nucleotides.

15. The iRNA agent of claim 13, wherein the nucleotide overhang is at the 3'-end of the antisense strand of the iRNA agent.

16. The mRNA agent of claim 1, comprising a cholesterol moiety.

17. The iRNA agent of claim 16, wherein the cholesterol moiety is conjugated to the 3'-end of the sense strand of the iRNA agent.

18. The iRNA agent of claim 9 or 11, wherein said sense strand is selected from the group consisting of: SEQ ID NO:253, SEQ ID NO:255, and SEQ ID NO: 261.

19. The iRNA agent of claim 9, wherein said sense strand consists of SEQ ID NO:253.

20. The iRNA agent of claim 1, wherein said sense strand consists of SEQ ID NO:97 and said antisense strand consists of SEQ ID NO:98.

21. The iRNA agent of claim 1, wherein said sense strand consists of SEQ ID NO:275 and said antisense strand consists of SEQ ID NO:276.

22. The iRNA agent of claim 1, wherein said antisense strand consists of SEQ ID NO:98.

23. The iRNA agent of claim 1, wherein said iRNA agent reduces the amount of ApoB mRNA present in cultured mouse cells of hepatic origin.

24. The mRNA agent of claim 1, wherein the agent reduces the amount of ApoB mRNA in cultured human HepG2 cells after incubation with the agent by more than 50% compared to cells that have not been incubated with the agent, or reduces the amount of ApoB protein secreted into cell culture supernatant by more than 50%.

25. A method for reducing the expression levels of ApoB in a subject, comprising the step of administering an iRNA agent to said subject, wherein said sense strand comprises a first sequence and said antisense strand comprises a second sequence, wherein said first sequence is complementary to said second sequence, and wherein said second sequence comprises at least 15 contiguous nucleotides of SED ID NO: 98, and wherein each strand of said iRNA agent is between 15 and 30 base pairs in length.

* * * * *

UNITED STATES PATENT AND TRADEMARK OFFICE
CERTIFICATE OF CORRECTION

PATENT NO.       : 8,188,061 B2  
APPLICATION NO.  : 12/728139  
DATED            : May 29, 2012  
INVENTOR(S)      : Juergen Soutschek et al.

Page 1 of 1

It is certified that error appears in the above-identified patent and that said Letters Patent is hereby corrected as shown below:

Column 192, lines 60, please change "mRNA" to "iRNA"

Column 193, lines 15, please change "mRNA" to "iRNA"

Signed and Sealed this  
Fourth Day of September, 2012

David J. Kappos  
*Director of the United States Patent and Trademark Office*